United States Patent
Liverton et al.

(10) Patent No.: US 10,017,504 B2
(45) Date of Patent: Jul. 10, 2018

(54) PIPERIDINE ISOXAZOLE AND ISOTHIAZOLE OREXIN RECEPTOR ANTAGONISTS

(71) Applicant: MERCK SHARP & DOHME CORP., Rahway, NJ (US)

(72) Inventors: Nigel Liverton, Harleysville, PA (US); Scott D. Kuduk, Harleysville, PA (US); Douglas Beshore, Lower Gwynedd, PA (US); Yunfu Luo, Shanghai (CN); Na Meng, Shanghai (CN); Tingting Yu, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/523,252

(22) PCT Filed: Oct. 27, 2015

(86) PCT No.: PCT/US2015/057445
§ 371 (c)(1),
(2) Date: Apr. 28, 2017

(87) PCT Pub. No.: WO2016/069517
PCT Pub. Date: May 6, 2016

(65) Prior Publication Data
US 2017/0327490 A1    Nov. 16, 2017

(30) Foreign Application Priority Data
Oct. 30, 2014  (WO) ............... PCT/CN2014/089933

(51) Int. Cl.
| | | |
|---|---|---|
| *C07D 413/04* | (2006.01) |
| *C07D 413/14* | (2006.01) |
| *C07D 417/04* | (2006.01) |
| *C07D 417/14* | (2006.01) |
| *A61K 31/4525* | (2006.01) |
| *A61K 31/4535* | (2006.01) |
| *A61K 31/4545* | (2006.01) |
| *A61K 31/454* | (2006.01) |
| *A61K 31/506* | (2006.01) |

(52) U.S. Cl.
CPC ......... *C07D 413/14* (2013.01); *C07D 413/04* (2013.01); *C07D 417/04* (2013.01); *C07D 417/14* (2013.01)

(58) Field of Classification Search
None
See application file for complete search history.

(56) References Cited

U.S. PATENT DOCUMENTS

| | | |
|---|---|---|
| 5,010,102 A | 4/1991 | Felman et al. |
| 7,951,797 B2 | 5/2011 | Breslin et al. |
| 8,242,121 B2 | 8/2012 | Coleman et al. |
| 8,263,586 B2 | 9/2012 | Cox et al. |
| 8,349,872 B2 | 1/2013 | Coleman et al. |
| 8,357,700 B2 | 1/2013 | Cox et al. |
| 8,357,709 B2 | 1/2013 | Coleman et al. |
| 8,362,009 B2 | 1/2013 | Bergman et al. |
| 8,399,494 B2 | 3/2013 | Bergman et al. |
| 8,466,281 B2 | 6/2013 | Coleman et al. |
| 8,618,102 B2 | 12/2013 | Coleman et al. |
| 8,623,863 B2 | 1/2014 | Coleman et al. |
| 8,669,272 B2 | 3/2014 | Breslin et al. |
| 8,685,961 B2 | 4/2014 | Brashear et al. |
| 8,710,076 B2 | 4/2014 | Breslin et al. |
| 8,940,898 B2 | 1/2015 | Kuduk et al. |
| 9,029,364 B2 | 5/2015 | Kuduk et al. |
| 9,156,819 B2 | 10/2015 | Kuduk et al. |

(Continued)

FOREIGN PATENT DOCUMENTS

| | | |
|---|---|---|
| EP | 1685105 | 10/2008 |
| WO | WO2008147518 A1 | 12/2008 |

(Continued)

OTHER PUBLICATIONS

Anthony J. Roecker et al, Orexin Receptor Antagonists: New Therapeutic Agents for the Treatment of Insomnia, Journal of Medicinal Chemistry, 2016, 504-530, 59(2).

(Continued)

*Primary Examiner* — Emily Bernhardt
(74) *Attorney, Agent, or Firm* — J. Eric Thies; John C. Todaro

(57) ABSTRACT

The present invention is directed to piperidine isoxazole and isothiazole orexin compounds which are antagonists of orexin receptors. Such compounds are of the general structural formula I:

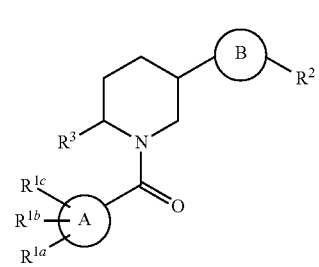

wherein the variables are defined herein.

The present invention is also directed to uses of the compounds described herein in the potential treatment or prevention of neurological and psychiatric disorders and diseases in which orexin receptors are involved. The present invention is also directed to compositions comprising these compounds. The present invention is also directed to uses of these compositions in the prevention or treatment of such diseases in which orexin receptors are involved.

15 Claims, No Drawings

(56) References Cited

U.S. PATENT DOCUMENTS

| | | |
|---|---|---|
| 9,546,152 B2 | 1/2017 | Kuduk et al. |
| 9,550,786 B2 | 1/2017 | Cooke et al. |
| 9,556,145 B2 | 1/2017 | Kuduk et al. |
| 9,556,190 B2 | 1/2017 | Kuduk et al. |
| 9,586,934 B2 | 3/2017 | Kuduk et al. |
| 9,586,950 B2 | 3/2017 | Kuduk et al. |
| 9,617,246 B2 | 4/2017 | Kuduk et al. |
| 9,624,197 B2 | 4/2017 | Kuduk et al. |
| 2007/0117804 A1 | 5/2007 | Zhao et al. |
| 2007/0219187 A1* | 9/2007 | Bessis .............. C07D 211/18 514/228.8 |
| 2010/0029736 A1 | 2/2010 | Cox et al. |
| 2011/0195957 A1 | 8/2011 | Bergman et al. |
| 2012/0196901 A1 | 8/2012 | Coleman et al. |
| 2015/0322039 A1 | 11/2015 | Kuduk et al. |
| 2015/0322040 A1 | 11/2015 | Kuduk et al. |
| 2015/0322041 A1 | 11/2015 | Kuduk et al. |
| 2016/0016935 A1 | 1/2016 | Kuduk et al. |
| 2016/0068510 A1 | 3/2016 | Kuduk et al. |
| 2016/0068514 A1 | 3/2016 | Kuduk |
| 2016/0102073 A1 | 4/2016 | Kuduk et al. |
| 2016/0176858 A1 | 6/2016 | Liverton et al. |
| 2016/0185768 A1 | 6/2016 | Liverton et al. |
| 2016/0304490 A1 | 10/2016 | Kuduk et al. |
| 2016/0318900 A1 | 11/2016 | Kuduk et al. |
| 2016/0318923 A1 | 11/2016 | Kuduk et al. |

FOREIGN PATENT DOCUMENTS

| | | |
|---|---|---|
| WO | WO2010048010 | 4/2010 |
| WO | WO2010124055 | 10/2010 |
| WO | WO2014137883 | 9/2014 |
| WO | WO2016069510 | 5/2016 |
| WO | WO2016069512 | 5/2016 |
| WO | WO2016069515 | 5/2016 |
| WO | WO2016069517 | 5/2016 |
| WO | WO2016069519 | 5/2016 |
| WO | WO2016085783 | 6/2016 |
| WO | WO2016085784 | 6/2016 |
| WO | WO2016089721 | 6/2016 |
| WO | WO2016089722 | 6/2016 |
| WO | WO2016100154 | 6/2016 |
| WO | WO2016100156 | 6/2016 |
| WO | WO2016100157 | 6/2016 |
| WO | WO2016100161 | 6/2016 |
| WO | WO2016100162 | 6/2016 |
| WO | WO2016106105 | 6/2016 |
| WO | WO2016106106 | 6/2016 |

OTHER PUBLICATIONS

Jason W. Skudlarek et al, Investigation of orexin-2 selective receptor antagonists: Structural modifications resulting in dual orexin receptor antagonists, Bioorganic & Medicinal Chemistry Letters, 2017, 1364-1370, 27(6).

Khulusi et al, Helicobacter Pylori Infection Density and Gastric Inflammation in Duodenal Ulcer and Non-Ulcer Subjects, Gut, 1995, 319-324, 37.

Pubchem SID—216507465—Oct. 20, 2014-1-6.

* cited by examiner

PIPERIDINE ISOXAZOLE AND ISOTHIAZOLE OREXIN RECEPTOR ANTAGONISTS

CROSS REFERENCE TO RELATED APPLICATIONS

This application is U.S. National Phase application under 35 U.S.C. § 371 of PCT Application No. PCT/US2015/057445, filed Oct. 27, 2015, which claims priority from PCT Application No. PCT/CN2014/089933, filed Oct. 30, 2014.

BACKGROUND OF THE INVENTION

The orexins (hypocretins) comprise two neuropeptides produced in the hypothalamus: orexin A (OX-A) (a 33 amino acid peptide) and orexin B (OX-B) (a 28 amino acid peptide) (Sakurai T. et al., Cell, 1998, 92, 573-585). Orexins are found to stimulate food consumption in rats suggesting a physiological role for these peptides as mediators in the central feedback mechanism that regulates feeding behavior (Sakurai T. et al., Cell, 1998, 92, 573-585). Orexins regulate states of sleep and wakefulness opening potentially novel therapeutic approaches for narcoleptic or insomniac patients (Chemelli R. M. et al., Cell, 1999, 98, 437-451). Orexins have also been indicated as playing a role in arousal, reward, learning and memory (Harris, et al., Trends Neurosci., 2006, 29 (10), 571-577). Two orexin receptors have been cloned and characterized in mammals. They belong to the super family of G-protein coupled receptors (Sakurai T. et al., Cell, 1998, 92, 573-585): the orexin-1 receptor (OX or OX1R) is selective for OX-A, and the orexin-2 receptor (OX2 or OX2R) is capable of binding OX-A as well as OX-B. The physiological actions in which orexins are presumed to participate are thought to be expressed via one or both of OX1 receptor and OX2 receptor as the two subtypes of orexin receptors.

SUMMARY OF THE INVENTION

The present invention is directed to piperidine isoxazole and isothiazole compounds which are antagonists of orexin receptors. The present invention is also directed to uses of the compounds described herein in the potential treatment or prevention of neurological and psychiatric disorders and diseases in which orexin receptors are involved. The present invention is also directed to compositions comprising these compounds. The present invention is also directed to uses of these compositions in the potential prevention or treatment of such diseases in which orexin receptors are involved.

DETAILED DESCRIPTION OF THE INVENTION

The present invention is directed to compounds of the formula I:

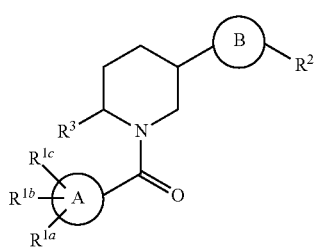

wherein:
A ring is selected from the group consisting of phenyl, naphthyl and heteroaryl;

B ring is

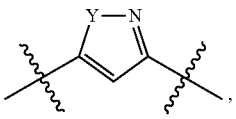

wherein symbol

indicates a bond of attachment;
Y is O or S;
each of $R^{1a}$, $R^{1b}$ and $R^{1c}$ is independently selected from the group consisting of:
(1) hydrogen,
(2) halogen,
(3) hydroxyl,
(4) $-(C=O)_m-O_n-C_{1-6}$alkyl, where the alkyl is unsubstituted or substituted with one to four substituents independently selected from $R^4$,
(5) $-(C=O)_m-O_n-C_{3-6}$cycloalkyl, where the cycloalkyl is unsubstituted or substituted with one to four substituents independently selected from $R^4$,
(6) $-(C=O)_m-C_{2-4}$alkenyl, where the alkenyl is unsubstituted or substituted with one to four substituents independently selected from $R^4$,
(7) $-(C=O)_m-C_{2-4}$alkynyl, where the alkynyl is unsubstituted or substituted with one to four substituents independently selected from $R^4$,
(8) $-(C=O)_m-O_n$-phenyl or $-(C=O)_m-O_n$-naphthyl, where the phenyl or naphthyl is unsubstituted or substituted with one to four substituents independently selected from $R^4$,
(9) $-(C=O)_m-O_n$-heterocycle, where the heterocycle is unsubstituted or substituted with one to four substituents independently selected from $R^4$,
(10) $-(C=O)_m-NR^{10}R^{11}$,
(11) $-S(O)_2-NR^{10}R^{11}$,
(12) $-S(O)_q-R^{10}$, where q is 0, 1 or 2,
(13) $-CO_2H$,
(14) $-CN$, and
(15) $-NO_2$;
$R^2$ is selected from the group consisting of:
(1) $C_{1-6}$alkyl, which is unsubstituted or substituted with one to four substituents independently selected from the group consisting of halogen, hydroxyl, $C_{3-6}$cycloalkyl, $-O-C_{1-6}$alkyl, $-NH_2$, $-NH-C_{1-6}$alkyl, $-N(C_{1-6}$alkyl$)(C_{1-6}$alkyl$)$, $-(C=O)O-C_{1-6}$alkyl and phenyl, wherein the phenyl is unsubstituted or substituted with one to four substituents independently selected from the group consisting of $C_{1-6}$alkyl, halogen and $C_{1-6}$alkyl-OH,
(2) $C_{3-6}$cycloalkyl, which is unsubstituted or substituted with one to four substituents independently selected from the group consisting of $C_{1-6}$alkyl, halogen, hydroxyl, $-O-C_{1-6}$alkyl, $-NH_2$, $-NH-C_{1-6}$alkyl, $-N(C_{1-6}$alkyl$)(C_{1-6}$alkyl$)$, $-(C=O)O-C_{1-6}$alkyl and phenyl, wherein the phenyl is unsubstituted or substituted with one to four substituents independently selected from the group consisting of $C_{1-6}$alkyl, halogen and $C_{1-6}$alkyl-OH, (3) aryl, which is unsubstituted or substituted with one to four substituents independently selected from the group consisting of halogen, hydroxyl and phenyl,
(4) heterocycle, which is unsubstituted or substituted with one to four substituents independently selected from $R^4$,
(5) halogen,
(6) —CN,
(7) —(C=O)O—$C_{1-6}$alkyl, and
(8) —(C=O)$NH_2$;
$R^3$ is selected from $C_{1-6}$alkyl and $C_{3-6}$cycloalkyl, wherein each of the alkyl and cycloalkyl is unsubstituted or substituted with one to two substituents independently selected from $R^4$;
$R^4$ is selected from the group consisting of:
(1) hydroxyl,
(2) halogen,
(3) $C_{1-6}$alkyl,
(4) —$C_{3-6}$cycloalkyl,
(5) —O—$C_{1-6}$alkyl,
(6) —O(C=O)—$C_{1-6}$alkyl,
(7) —$NH_2$,
(8) —NH—$C_{1-6}$alkyl,
(9) —$NO_2$,
(10) phenyl,
(11) heterocycle,
(12) —$CO_2H$,
(13) —CN, and
(14) —$S(O)_2$—$C_{1-6}$alkyl;
each of $R^{10}$ and $R^{11}$ is independently selected from the group consisting of:
(a) hydrogen,
(b) $C_{1-6}$alkyl, which is unsubstituted or substituted with one to four substituents independently selected from $R^4$,
(c) $C_{3-6}$alkenyl, which is unsubstituted or substituted with one to four substituents independently selected from $R^4$,
(d) $C_{3-6}$alkynyl, which is unsubstituted or substituted with one to four substituents independently selected from $R^4$,
(e) $C_{3-6}$cycloalkyl which is unsubstituted or substituted with one to four substituents independently selected from $R^4$,
(f) phenyl, which is unsubstituted or substituted with one to four substituents independently selected from $R^4$, and
(g) heterocycle, which is unsubstituted or substituted with one to four substituents independently selected from $R^4$; and
m is 0 or 1, n is 0 or 1 (wherein if m is 0 or n is 0, a bond is present);
or a pharmaceutically acceptable salt thereof.

An embodiment of the present invention includes compounds of the formula Ia:

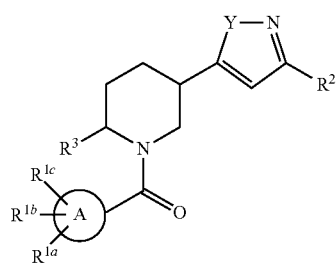

wherein Y is O or S; $R^{1a}$, $R^{1b}$, $R^{1c}$, $R^2$ and $R^3$ are defined herein; or a pharmaceutically acceptable salt thereof.

An embodiment of the present invention includes compounds of the formula Ib:

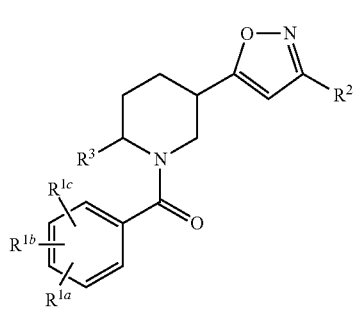

wherein $R^{1a}$, $R^{1b}$, $R^{1c}$, $R^2$ and $R^3$ are defined herein; or a pharmaceutically acceptable salt thereof.

An embodiment of the present invention includes compounds of the formula Ic:

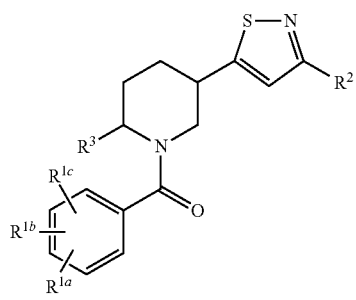

wherein $R^{1a}$, $R^{1b}$, $R^{1c}$, $R^2$ and $R^3$ are defined herein; or a pharmaceutically acceptable salt thereof.

An embodiment of the present invention includes compounds of the formula Id:

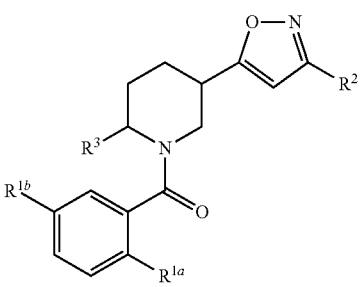

wherein $R^{1a}$, $R^{1b}$, $R^2$ and $R^3$ are defined herein; or a pharmaceutically acceptable salt thereof.

An embodiment of the present invention includes compounds of the formula Ie:

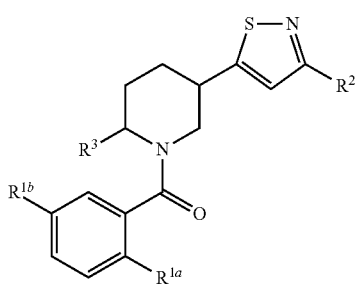

wherein $R^{1a}$, $R^{1b}$, $R^2$ and $R^3$ are defined herein; or a pharmaceutically acceptable salt thereof.

An embodiment of the present invention includes compounds of the formula If:

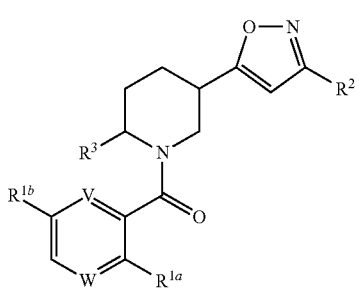

wherein each of V and W is independently CH or N; $R^{1a}$, $R^{1b}$, $R^2$ and $R^3$ are defined herein; or a pharmaceutically acceptable salt thereof. An embodiment of the present invention includes compounds wherein V is CH and W is N. An embodiment of the present invention includes compounds wherein V is N and W is N. An embodiment of the present invention includes compounds wherein V is N and W is CH.

An embodiment of the present invention includes compounds of the formula Ig:

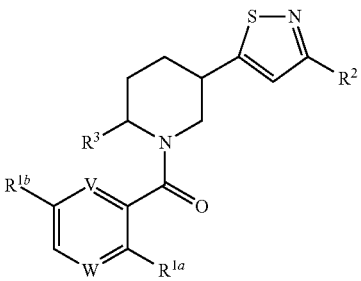

wherein each of V and W is independently CH or N; $R^{1a}$, $R^{1b}$, $R^2$ and $R^3$ are defined herein; or a pharmaceutically acceptable salt thereof. An embodiment of the present invention includes compounds wherein V is CH and W is N. An embodiment of the present invention includes compounds wherein V is N and W is N. An embodiment of the present invention includes compounds wherein V is N and W is CH.

An embodiment of the present invention includes compounds of the formula Ih:

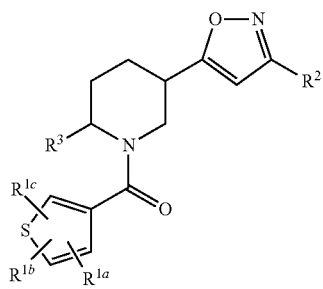

wherein $R^{1a}$, $R^{1b}$, $R^{1c}$, $R^2$ and $R^3$ are defined herein; or a pharmaceutically acceptable salt thereof.

An embodiment of the present invention includes compounds of the formula Ii:

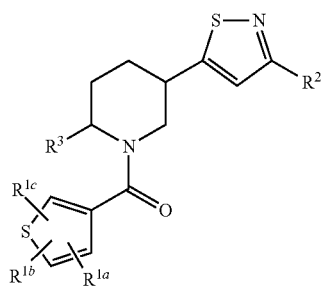

wherein $R^{1a}$, $R^{1b}$, $R^{1c}$, $R^2$ and $R^3$ are defined herein; or a pharmaceutically acceptable salt thereof.

An embodiment of the present invention includes compounds of the formula IIa:

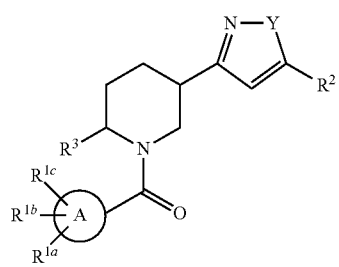

wherein Y is O or S; $R^{1a}$, $R^{1b}$, $R^{1c}$, $R^2$ and $R^3$ are defined herein; or a pharmaceutically acceptable salt thereof An embodiment of the present invention includes compounds of the formula IIb:

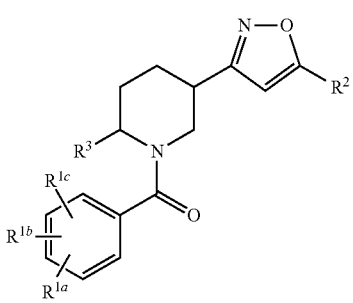

wherein $R^{1a}$, $R^{1b}$, $R^{1c}$, $R^2$ and $R^3$ are defined herein; or a pharmaceutically acceptable salt thereof.

An embodiment of the present invention includes compounds of the formula IIc:

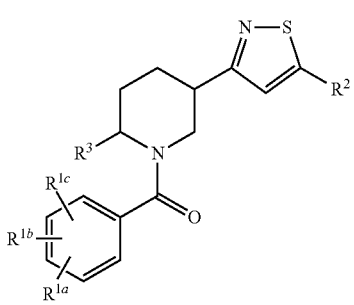

wherein $R^{1a}$, $R^{1b}$, $R^{1c}$, $R^2$ and $R^3$ are defined herein; or a pharmaceutically acceptable salt thereof.

An embodiment of the present invention includes compounds of the formula IId:

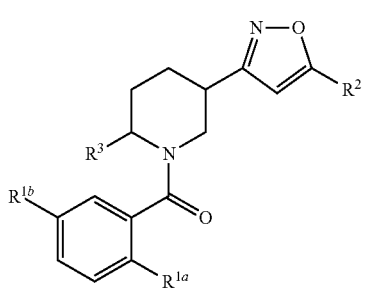

wherein $R^{1a}$, $R^{1b}$, $R^2$ and $R^3$ are defined herein; or a pharmaceutically acceptable salt thereof.

An embodiment of the present invention includes compounds of the formula IIe:

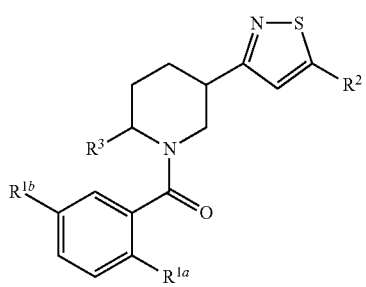

wherein $R^{1a}$, $R^{1b}$, $R^2$ and $R^3$ are defined herein; or a pharmaceutically acceptable salt thereof.

An embodiment of the present invention includes compounds of the formula IIf:

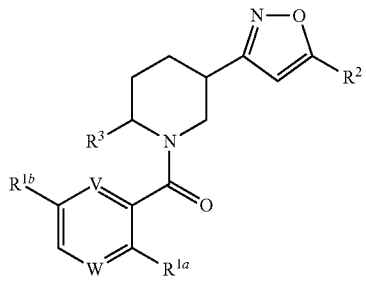

wherein each of V and W is independently CH or N; $R^{1a}$, $R^{1b}$, $R^2$ and $R^3$ are defined herein; or a pharmaceutically acceptable salt thereof. An embodiment of the present invention includes compounds wherein V is CH and W is N. An embodiment of the present invention includes compounds wherein V is N and W is N. An embodiment of the present invention includes compounds wherein V is N and W is CH.

An embodiment of the present invention includes compounds of the formula IIg:

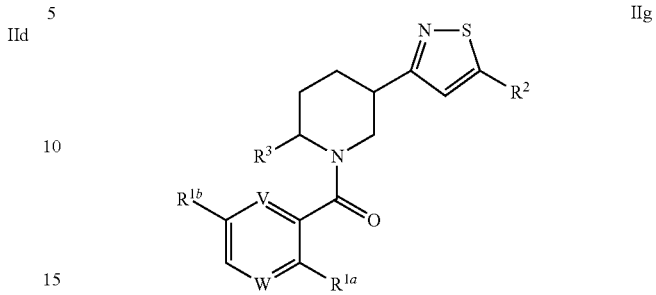

wherein each of V and W is independently CH or N; $R^{1a}$, $R^{1b}$, $R^2$ and $R^3$ are defined herein; or a pharmaceutically acceptable salt thereof. An embodiment of the present invention includes compounds wherein V is CH and W is N. An embodiment of the present invention includes compounds wherein V is N and W is N. An embodiment of the present invention includes compounds wherein V is N and W is CH.

An embodiment of the present invention includes compounds of the formula IIh:

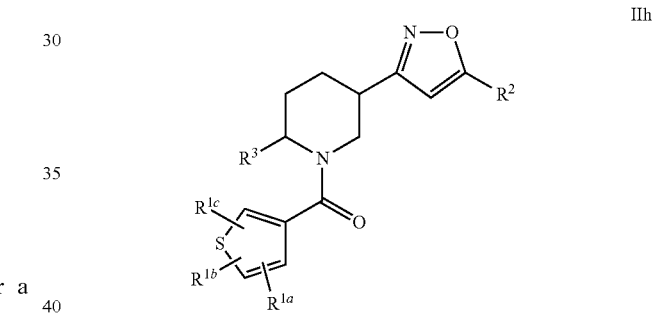

wherein $R^{1a}$, $R^{1b}$, $R^{1c}$, $R^2$ and $R^3$ are defined herein; or a pharmaceutically acceptable salt thereof.

An embodiment of the present invention includes compounds of the formula IIi:

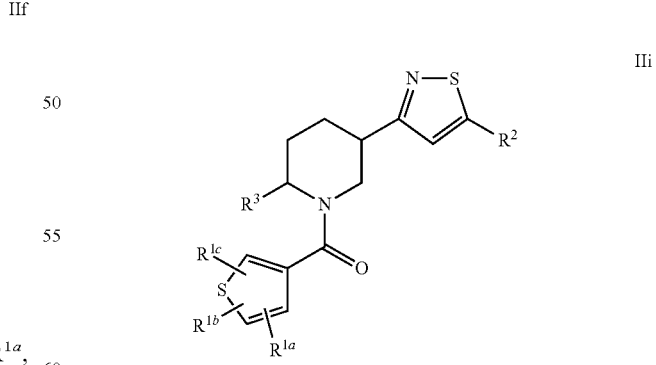

wherein $R^{1a}$, $R^{1b}$, $R^{1c}$, $R^2$ and $R^3$ are defined herein; or a pharmaceutically acceptable salt thereof.

An embodiment of the present invention includes compounds of the formula I, Ia, or IIa, wherein the A ring is selected from phenyl, pyridyl, thiophenyl, thiazolyl, isothiazolyl, pyrazinyl and pyrazolyl. An embodiment of the present invention includes compounds wherein A is phenyl. An embodiment of the present invention includes compounds wherein A is pyridyl.

An embodiment of the present invention includes compounds wherein A is thiophenyl. An embodiment of the present invention includes compounds wherein A is thiazolyl. An embodiment of the present invention includes compounds wherein A is isothiazolyl. An embodiment of the present invention includes compounds wherein A is pyrazinyl. An embodiment of the present invention includes compounds wherein A is pyrazolyl.

In an embodiment of each previous embodiment that includes compounds of the formula I, Ia, Ib, Ic, Id, Ie, If, Ig, Ih, Ii, IIa, IIb, IIc, IId, IIe, IIf, IIg, IIh or IIi, each of $R^{1a}$, $R^{1b}$ and $R^{1c}$, if present, is independently selected from the group consisting of:
(1) hydrogen,
(2) halogen,
(3) hydroxyl,
(4) $C_{1-6}$alkyl, which is unsubstituted or substituted with one to four substituents independently selected from the group consisting of halogen, hydroxyl, $C_{3-6}$cycloalkyl and phenyl,
(5) —O—$C_{1-6}$alkyl, which is unsubstituted or substituted with one to four substituents independently selected from the group consisting of halogen, hydroxyl, $C_{3-6}$cycloalkyl and phenyl,
(6) heteroaryl, wherein the heteroaryl is selected from triazolyl, tetrazolyl, oxazolyl, pyrrolyl, imidazolyl, indolyl, pyridyl, pyrazolyl, pyrazinyl and pyrimidinyl, which is unsubstituted or substituted with one to four substituents independently selected from the group consisting of halogen, hydroxyl, $C_{1-6}$alkyl, —O—$C_{1-6}$alkyl and —$NO_2$,
(7) phenyl, which is unsubstituted or substituted with one to three substituents independently selected from the group consisting of halogen, hydroxyl, $C_{1-6}$alkyl, —O—$C_{1-6}$alkyl and —$NO_2$,
(8) —O-phenyl, which is unsubstituted or substituted with one to four substituents independently selected from the group consisting of halogen, hydroxyl, $C_{1-6}$alkyl, —O—$C_{1-6}$alkyl and —$NO_2$,
(9) —CN, and
(10) —NH—$C_{1-6}$alkyl, or —N($C_{1-6}$alkyl)($C_{1-6}$alkyl), wherein each $C_{1-6}$alkyl is independently unsubstituted or substituted with one to four substituents independently selected from the group consisting of halogen, hydroxyl, $C_{1-6}$alkyl, and —O—$C_{1-6}$alkyl.

In an embodiment of each previous embodiment that includes compounds of the formula I, Ia, Ib, Ic, Id, Ie, If, Ig, Ih, Ii, IIa, IIb, IIc, IId, IIe, IIf, IIg, IIh or IIi, each of $R^{1a}$, $R^{1b}$ and $R^{1c}$ (when present) is independently selected from the group consisting of:
(1) hydrogen,
(2) halogen,
(3) hydroxyl,
(4) $C_{1-6}$alkyl, which is unsubstituted or substituted with one to four substituents independently selected from the group consisting of halogen, hydroxyl, $C_{3-6}$cycloalkyl and phenyl,
(5) —O—$C_{1-6}$alkyl, which is unsubstituted or substituted with one to four substituents independently selected from the group consisting of halogen, hydroxyl, $C_{3-6}$cycloalkyl and phenyl,
(6) $C_{3-6}$cycloalkyl, wherein the cycloalkyl is unsubstituted or substituted with one to four substituents independently selected from $R^4$,
(7) —CN, and
(8) heteroaryl selected from triazolyl, tetrazolyl, oxazolyl, pyrrolyl, imidazolyl, indolyl, pyridyl, pyrazolyl, pyrazinyl and pyrimidinyl, which is unsubstituted or substituted with one to four substituents independently selected from the group consisting of halogen, hydroxyl, $C_{1-6}$alkyl, —O—$C_{1-6}$alkyl and —$NO_2$.

In an embodiment of each previous embodiment that includes compounds of the formula I, Ia, Ib, Ic, Id, Ie, If, Ig, Ih, Ii, IIa, IIb, IIc, IId, IIe, IIf, IIg, IIh or IIi, each of $R^{1a}$, $R^{1b}$ and $R^{1c}$ (when present) is independently selected from the group consisting of:
(1) hydrogen,
(2) halogen,
(3) $C_{1-6}$alkyl, which is unsubstituted or substituted with one to three substituents independently selected from the group consisting of halogen, hydroxyl, and $C_{3-6}$cycloalkyl,
(4) —O—$C_{1-6}$alkyl, which is unsubstituted or substituted with halogen,
(5) —CN, and
(6) heteroaryl selected from triazolyl, tetrazolyl, oxazolyl, pyrrolyl, imidazolyl, indolyl, pyridyl, pyrazolyl, pyrazinyl and pyrimidinyl.

In an embodiment of each previous embodiment that includes compounds of the formula I, Ia, Ib, Ic, Id, Ie, If, Ig, Ih, Ii, IIa, IIb, IIc, IId, IIe, IIf, IIg, IIh or IIi, $R^{1c}$, if present, is hydrogen, and each of $R^{1a}$ and $R^{1b}$ is independently selected from the group consisting of:
(1) hydrogen,
(2) fluoro,
(3) chloro,
(4) bromo,
(5) methyl,
(6) ethyl,
(7) trifluoromethyl,
(8) cyclopropyl, which is unsubstituted or substituted with —CN,
(9) —O—$C_{1-4}$alkyl which is unsubstituted or substituted with 1-3 halogens, and
(10) heteroaryl selected from triazolyl, tetrazolyl, oxazolyl, pyrrolyl, imidazolyl, indolyl, pyridyl, pyrazolyl, pyrazinyl and pyrimidinyl.

In an embodiment of each previous embodiment that includes compounds of the formula I, Ia, Ib, Ic, Id, Ie, If, Ig, Ih, Ii, IIa, IIb, IIc, IId, IIe, IIf, IIg, IIh or IIi, $R^{1c}$, if present, is hydrogen, $R^{1b}$ is hydrogen, and $R^{1a}$ is selected from the group consisting of:
(1) triazolyl,
(2) tetrazolyl,
(3) oxazolyl,
(4) pyrrolyl,
(5) imidazolyl,
(6) pyridyl,
(7) pyrazolyl,
(8) pyrazinyl, and
(9) pyrimidinyl.

In an embodiment of each previous embodiment that includes compounds of the formula I, Ia, Ib, Ic, Id, Ie, If, Ig, Ih, Ii, IIa, IIb, IIc, IId, IIe, IIf, IIg, IIh or IIi, $R^{1c}$, if present, is hydrogen, $R^{1b}$ is hydrogen, and $R^{1a}$ is selected from the group consisting of:
(1) triazolyl,
(2) tetrazolyl,
(3) pyrazolyl,
(4) pyrazinyl, and
(5) pyrimidinyl.

In an embodiment of each previous embodiment that includes compounds of the formula I, Ia, Ib, Ic, Id, Ie, If, Ig, Ih, Ii, IIa, IIb, IIc, IId, IIe, IIf, IIg, IIh or IIi, $R^2$ is selected from the group consisting of:
  (1) $C_{1-6}$alkyl, which is unsubstituted or substituted with one to four substituents independently selected from the group consisting of halogen, hydroxyl, $C_{3-6}$cycloalkyl, —O—$C_{1-6}$alkyl, —$NH_2$, —NH—$C_{1-6}$alkyl, —(C=O)O—$C_{1-6}$alkyl, and phenyl, wherein the phenyl is unsubstituted or substituted with $C_{1-6}$alkyl, halogen, or $C_{1-6}$alkyl-OH,
  (2) $C_{3-6}$cycloalkyl, which is unsubstituted or substituted with one to four substituents independently selected from the group consisting of $C_{1-6}$alkyl, halogen, hydroxyl, —O—$C_{1-6}$alkyl, —$NH_2$, —NH—$C_{1-6}$alkyl, —(C=O)O—$C_{1-6}$alkyl, and phenyl, wherein the phenyl is unsubstituted or substituted with $C_{1-6}$alkyl, halogen, or $C_{1-6}$alkyl-OH,
  (3) aryl, which is unsubstituted or substituted with halogen, hydroxyl or phenyl,
  (4) heterocycle, which is unsubstituted or substituted with $R^4$,
  (5) halogen,
  (6) —CN,
  (7) —(C=O)O—$C_{1-6}$alkyl, and
  (8) —(C=O)$NH_2$.

In an embodiment of each previous embodiment that includes compounds of the formula I, Ia, Ib, Ic, Id, Ie, If, Ig, Ih, Ii, IIa, IIb, IIc, IId, IIe, IIf, IIg, IIh or IIi, $R^2$ is selected from the group consisting of:
  (1) $C_{1-6}$alkyl,
  (2)

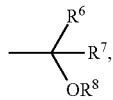

wherein each of $R^6$ and $R^7$ is independently selected from the group consisting of hydrogen, —$C_{1-2}$alkyl, —$C_{1-2}$alkyl substituted with 1-3 halogens and —$C_{3-6}$cycloalkyl; and $R^8$ is hydrogen or —$C_{1-6}$alkyl,
  (3) $C_{3-6}$cycloalkyl, which is unsubstituted or substituted with one to three substituents independently selected from the group consisting of $C_{1-6}$alkyl, halogen, hydroxyl, —O—$C_{1-6}$alkyl, —$NH_2$, —NH—$C_{1-6}$alkyl, —(C=O)O—$C_{1-6}$alkyl, and phenyl, wherein the phenyl is unsubstituted or substituted with $C_{1-6}$alkyl, halogen, or $C_{1-6}$alkyl-OH, and
  (4) heterocycle, which is unsubstituted or substituted with $R^4$.

In an embodiment of each previous embodiment that includes compounds of the formula I, Ia, Ib, Ic, Id, Ie, If, Ig, Ih, Ii, IIa, IIb, IIc, IId, IIe, IIf, IIg, IIh or IIi, $R^2$ is selected from the group consisting of:
  (1) methyl,
  (2) ethyl,
  (3) propyl,
  (4) butyl,
  (5) trifluoromethyl,
  (6)

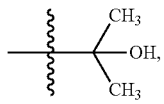

(7)

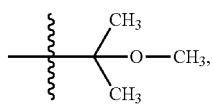

(8)

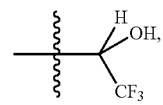

(9)

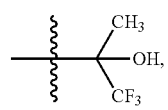

(10)

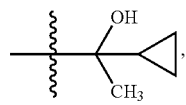

(11)

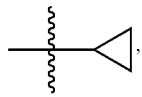

and
  (12) tetrahydrofuran.

In an embodiment of each previous embodiment that includes compounds of the formula I, Ia, Ib, Ic, Id, Ie, If, Ig, Ih, Ii, IIa, IIb, IIc, IId, IIe, IIf, IIg, IIh or IIi, $R^2$ is selected from the group consisting of:
  (1) isopropyl,
  (2) trifluoromethyl,
  (3) tert-butyl,
  (4)

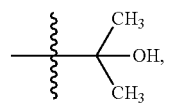 [SMILES: *C(C)(C)O]

(5)

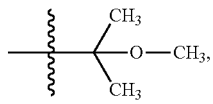

(6)

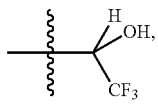

(7)

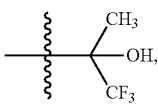

(8)

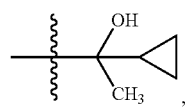

(9)

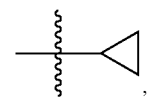

and
(10)

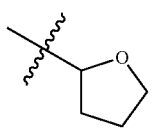

In an embodiment of each previous embodiment that includes compounds of the formula I, Ia, Ib, Ic, Id, Ie, If, Ig, Ih, Ii, IIa, IIb, IIc, IId, IIe, IIf, IIg, IIh or IIi, $R^2$ is selected from the group consisting of:
(1) trifluoromethyl,
(2)

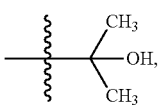

(3)

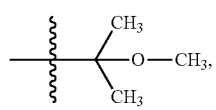

(4)

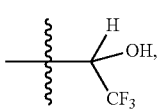

(5)

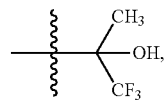

(6)

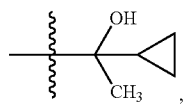 [SMILES: *C(C)(O)C1CC1]

and
(7)

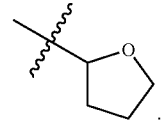 [SMILES: *C1CCCO1]

In an embodiment of each previous embodiment that includes compounds of the formula I, Ia, Ib, Ic, Id, Ie, If, Ig, Ih, Ii, IIa, IIb, IIc, IId, IIe, IIf, IIg, IIh or IIi, $R^3$ is $C_{1-6}$alkyl. In a further embodiment, $R^3$ is $C_{3-6}$cycloalkyl. In a further embodiment, $R^3$ is methyl or ethyl. In a further embodiment, $R^3$ is methyl. In a further embodiment, $R^3$ is (R)-methyl.

In an embodiment of each previous embodiment that includes compounds of the formula I, Ia, Ib, Ic, Id, Ie, If, Ig, Ih, Ii, IIa, IIb, IIc, IId, IIe, IIf, IIg, IIh or IIi, $R^4$ is selected from the group consisting of:
(1) hydroxyl,
(2) halogen,
(3) $C_{1-6}$alkyl,
(4) —$C_{3-6}$cycloalkyl,
(5) —O—$C_{1-6}$alkyl,
(6) —O(C=O)—$C_{1-6}$alkyl,
(7) —NH$_2$,
(7) —NH—$C_{1-6}$alkyl,
(8) —NO$_2$,
(9) phenyl,
(10) heterocycle,
(11) —CO$_2$H, and
(12) —CN.

In an embodiment of each previous embodiment that includes compounds of the formula I, Ia, Ib, Ic, Id, Ie, If, Ig, Ih, Ii, IIa, IIb, IIc, IId, IIe, IIf, IIg, IIh or IIi, $R^4$ is selected from the group consisting of:
(1) hydroxyl,
(2) halogen,
(3) $C_{1-6}$alkyl,
(4) —$C_{3-6}$cycloalkyl,
(5) —NH$_2$,
(6) phenyl,
(7) heterocycle, and
(8) —CN.

In an embodiment of each previous embodiment that includes compounds of the formula I, Ia, Ib, Ic, Id, Ie, If, Ig, Ih, Ii, IIa, IIb, IIc, IId, IIe, IIf, IIg, IIh or IIi, $R^4$ is selected from the group consisting of:
(1) hydroxyl,
(2) halogen,
(3) $C_{1-6}$alkyl, (4) —C$_{3-6}$cycloalkyl,
(5) —NH$_2$, and
(6) heterocycle.

In an embodiment of each previous embodiment that includes compounds of the formula I, Ia, Ib, Ic, Id, Ie, If, Ig, Ih, Ii, IIa, IIb, IIc, IId, IIe, IIf, IIg, IIh or IIi, R$^4$ is selected from the group consisting of:
(1) hydroxyl,
(2) halogen,
(3) C$_{1-6}$alkyl, and
(4) heterocycle.

In an embodiment of each previous embodiment that includes compounds of the formula I, Ia, Ib, Ic, Id, Ie, If, Ig, Ih, Ii, IIa, IIb, IIc, IId, IIe, IIf, IIg, IIh or IIi, Y is O or S. In a further embodiment, Y is O. In a further embodiment, Y is S.

An embodiment of the present invention includes a compound which is selected from the group consisting of the subject compounds of the Examples herein or a pharmaceutically acceptable salt thereof.

An embodiment of the present invention includes a compound which is selected from the group consisting of:

(1   2-{3-[(3R,6R)-6-Methyl-1-{[2-(2H-1,2,3-triazol-2-yl)phenyl]carbonyl}piperidin-3-yl]isoxazol-5-yl}propan-2-ol),
(1-(2-((2R,5R)-5-(5-(2-Hydroxypropan-2-yl)isoxazol-3-yl)-2-methylpiperidine-1-carbonyl)phenyl)cyclopropanecarbonitrile),
(5-Chloro-2-(2H-1,2,3-triazol-2-yl)phenyl)((2R,5R)-5-(5-(2-hydroxypropan-2-yl)isoxazol-3-yl)-2-methylpiperidin-1-yl)methanone,
(5-Fluoro-2-(2H-1,2,3-triazol-2-yl)phenyl)((2R,5R)-5-(5-(2-hydroxypropan-2-yl)isoxazol-3-yl)-2-methylpiperidin-1-yl)methanone,
((2-Ethoxyphenyl)((2R,5R)-5-(5-(2-hydroxypropan-2-yl)isoxazol-3-yl)-2-methylpiperidin-1-yl)methanone),
(((2R,5R)-5-(5-(2-Hydroxypropan-2-yl)isoxazol-3-yl)-2-methylpiperidin-1-yl)(2-isopropoxypyridin-3-yl)methanone),
((2R,5R)-5-(5-(2-Hydroxypropan-2-yl)isoxazol-3-yl)-2-methylpiperidin-1-yl)(2-(2,2,2-trifluoroethoxy)pyridin-3-yl)methanone,
(2-(2H-1,2,3-Triazol-2-yl)phenyl)((2R,5R)-5-(5-(3-hydroxypentan-3-yl)isoxazol-3-yl)-2-methylpiperidin-1-yl)methanone),
(1-Cyclopropyl-1-{3-[(3R,6R)-6-methyl-1-{[2-(2H-1,2,3-triazol-2-yl)phenyl]carbonyl}piperidin-3-yl]isoxazol-5-yl}ethanol),
(1-Cyclopropyl-1-{3-[(3R,6R)-6-methyl-1-{[2-(2H-1,2,3-triazol-2-yl)phenyl]carbonyl}piperidin-3-yl]isoxazol-5-yl}ethanol),
((2R)-2-{3-[(3R,6R)-6-Methyl-1-{[2-(2H-1,2,3-triazol-2-yl)phenyl]carbonyl}piperidin-3-yl]isoxazol-5-yl}butan-2-ol),
((2S)-2-{3-[(3R,6R)-6-Methyl-1-{[2-(2H-1,2,3-triazol-2-yl)phenyl]carbonyl}piperidin-3-yl]isoxazol-5-yl}butan-2-ol),
(1-{3-[(3R,6R)-6-Methyl-1-{[2-(2H-1,2,3-triazol-2-yl)phenyl]carbonyl}piperidin-3-yl]isoxazol-5-yl}cyclobutanol),
(1,1,1-Trifluoro-2-{3-[(3R,6R)-6-methyl-1-{[2-(2H-1,2,3-triazol-2-yl)phenyl]carbonyl}piperidin-3-yl]isoxazol-5-yl}propan-2-ol),
(1,1,1-Trifluoro-2-{3-[(3R,6R)-6-methyl-1-{[2-(2H-1,2,3-triazol-2-yl)phenyl]carbonyl}piperidin-3-yl]isoxazol-5-yl}propan-2-ol),
(3-Methyl-2-{3-[(3R,6R)-6-methyl-1-{[2-(2H-1,2,3-triazol-2-yl)phenyl]carbonyl}piperidin-3-yl]isoxazol-5-yl}butan-2-ol),
(3-Methyl-2-{3-[(3R,6R)-6-methyl-1-{[2-(2H-1,2,3-triazol-2-yl)phenyl]carbonyl}piperidin-3-yl]isoxazol-5-yl}butan-2-ol),
((2S)-1,1-Difluoro-2-{3-[(3R,6R)-6-methyl-1-{[2-(2H-1,2,3-triazol-2-yl)phenyl]carbonyl}piperidin-3-yl]isoxazol-5-yl}propan-2-ol),
((2R,5R)-5-[5-(1-Methoxy-1-methylethyl)isoxazol-3-yl]-2-methyl-1-{[2-(2H-1,2,3-triazol-2-yl)phenyl]carbonyl}piperidine),
(2-{5-[(3R,6R)-6-Methyl-1-{[2-(2H-1,2,3-triazol-2-yl)phenyl]carbonyl}piperidin-3-yl]isoxazol-3-yl}propan-2-ol),
(2-{5-[(3R,6R)-1-{[2-(Methoxymethyl)phenyl]carbonyl}-6-methylpiperidin-3-yl]isoxazol-3-yl}propan-2-ol),
2-(5-{(3R,6R)-6-Methyl-1-[(2-pyrimidin-2-ylphenyl)carbonyl]piperidin-3-yl}isoxazol-3-yl)propan-2-ol,
2-(5-{(3R,6R)-1-[(2-Ethoxypyridin-3-yl)carbonyl]-6-methylpiperidin-3-yl}isoxazol-3-yl)propan-2-ol,
2-{5-[(3R,6R)-1-{[5-Fluoro-2-(2H-1,2,3-triazol-2-yl)phenyl]carbonyl}-6-methylpiperidin-3-yl]isoxazol-3-yl}propan-2-ol,
2-{5-[(3R,6R)-6-methyl-1-{[3-(1H-pyrazol-1-yl)pyrazin-2-yl]carbonyl}piperidin-3-yl]isoxazol-3-yl}propan-2-ol,
2-{5-[(3R,6R)-1-(Biphenyl-2-ylcarbonyl)-6-methylpiperidin-3-yl]isoxazol-3-yl}propan-2-ol,
2-{5-[(3R,6R)-1-{[5-Chloro-2-(2H-1,2,3-triazol-2-yl)phenyl]carbonyl}-6-methylpiperidin-3-yl]isoxazol-3-yl}propan-2-ol,
2-(5-{(3R,6R)-6-Methyl-1-[(3-pyridin-2-ylpyrazin-2-yl)carbonyl]piperidin-3-yl}isoxazol-3-yl)propan-2-ol,
1-[2-({(2R,5R)-5-[3-(1-Hydroxy-1-methylethyl)isoxazol-5-yl]-2-methylpiperidin-1-yl}carbonyl)phenyl]cyclopropanecarbonitrile,
Methyl 2-({(2R,5R)-5-[3-(1-hydroxy-1-methylethyl)isoxazol-5-yl]-2-methylpiperidin-1-yl}carbonyl)benzoate,
2-(5-{(3R,6R)-1-[(2-Ethoxyphenyl)carbonyl]-6-methylpiperidin-3-yl}isoxazol-3-yl)propan-2-ol
2-{5-[(3R,6R)-6-Methyl-1-{[2-(2H-tetrazol-2-yl)phenyl]carbonyl}piperidin-3-yl]isoxazol-3-yl}propan-2-ol,
2-(5-{(3R,6R)-6-Methyl-1-[(2-phenylpyridin-3-yl)carbonyl]piperidin-3-yl}isoxazol-3-yl)propan-2-ol,
2-(5-{(3R,6R)-6-Methyl-1-[(3-phenylpyridin-2-yl)carbonyl]piperidin-3-yl}isoxazol-3-yl)propan-2-ol,
2-{5-[(3R,6R)-1-{[2-(2,2-Difluoroethoxy)phenyl]carbonyl}-6-methylpiperidin-3-yl]isoxazol-3-yl}propan-2-ol,
2-{5-[(3R,6R)-6-Methyl-1-{[2-(2,2,2-trifluoroethoxy)phenyl]carbonyl}piperidin-3-yl]isoxazol-3-yl}propan-2-ol,
2-(5-{(3R,6R)-6-Methyl-1-[(2-pyrazin-2-ylphenyl)carbonyl]piperidin-3-yl}isoxazol-3-yl)propan-2-ol,
2-{5-[(3R,6R)-1-{[2-(2,2-Difluorocyclopropyl)phenyl]carbonyl}-6-methylpiperidin-3-yl]isoxazol-3-yl}propan-2-ol,
(2-{5-[(3R,6R)-6-Ethyl-1-{[2-(2H-1,2,3-triazol-2-yl)phenyl]carbonyl}piperidin-3-yl]isoxazol-3-yl}propan-2-ol),
((1R)-2,2,2-Trifluoro-1-{5-[(3R,6R)-6-methyl-1-{[2-(2H-1,2,3-triazol-2-yl)phenyl]carbonyl}piperidin-3-yl]isoxazol-3-yl}ethanol),
((1S)-2,2,2-Trifluoro-1-{5-[(3R,6R)-6-methyl-1-{[2-(2H-1,2,3-triazol-2-yl)phenyl]carbonyl}piperidin-3-yl]isoxazol-3-yl}ethanol),
((1R)-2,2,2-Trifluoro-1-{5-[(3R,6R)-6-methyl-1-{[2-(2H-1,2,3-triazol-2-yl)thiophen-3-yl]carbonyl}piperidin-3-yl]isoxazol-3-yl}ethanol), ((1S)-2,2,2-Trifluoro-1-{5-[(3R,6R)-6-methyl-1-{[2-(2H-1,2,3-triazol-2-yl)thiophen-3-yl]carbonyl}piperidin-3-yl]isoxazol-3-yl}ethanol), 1-(2-{[((2R,5R)-2-Methyl-5-{3-[(1R)-2,2,2-Trifluoro-1-hydroxyethyl]isoxazol-5-yl}piperidin-1-yl]carbonyl}phenyl)cyclopropanecarbonitrile, 1-(2-{[((2R,5R)-2-Methyl-5-{3-[(1S)-2,2,2-trifluoro-1-hydroxyethyl]isoxazol-5-yl}piperidin-1-yl]carbonyl}phenyl)cyclopropanecarbonitrile, (1R)-2,2,2-Trifluoro-1-{5-[(3R,6R)-6-methyl-1-{[2-(2H-tetrazol-2-yl)phenyl]carbonyl}piperidin-3-yl]isoxazol-3-yl}ethanol, (1S)-2,2,2-Trifluoro-1-{5-[(3R,6R)-6-methyl-1-{[2-(2H-tetrazol-2-yl)phenyl]carbonyl}piperidin-3-yl]isoxazol-3-yl}ethanol, ((1S)-2,2,2-Trifluoro-1-(5-{(3R,6R)-6-methyl-1-[(2-pyrimidin-2-ylthiophen-3-yl)carbonyl]piperidin-3-yl}isoxazol-3-yl)ethanol), ((1R)-2,2,2-Trifluoro-1-(5-{(3R,6R)-6-methyl-1-[(2-pyrimidin-2-ylthiophen-3-yl)carbonyl]piperidin-3-yl}isoxazol-3-yl)ethanol), ((1R)-2,2,2-Trifluoro-1-(5-{(3R,6R)-6-methyl-1-[(2-pyrimidin-2-ylphenyl)carbonyl]piperidin-3-yl}isoxazol-3-yl)ethanol), ((1S)-2,2,2-Trifluoro-1-(5-{(3R,6R)-6-methyl-1-[(2-pyrimidin-2-ylphenyl)carbonyl]piperidin-3-yl}isoxazol-3-yl)ethanol), (1-Cyclopropyl-1-{5-[(3R,6R)-6-methyl-1-{[2-(2H-1,2,3-triazol-2-yl)phenyl]carbonyl}piperidin-3-yl]isoxazol-3-yl}ethanol), (1-Cyclopropyl-1-{5-[(3R,6R)-6-methyl-1-{[2-(2H-1,2,3-triazol-2-yl)phenyl]carbonyl}piperidin-3-yl]isoxazol-3-yl}ethanol), 2-{5-[(3R,6R)-6-Methyl-1-{[2-(2H-1,2,3-triazol-2-yl)phenyl]carbonyl}piperidin-3-yl]isoxazol-3-yl}butan-2-ol, 2-{5-[(3R,6R)-6-Methyl-1-{[2-(2H-1,2,3-triazol-2-yl)phenyl]carbonyl}piperidin-3-yl]isoxazol-3-yl}butan-2-ol, ((2R,5R)-2-Methyl-5-[3-(tetrahydrofuran-2-yl)isoxazol-5-yl]-1-{[2-(2H-1,2,3-triazol-2-yl)phenyl]carbonyl}piperidine), ((2R,5R)-5-[3-(1-Methoxy-1-methylethyl)isoxazol-5-yl]-2-methyl-1-{[2-(2H-1,2,3-triazol-2-yl)phenyl]carbonyl}piperidine), (2-{3-[(3R,6R)-6-Methyl-1-{[2-(2H-1,2,3-triazol-2-yl)phenyl]carbonyl}piperidin-3-yl]isothiazol-5-yl}propan-2-ol}piperidine), (2-{3-[(3R,6R)-6-Methyl-1-{[2-(2H-1,2,3-triazol-2-yl)thiophen-3-yl]carbonyl}piperidin-3-yl]isothiazol-5-yl}propan-2-ol), 2-{3-[(3R,6R)-6-Methyl-1-{[2-(2H-tetrazol-2-yl)phenyl]carbonyl}piperidin-3-yl]isothiazol-5-yl}propan-2-ol, 2-{3-[(3R,6R)-1-{[4-Fluoro-2-(2H-1,2,3-triazol-2-yl)phenyl]carbonyl}-6-methylpiperidin-3-yl]isothiazol-5-yl}propan-2-ol, 1-[2-({(2R,5R)-5-[5-(1-Hydroxy-1-methylethyl)isothiazol-3-yl]-2-methylpiperidin-1-yl}carbonyl)phenyl]cyclopropanecarbonitrile, 2-(3-{(3R,6R)-6-Methyl-1-[(2-pyrimidin-2-ylphenyl)carbonyl]piperidin-3-yl}isothiazol-5-yl)propan-2-ol, (2-(3-{(3R,6R)-6-Methyl-1-[(2-pyrimidin-2-ylthiophen-3-yl)carbonyl]piperidin-3-yl}isothiazol-5-yl)propan-2-ol), 2-(3-{(3R,6R)-6-Methyl-1-[(4-pyrimidin-2-ylthiophen-3-yl)carbonyl]piperidin-3-yl}isothiazol-5-yl)propan-2-ol, 2-{3-[(3R,6R)-6-Methyl-1-{[4-(2H-1,2,3-triazol-2-yl)thiophen-3-yl]carbonyl}piperidin-3-yl]isothiazol-5-yl}propan-2-ol, Methyl 2-({(2R,5R)-5-[5-(1-hydroxy-1-methylethyl)isothiazol-3-yl]-2-methylpiperidin-1-yl}carbonyl)benzoate, 2-{3-[(3R,6R)-6-Methyl-1-{[2-(trifluoromethoxy)phenyl]carbonyl}piperidin-3-yl]isothiazol-5-yl}propan-2-ol, 2-{3-[(3R,6R)-1-{[2-(2,2-Difluoroethoxy)pyridin-3-yl]carbonyl}-6-methylpiperidin-3-yl]isothiazol-5-yl}propan-2-ol, and 2-{3-[(3R,6R)-1-{[2-(2-methoxyethyl)phenyl]carbonyl}-6-methylpiperidin-3-yl]isothiazol-5-yl}propan-2-ol;

or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Formula I shows the structure of the class of compounds without specific stereochemistry.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl, and hexyl. A group which is designated as being independently substituted with substituents may be independently substituted with multiple numbers of such substituents. The term "heterocycle" as used herein includes both unsaturated and saturated heterocyclic moieties, wherein the unsaturated heterocyclic moieties (i.e. "heteroaryl") include benzoimidazolyl, benzimidazolonyl, benzofuranyl, benzofurazanyl, benzopyrazolyl, benzothiazolyl, benzotriazolyl, benzothiophenyl, benzoxazepin, benzoxazolyl, carbazolyl, carbolinyl, cinnolinyl, furanyl, imidazolyl, indolinyl, indolyl, dihydroindolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydroquinoxalinyl, tetrazolyl, tetrazolopyridyl, thiadiazolyl, thiazolyl, thienyl, triazolyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof.

The present invention also includes all pharmaceutically acceptable isotopic variations of a compound of the Formula I in which one or more atoms is replaced by atoms having the same atomic number, but an atomic mass or mass number different from the atomic mass or mass number usually found in nature. Examples of isotopes suitable for inclusion in the compounds of the invention include isotopes of hydrogen such as $^2H$ and $^3H$, carbon such as $^{11}C$, $^{13}C$ and $^{14}C$, nitrogen such as $^{13}N$ and $^{15}N$, oxygen such as $^{15}O$, $^{17}O$ and $^{18}O$, phosphorus such as $^{32}P$, sulfur such as $^{35}S$, fluorine such as $^{18}F$, iodine such as $^{123}I$ and $^{125}I$, and chlorine such as $^{36}Cl$. Certain isotopically-labelled compounds of Formula I, for example those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labelled compounds of Formula I can generally be prepared by conventional techniques known to those skilled in the art or by processes analogous to those described in the accompanying Examples using appropriate isotopically-labelled reagents in place of the non-labelled reagent previously employed.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which is selected from the group consisting of the compounds disclosed in the following Examples and pharmaceutically acceptable salts thereof and individual enantiomers or diastereomers thereof.

The present invention is also directed to the use of the compounds disclosed herein as antagonists of orexin receptor activity. The subject compounds, and pharmaceutically acceptable salts thereof, are useful in a method of antagonizing orexin receptor activity in a subject, such as a mammal, comprising the administration of an amount of the compound. In addition to primates, especially humans, a variety of other mammals may be administered with a compound of the present invention. The present invention is directed to a compound of the present invention or a pharmaceutically acceptable salt thereof that could be useful in therapy. The present invention may further be directed to a use of a compound of the present invention or a pharmaceutically acceptable salt thereof for the manufacture of a medicament for antagonizing orexin receptor activity or treating the disorders and diseases noted herein in humans and animals.

A subject administered with a compound of the present invention, or a pharmaceutically acceptable salt thereof, is generally a mammal, such as a human being, male or female. The amount of compound administered to the subject is an amount sufficient to antagonize the Orexin receptor in the subject. In an embodiment, the amount of compound can be an "effective amount", wherein the subject compound is administered in an amount that will elicit the biological or medical response of a tissue, system, animal or human that is being sought by the researcher, veterinarian, medical doctor or other clinician. An effective amount does not necessarily include considerations of toxicity and safety related to the administration of the compound. It is recognized that one skilled in the art may affect neurological and psychiatric disorders associated with Orexin receptor activation by treating a subject presently afflicted with the disorders, or by prophylactically treating a subject likely to be afflicted with the disorders, with an effective amount of a compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a subject that is predisposed to such disease or disorder. The terms "administration of" and or "administering a" compound should be understood to mean providing a compound of the invention or a prodrug of a compound of the invention to the subject.

The term "composition" as used herein is intended to encompass a product comprising the specified ingredients in the specified amounts, as well as any product which results, directly or indirectly, from combination of the specified ingredients in the specified amounts. Such term is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as orexin receptor OX1R and/or OX2R antagonists may be readily determined without undue experimentation by methodology well known in the art, including the "FLIPR $Ca^{2+}$ Flux Assay" (Okumura et al., Biochem. Biophys. Res. Comm. 280:976-981, 2001). In a typical experiment the OX1 and OX2 receptor antagonistic activity of the compounds of the present invention was determined in accordance with the following experimental method. For intracellular calcium measurements, Chinese hamster ovary (CHO) cells expressing the rat orexin-1 receptor or the human orexin-2 receptor, are grown in Iscove's modified DMEM containing 2 mM L-glutamine, 0.5 g/ml G418, 1% hypoxanthine-thymidine supplement, 100 U/ml penicillin, 100 µg/ml streptomycin and 10% heat-inactivated fetal calf serum (FCS). The cells are seeded at 20,000 cells/well into Becton-Dickinson black 384-well clear bottom sterile plates coated with poly-D-lysine. All reagents are from GIBCO-Invitrogen Corp. The seeded plates are incubated overnight at 37° C. and 5% $CO_2$. Ala-6,12 human orexin-A as the agonist is prepared as a 1 mM stock solution in 1% bovine serum albumin (BSA) and diluted in assay buffer (HBSS containing 20 mM HEPES, 0.1% BSA and 2.5 mM probenecid, pH7.4) for use in the assay at a final concentration of 70 pM. Test compounds are prepared as 10 mM stock solution in DMSO, then diluted in 384-well plates, first in DMSO, then assay buffer. On the day of the assay, cells are washed 3 times with 100 µl assay buffer and then incubated for 60 min (37° C., 5% $CO_2$) in 60 µl assay buffer containing 1 µM Fluo-4AM ester, 0.02% pluronic acid, and 1% BSA. The dye loading solution is then aspirated and cells are washed 3 times with 100 µl assay buffer. 30 µl of that same buffer is left in each well. Within the Fluorescent Imaging Plate Reader (FLIPR, Molecular Devices), test compounds are added to the plate in a volume of 25 µl, incubated for 5 min and finally 25 µl of agonist is added. Fluorescence is measured for each well at 1 second intervals for 5 minutes and the height of each fluorescence peak is compared to the height of the fluorescence peak induced by 70 pM Ala-6,12 orexin-A with buffer in place of antagonist. For each antagonist, $IC_{50}$ value (the concentration of compound needed to inhibit 50% of the agonist response) is determined. Alternatively, compound potency can be assessed by a radioligand binding assay (described in Bergman et. al. Bioorg. Med. Chem. Lett. 2008, 18, 1425-1430) in which the inhibition constant ($K_i$) is determined in membranes prepared from CHO cells expressing either the OX1 or OX2 receptor. The intrinsic orexin receptor antagonist activity of a compound which may be used in the present invention may be determined by these assays.

All of the final compounds of the following examples had activity in the FLIPR assay with an $IC_{50}$ of about 5 nM to 2500 nM against the orexin-2 receptor. Additional data is provided in the following Examples. Such a result is indicative of the intrinsic activity of the compounds in use as antagonists of orexin-1 receptor and/or the orexin-2 receptor. In general, one of ordinary skill in the art would appreciate that a substance is considered to effectively antagonize the orexin receptor if it has an $IC_{50}$ of less than about 50 µM, preferably less than about 1000 nM.

The orexin receptors have been implicated in a wide range of biological functions. This has suggested a potential role for these receptors in a variety of disease processes in humans or other species. The compounds of the present invention could therefore potentially have utility in treating, preventing, ameliorating, controlling or reducing the risk of a variety of neurological and psychiatric disorders associated with orexin receptors, including one or more of the following conditions or diseases: sleep disorders, sleep disturbances, including enhancing sleep quality, improving sleep quality, increasing sleep efficiency, augmenting sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent wakings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia, hypersomnia, idiopathic hypersomnia, repeatability hypersomnia, intrinsic hypersomnia, narcolepsy, interrupted sleep, sleep apnea, wakefulness, nocturnal myoclonus, REM sleep interruptions, jet-lag, shift workers' sleep disturbances, dyssomnias, night terror, insomnias associated with depression, emotional/mood disorders, Alzheimer's disease or cognitive impairment, as well as sleep walking and enuresis, and sleep disorders which accompany aging; Alzheimer's sundowning; conditions associated with circadian rhythmicity as well as mental and physical disorders associated with travel across time zones and with rotating shift-work schedules, conditions due to drugs which cause reductions in REM sleep as a side effect; fibromyalgia; syndromes which are manifested by non-restorative sleep and muscle pain or sleep apnea which is associated with respiratory disturbances during sleep; conditions which result from a diminished quality of sleep; increasing learning; augmenting memory; increasing retention of memory; eating disorders associated with excessive food intake and complications associated therewith, compulsive eating disorders, obesity (due to any cause, whether genetic or environmental), obesity-related disorders overeating, anorexia, bulimia, cachexia, dysregulated appetite control, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, lung disease, abnormal heart rhythms and arrythmias, myocardial infarction, congestive heart failure, coronary heart disease, acute and congestive heart failure; hypotension; hypertension; urinary retention; osteoporosis; angina pectoris; myocardinal infarction; ischemic or haemorrhagic stroke; subarachnoid haemorrhage; ulcers; allergies; benign prostatic hypertrophy; chronic renal failure; renal disease; impaired glucose tolerance; sudden death, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia, metabolic syndrome, also known as syndrome X, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, intestinal motility dyskinesias, obesity-related gastro-esophageal reflux, hypothalmic diseases, hypophysis diseases, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, hyperuricaemia, lower back pain, gallbladder disease, gout, kidney cancer, increased anesthetic risk, reducing the risk of secondary outcomes of obesity, such as reducing the risk of left ventricular hypertrophy; diseases or disorders where abnormal oscillatory activity occurs in the brain, including depression, migraine, neuropathic pain, Parkinson's disease, psychosis and schizophrenia, as well as diseases or disorders where there is abnormal coupling of activity, particularly through the thalamus; enhancing cognitive function, including cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders; enhancing memory; increasing memory retention; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure; conditions of the genital/urinary system; disorders of sexual function and fertility; adequacy of renal function; responsivity to anesthetics; mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; affective neurosis; depressive neurosis; anxiety neurosis; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea, Huntington's disease and Tourette syndrome; Cushing's syndrome/disease; basophile adenoma; prolactinoma; hyperprolactinemia; hypophysis tumor/adenoma; hypothalamic diseases; inflammatory bowel disease; gastric diskinesia; gastric ulcers; Froehlich's syndrome; adrenohypophysis disease; hypophysis disease; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions, seizure disorders, absence seizures, complex partial and generalized seizures; Lennox-Gastaut syndrome; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; dissociateive disorders including multiple personality syndromes and psychogenic amnesias; substance-related disorders, substance use, substance abuse, substance seeking, substance reinstatement, all types of psychological and physical addictions and addictive behaviors, reward-related behaviors (including substance-induced delirium, persisting dementia, persisting amnestic disorder, psychotic disorder or anxiety disorder; tolerance, addictive feeding, addictive feeding behaviors, binge/purge feeding behaviors, dependence, withdrawal or relapse from substances including alcohol, amphetamines, cannabis, cocaine, hallucinogens, inhalants, morphine, nicotine, opioids, phencyclidine, sedatives, hypnotics or anxiolytics); appetite, taste, eating or drinking disorders; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); neurodegenerative disorders including nosological entities such as disinhibition-dementia-parkinsonism-amyotrophy complex; pallido-ponto-nigral degeneration; epilepsy; seizure disorders; attention deficit/hyperactivity disorder (ADHD); conduct disorder; migraine (including migraine headache); headache; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; gastric dyskinesia; gastric ulcers; Kallman's syndrome (anosmia); asthma; cancer; conditions associated with visceral pain such as irritable bowel syndrome, and angina; eating disorders; urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache and other diseases related to general orexin system dysfunction.

Thus, in certain embodiments the present invention may provide methods for: enhancing the quality of sleep; augmenting sleep maintenance; increasing REM sleep; increasing stage 2 sleep; decreasing fragmentation of sleep patterns; treating insomnia and all types of sleep disorders; treating or controlling sleep disturbances associated with diseases such as neurological disorders including neuropathic pain and restless leg syndrome; treating or controlling addiction disorders; treating or controlling psychoactive substance use and abuse; enhancing cognition; increasing memory retention; treating or controlling obesity; treating or controlling diabetes and appetite, taste, eating, or drinking disorders; treating or controlling hypothalamic diseases; treating or controlling depression; treating, controlling, ameliorating or reducing the risk of epilepsy, including absence epilepsy; treating or controlling pain, including neuropathic pain; treating or controlling Parkinson's disease; treating or controlling psychosis; treating or controlling dysthymic, mood, psychotic and anxiety disorders; treating or controlling depression, including major depression and major depression disorder; treating or controlling bipolar disorder; or treating, controlling, ameliorating or reducing the risk of schizophrenia, in a mammalian subject in need thereof which comprises administering to the subject an effective amount of a compound of the present invention.

The subject compounds could further be of potential use in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to subjects (animals and human) in need of such treatment in dosages that will provide optimal pharmaceutical efficacy. The selected dosage depends upon the desired therapeutic effect, on the route of administration, and on the duration of the treatment. The dose will vary from subject to subject depending upon the nature and severity of disease, the subject's weight, special diets then being followed by a subject, concurrent medication, and other factors which those skilled in the art will recognize. Generally, dosage levels of between 0.0001 to 10 mg/kg. of body weight daily are administered to the subject, e.g., humans and elderly humans, to obtain effective antagonism of orexin receptors. The dosage range will generally be about 0.5 mg to 1.0 g. per subject per day which may be administered in single or multiple doses. In one embodiment, the dosage range will be about 0.5 mg to 500 mg per subject per day; in another embodiment about 0.5 mg to 200 mg per subject per day; and in yet another embodiment about 5 mg to 50 mg per subject per day. Compositions of the present invention may be provided in a solid dosage formulation such as comprising about 0.5 mg to 500 mg active ingredient, or comprising about 1 mg to 250 mg active ingredient. The composition may be provided in a solid dosage formulation comprising about 1 mg, 5 mg, 10 mg, 25 mg, 30 mg, 50 mg, 80 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the subject to be treated. The compounds may be administered on a regimen of 1 to 4 times per day, such as once or twice per day. The compounds may be administered before bedtime. For example, the compounds may be administered about 1 Hour prior to bedtime, about 30 minutes prior to bedtime or immediately before bedtime.

The compounds of the present invention may be used in combination with one or more other active agents. In one embodiment, the combination of the active agents together is safer or more effective than either agent alone. Such other active agent(s) may be administered, by a route and in an amount commonly used therefor, contemporaneously or sequentially with a compound of the present invention. When a compound of the present invention is used contemporaneously with one or more other active agents, a composition in unit dosage form containing such other active agents and the compound of the present invention is contemplated. However, the combination therapy may also include therapies in which the compound of the present invention and one or more other active agents are administered on different overlapping schedules. It is also contemplated that when used in combination with one or more other active ingredients, the compounds of the present invention and the other active ingredients may be used in lower doses than when each is used singly. Accordingly, the compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other active agents that are used in the prevention, treatment, control, amelioration, or reduction of risk of the diseases or conditions for which compounds of the present invention are useful. Such other active agents may be administered, by a route and in an amount commonly used therefor, contemporaneously or sequentially with a compound of the present invention. When a compound of the present invention is used contemporaneously with one or more other active agents, a composition containing such other active agents in addition to the compound of the present invention is contemplated. Accordingly, the compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be administered in combination with other compounds which are known in the art to be useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, ornortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the subject compound may be employed in combination with other compounds which are known in the art, either administered separately or in the same compositions, including, but are not limited to: insulin sensitizers including (i) PPARγ antagonists such as glitazones (e.g. ciglitazone; darglitazone; englitazone; isaglitazone (MCC-555); pioglitazone; rosiglitazone; troglitazone; tularik; BRL49653; CLX-0921; 5-BTZD), GW-0207, LG-100641, and LY-300512, and the like); (iii) biguanides such as metformin and phenformin; (b) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-NH$_2$); (c) sulfonylureas, such as acetohexamide; chlorpropamide; diabinese; glibenclamide; glipizide; glyburide; glimepiride; gliclazide; glipentide; gliquidone; glisolamide; tolazamide; and tolbutamide; (d) α-glucosidase inhibitors, such as acarbose, adiposine; camiglibose; emiglitate; miglitol; voglibose; pradimicin-Q; salbostatin; CKD-711; MDL-25,637; MDL-73,945; and MOR 14, and the like; (e) cholesterol lowering agents such as (i) HMG-CoA reductase inhibitors (atorvastatin, itavastatin, fluvastatin, lovastatin, pravastatin, rivastatin, rosuvastatin, simvastatin, and other statins), (ii) bile acid absorbers/sequestrants, such as cholestyramine, colestipol, dialkylaminoalkyl derivatives of a cross-linked dextran; Colestid®; LoCholest®, and the like, (ii) nicotinyl alcohol, nicotinic acid or a salt thereof, (iii) proliferator-activater receptor a agonists such as fenofibric acid derivatives (gemfibrozil, clofibrate, fenofibrate and benzafibrate), (iv) inhibitors of cholesterol absorption such as stanol esters, beta-sitosterol, sterol glycosides such as tiqueside; and azetidinones such as ezetimibe, and the like, and (acyl CoA:cholesterol acyltransferase (ACAT)) inhibitors such as avasimibe, and melinamide, (v) anti-oxidants, such as probucol, (vi) vitamin E, and (vii) thyromimetics; (f) PPARα agonists such as beclofibrate, benzafibrate, ciprofibrate, clofibrate, etofibrate, fenofibrate, and gemfibrozil; and other fibric acid derivatives, such as Atromid®, Lopid® and Tricor®, and the like, and PPARα agonists as described in WO 97/36579; (g) PPARδ agonists, such as those disclosed in WO97/28149; (h) PPAR α/δ agonists, such as muraglitazar, and the compounds disclosed in U.S. Pat. No. 6,414,002; (i) anti-obesity agents, such as (1) growth hormone secretagogues, growth hormone secretagogue receptor agonists/antagonists, such as NN703, hexarelin, MK-0677, SM-130686, CP-424,391, L-692,429, and L-163,255, and such as those disclosed in U.S. Pat. Nos. 5,536,716, and 6,358,951, U.S. Patent Application Nos. 2002/049196 and 2002/022637, and PCT Application Nos. WO 01/56592 and WO 02/32888; (2) protein tyrosine phosphatase-1B (PTP-1B) inhibitors; (3) cannabinoid receptor ligands, such as cannabinoid CB$_1$ receptor antagonists or inverse agonists, such as rimonabant, taranabant, AMT-251, and SR-14778 and SR 141716A (Sanofi Synthelabo), SLV-319 (Solvay), BAY 65-2520 (Bayer) and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, WO 01/64632, WO 01/64633, WO 01/64634, WO02/076949, WO 03/007887, WO 04/048317, and WO 05/000809; (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A; (6) pancreatic lipase inhibitors, such as orlistat (Xenical®), Triton WR1339, RHC80267, lipstatin, tetrahydrolipstatin, teasaponin, diethylumbelliferyl phosphate, and those disclosed in PCT Application No. WO 01/77094; (7) neuropeptide Y1 antagonists, such as BIBP3226, J-115814, BIBO 3304, LY-357897, CP-671906, GI-264879A, and those disclosed in U.S. Pat. No. 6,001,836, and PCT Patent Publication Nos. WO 96/14307, WO 01/23387, WO 99/51600, WO 01/85690, WO 01/85098, WO 01/85173, and WO 01/89528; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,057,335; 6,043,246; 6,140,354; 6,166,038; 6,180,653; 6,191,160; 6,313,298; 6,335,345; 6,337,332; 6,326,375; 6,329,395; 6,340,683; 6,388,077; 6,462,053; 6,649,624; and 6,723,847, European Patent Nos. EP-01010691, and EP-01044970; and PCT International Patent Publication Nos. WO 97/19682, WO 97/20820, WO 97/20821, WO 97/20822, WO 97/20823, WO 98/24768; WO 98/25907; WO 98/25908; WO 98/27063, WO 98/47505; WO 98/40356; WO 99/15516; WO 99/27965; WO 00/64880, WO 00/68197, WO 00/69849, WO 01/09120, WO 01/14376; WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; WO 02/094825; WO 03/014083; WO 03/10191; WO 03/092889; WO 04/002986; and WO 04/031175; (9) melanin-concentrating hormone (MCH) receptor antagonists, such as those disclosed in WO 01/21577 and WO 01/21169; (10) melanin-concentrating hormone 1 receptor (MCH1R) antagonists, such as T-226296 (Takeda), and those disclosed in PCT Patent Application Nos. WO 01/82925, WO 01/87834, WO 02/051809, WO 02/06245, WO 02/076929, WO 02/076947, WO 02/04433, WO 02/51809, WO 02/083134, WO 02/094799, WO 03/004027; (11) melanin-concentrating hormone 2 receptor (MCH2R) agonist/antagonists; (12) orexin receptor antagonists, such as SB-334867-A, and those disclosed in patent publications herein; (13) serotonin reuptake inhibitors such as fluoxetine, paroxetine, and sertraline; (14) melanocortin agonists, such as Melanotan II; (15) Mc4r (melanocortin 4 receptor) agonists, such as CHIR86036 (Chiron), ME-10142, and ME-10145 (Melacure), CHIR86036 (Chiron); PT-141, and PT-14 (Palatin); (16) 5HT-2 agonists; (17) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (18) galanin antagonists; (19) CCK agonists; (20) CCK-A (cholecystokinin-A) agonists, such as AR-R 15849, GI 181771, JMV-180, A-71378, A-71623 and SR14613, and those described in U.S. Pat. No. 5,739,106; (21) GLP-1 agonists; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and O-[3-(1H-imidazol-4-yl)propanol]-carbamates; (25) β-hydroxy steroid dehydrogenase-1 inhibitors (β-HSD-1); (26) PDE (phosphodiesterase) inhibitors, such as theophylline, pentoxifylline, zaprinast, sildenafil, amrinone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists, such as those disclosed in PCT Application Nos. WO 01/87335, and WO 02/08250; (30) leptin, including recombinant human leptin (PEG-OB, Hoffman La Roche) and recombinant methionyl human leptin (Amgen); (31) leptin derivatives; (32) BRS3 (bombesin receptor subtype 3) agonists such as [D-Phe6, beta-Ala11,Phe13,Nle14]Bn(6-14) and [D -Phe6,Phe13]Bn (6-13)propylamide, and those compounds disclosed in Pept. Sci. 2002 August; 8(8): 461-75); (33) CNTF (Ciliary neurotrophic factors), such as GI-181771 (Glaxo-SmithKline), SR146131 (Sanofi Synthelabo), butabindide, PD170,292, and PD 149164 (Pfizer); (34) CNTF derivatives, such as axokine (Regeneron); (35) monoamine reuptake inhibitors, such as sibutramine; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl] benzoic acid (TTNPB), retinoic acid; (37) thyroid hormone β agonists, such as KB-2611 (KaroBioBMS); (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444, sitagliptin; and the compounds disclosed in U.S. Pat. No. 6,699,871, WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181; (46) dicarboxylate transporter inhibitors; (47) glucose transporter inhibitors; (48) phosphate transporter inhibitors; (49) Metformin (Glucophage®); (50) Topiramate (Topimax®); (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)); (51) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (52) Neuropeptide Y4 (NPY4) agonists such as pancreatic peptide (PP), and other Y4 agonists such as 1229U91; (54) cyclooxygenase-2 inhibitors such as etoricoxib, celecoxib, valdecoxib, parecoxib, lumiracoxib, BMS347070, tiracoxib or JTE522, ABT963, CS502 and GW406381; (55) Neuropeptide Y1 (NPY1) antagonists such as BIBP3226, J-115814, BIBO 3304, LY-357897, CP-671906, GI-264879A; (56) Opioid antagonists such as nalmefene (Revex®), 3-methoxynaltrexone, naloxone, naltrexone; (57) 11β HSD-1 (11-beta hydroxy steroid dehydrogenase type 1) inhibitors such as BVT 3498, BVT 2733, and those disclosed in WO 01/90091, WO 01/90090, WO 01/90092, U.S. Pat. No. 6,730,690 and US 2004-0133011; (58) aminorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70) N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) phenmetrazine; (86) picilorex; (87) phytopharm 57; and (88) zonisamide, (89) neuromedin U and analogs or derivatives thereof, (90) oxyntomodulin and analogs or derivatives thereof, and (91) Neurokinin-1 receptor antagonists (NK-1 antagonists) such as the compounds disclosed in: U.S. Pat. Nos. 5,162,339, 5,232,929, 5,242,930, 5,373,003, 5,387, 595, 5,459,270, 5,494,926, 5,496,833, and 5,637,699.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-$HT_{1A}$ agonists or antagonists, especially 5-$HT_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; citalopram, duloxetine, fluoxetine, fluvoxamine, paroxetine and sertraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the subject compound may be employed in combination with anti-Alzheimer's agents; beta-secretase inhibitors; gamma-secretase inhibitors; growth hormone secretagogues; recombinant growth hormone; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine $H_3$ antagonists; AMPA agonists; PDE IV inhibitors; GABAA inverse agonists; or neuronal nicotinic agonists.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chlordiazepoxide, clomipramine, clonazepam, cloperidone, clorazepate, clorethate, clozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, venlafaxine, zaleplon, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole.

In another embodiment, the subject compound may be employed in combination with acetophenazine, alentemol, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene or trifluoperazine.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone.

In another embodiment, the subject compound may be employed in combination with a nicotine agonist or a nicotine receptor partial agonist such as varenicline, opioid antagonists (e.g., naltrexone (including naltrexone depot), antabuse, and nalmefene), dopaminergic agents (e.g., apomorphine), ADD/ADHD agents (e.g., methylphenidate hydrochloride (e.g., Ritalin® and Concerta®), atomoxetine (e.g., Strattera®), a monoamine oxidase inhibitor (MAOI), amphetamines (e.g., Adderall®)) and anti-obesity agents, such as apo-B/MTP inhibitors, 11Beta-hydroxy steroid dehydrogenase-1 (11Beta-HSD type 1) inhibitors, peptide YY3-36 or analogs thereof, MCR-4 agonists, CCK-A agonists, monoamine reuptake inhibitors, sympathomimetic agents, β3 adrenergic receptor agonists, dopamine receptor agonists, melanocyte-stimulating hormone receptor analogs, 5-HT2c receptor agonists, melanin concentrating hormone receptor antagonists, leptin, leptin analogs, leptin receptor agonists, galanin receptor antagonists, lipase inhibitors, bombesin receptor agonists, neuropeptide-Y receptor antagonists (e.g., NPY Y5 receptor antagonists), thyromimetic agents, dehydroepiandrosterone or analogs thereof, glucocorticoid receptor antagonists, other orexin receptor antagonists, glucagon-like peptide-1 receptor agonists, ciliary neurotrophic factors, human agouti-related protein antagonists, ghrelin receptor antagonists, histamine 3 receptor antagonists or inverse agonists, and neuromedin U receptor agonists, and pharmaceutically acceptable salts thereof.

In another embodiment, the subject compound may be employed in combination with an anoretic agent such as aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; selective serotonin reuptake inhibitor (SSRI); halogenated amphetamine derivatives, including chlorphentermine, cloforex, clortermine, dexfenfluramine, fenfluramine, picilorex and sibutramine; and pharmaceutically acceptable salts thereof.

In another embodiment, the subject compound may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention may be effective for use in humans.

The compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the compositions are prepared by uniformly and intimately bringing the active ingredient into association with a liquid carrier or a finely divided solid carrier or both, and then, if necessary, shaping the product into the desired formulation. In the composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Compositions intended for oral use may be prepared according to any method known to the art for the manufacture of compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art (e.g. PCT Patent Publications WO2001/68609, WO2004/085403, WO2005/118548, WO2008/147518, WO2009/143033 and WO2010/048012) or as illustrated herein. The following abbreviations are used herein: Me: methyl; Et: ethyl; t-Bu: tert-butyl; Ar: aryl; Ph:

phenyl; Bn: benzyl; Ac: acetyl; Boc: tert-butyloxy carbonyl; BSA: bovine serum albumin; CbzCl: benzylchloroformate; CDI: carbonyl diimidazole; DCM: dichloromethane; DCE: dichloroethane; DEAD: diethylazodicarboxylate; DIPEA: N,N-diisopropylethylamine; DMF: N,N-dimethylformamide; DMSO: dimethylsulfoxide; $CH_2Cl_2$: dichloromethane; EDC: N-(3-Dimethylaminopropyl)-N'-ethylcarbodiimide; $Et_3N$: triethylamine; EtOAc: ethylacetate; EtOH: ethanol; HCl: hydrogen chloride; HATU: (O-(7-azabenzotriazol-1-yl)-N,N,N',N'-tetramethyluronium hexafluorophosphate); HOAt: 1-hydroxy-7-aza-benzotriazole; HOBT: hydroxybenzotriazole hydrate; HPLC: high performance liquid chromatography; Hunig's base: N,N-diisopropylethylamine; MeOH: methanol; $MgSO_4$: magnesium sulfate; MTBE: methyl tert-butyl ether; $NaHCO_3$: sodium bicarbonate; NaOH: sodium hydroxide; NMM: N-methylmorpholine; PyClu: 1-(chloro-1-pyrrolidinylmethylene)-pyrrolidinium hexafluorophosphate; rt: room temperature; $SOCl_2$: thionyl chloride; T3P: 2,4,6-tripropyl-1,3,5,2,4,6-trioxatriphosphorinane-2,4,6-trioxide; THF: tetrahydrofuran; TFA: trifluoracetic acid. The compounds of the present invention can be prepared in a variety of fashions.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

GENERAL SYNTHETIC SCHEMES

In a general method to prepare the compounds of the current invention, the amine of a piperidinemethanol derivative A is protected with an appropriate protecting group, for example BOC. The alcohol is then oxidized to the acid via either one or two step procedures. Coupling of the resulting acid C with bromoethylamine can then be affected by an appropriate coupling reagent. Oxidation/bromination then affords protected compound E which can then be deprotected and then piperidine F coupled with the desired acid to form amide G. The bromo group is then amenable to a range of further transformations to other functional groups, either by modification of final product G, or of intermediate E.

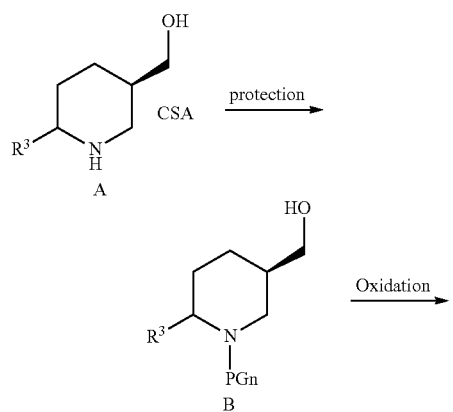

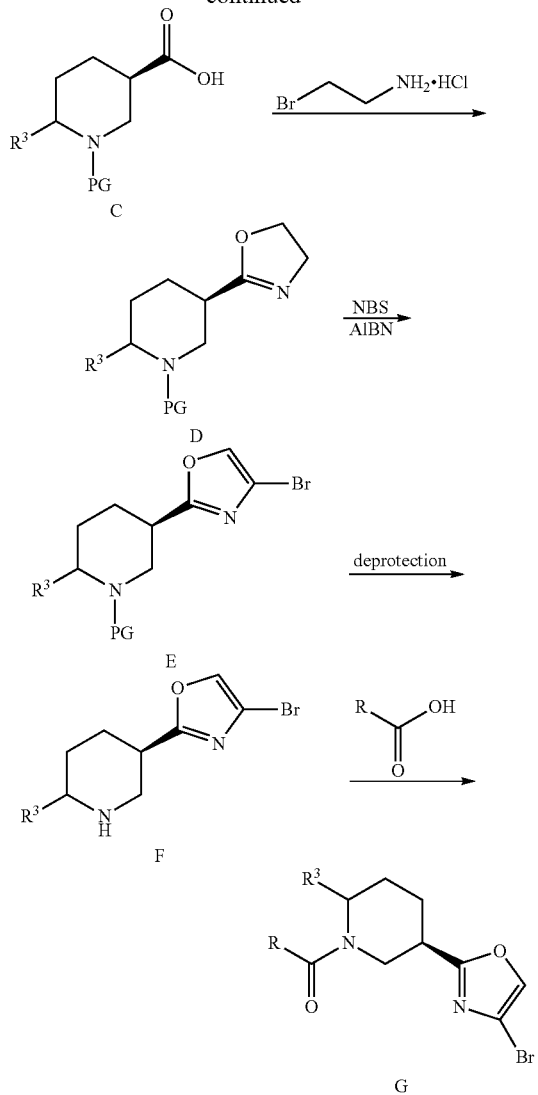

In another general method to prepare the compounds of the current invention, an amide or carbamate derivative of the piperidine H is oxidized to the corresponding acid in either a one or two step oxidation process. Coupling of the resulting acid J with aminomalononitrile results in coupling and cyclization to aminooxazole derivative K. Diazotization and bromination of K affords intermediate L. The cyano and bromo substituents can then be converted to other substituents of interest by a range of appropriate chemistry. In the case where chemistry was carried out on a carbamate derivative of the piperidine, the carbamate can be removed under appropriate conditions and the resulting piperidine coupled with the desired acid reagent under appropriate coupling conditions.

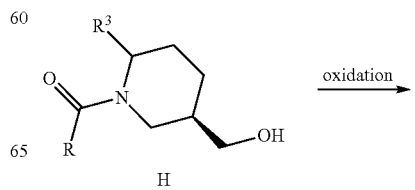

37

-continued

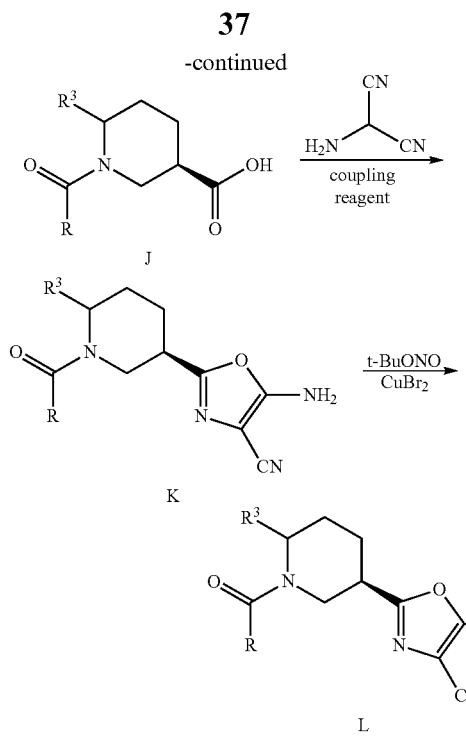

In another general method to prepare the compounds of the current invention, an acid intermediate J can be coupled with an amino substituted keto ester to provide intermediate M. Dehydrative cyclization of this intermediate with for example, triphenylphosphine iodine or triphenylphosphine hexachloroethane affords intermediate N. The ester functionality in intermediate N can then be converted to other functionality, for example secondary of tertiary alcohols via standard processes described in the literature.

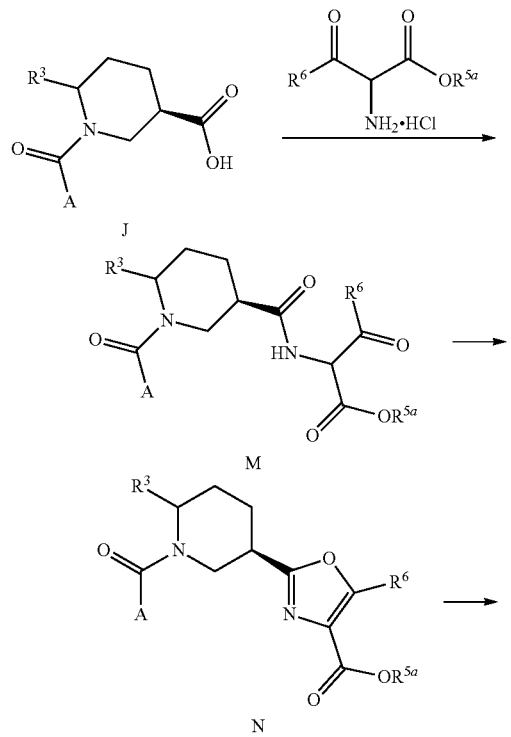

38

-continued

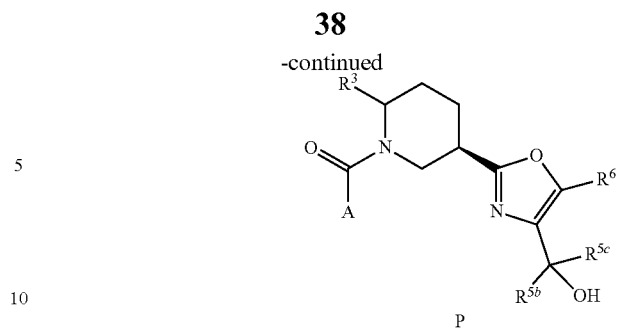

In another general method to prepare the compounds of the current invention, an amide or carbamate derivative of a piperidine aldehyde Q is reacted with an aminoethanol derivative and the resulting dihydrooxazole derivative R aromatized with an appropriate oxidant, such as IBX in DMSO. The resulting intermediate N can be further functionalized as described in the scheme above.

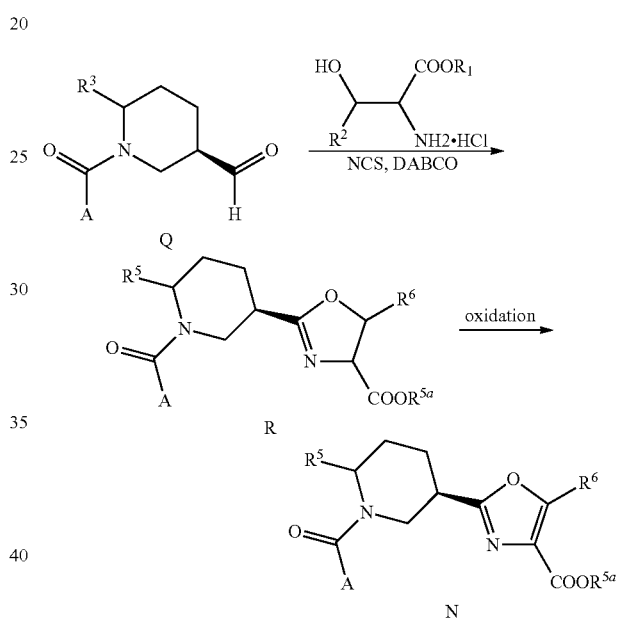

INTERMEDIATES

Intermediate A

Preparation of 2-(2,2-Difluoroethoxy)nicotinic Acid

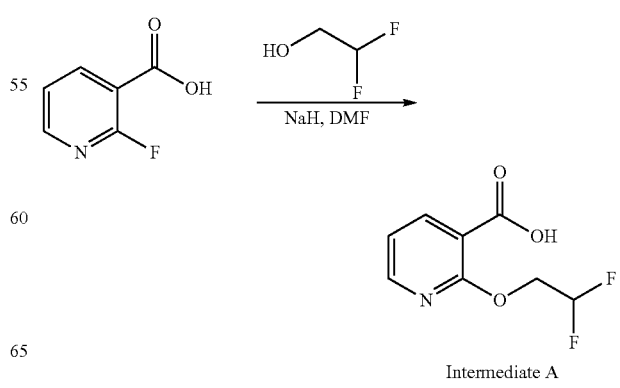

Intermediate A

To a suspension of 2,2-difluoroethanol (492 mg, 6.0 mmol) in DMF (10 mL) at 0° C. was added NaH (180 mg, 4.5 mmol), and the mixture was stirred at 0° C. for 0.5 h. A suspension of 2-fluoronicotinic acid (423 mg, 3.0 mmol) and NaH (180 mg, 4.5 mmol) in DMF (5 mL) was added dropwise at 0° C. and the resulting mixture stirred at RT overnight. The mixture was diluted with water, acidified to pH~3 with 1M HCl and extracted with EtOAc (50 mL×3). The combined organic layers were washed with brine, dried over MgSO$_4$, filtered, and concentrated in vacuo to give the crude product 2 which was used directly without any further purification. LRMS m/z (M+H) 204.1 found, 204.0 required.

Intermediates B and C

Preparation of 2-Isopropoxynicotinic Acid (B) and 2-(2,2,2-Trifluoroethoxy)nicotinic Acid (C)

Intermediates B and C were made as described above, replacing 2,2-difluoroethanol with the appropriate alcohols.

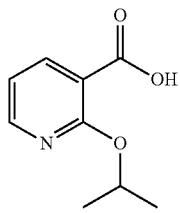

Intermediate B

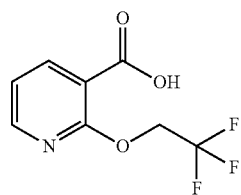

Intermediate C

Intermediate D

Preparation of 2-(2-Methoxyethyl)benzoic Acid

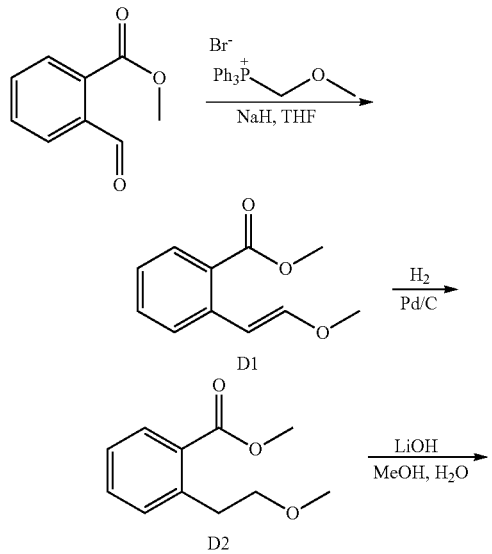

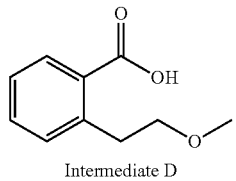

Intermediate D

Step 1: (E)-Methyl 2-(2-methoxyvinyl)benzoate (D1)

To a suspension of (methoxymethyl)triphenylphosphonium bromide (9.44 g, 27.4 mmol) in THF (50 mL) was added NaH (1.46 g, 36.6 mmol) at 0° C. portion wise. The mixture was stirred at 0° C. for 0.5 h and then a solution of methyl 2-formylbenzoate (3.0 g, 18.3 mmol) in THF (15 mL) added dropwise and the reaction mixture stirred at RT for 12 h. The mixture was diluted with water, extracted with EtOAc (30 mL×2) and the combined organic layers washed with brine, dried over MgSO$_4$, filtered, and concentrated in vacuo. The residue was purified by chromatography on silica (petroleum ether:EtOAc=10:1 to 3:1) to give the title compound as an oil.

Step 2: Methyl 2-(2-methoxyethyl)benzoate (D2)

To a solution of the product from step 1 (2.3 g, 11.9 mmol) in EtOAc (30 mL) was added Pd/C (200 mg) at RT and the mixture was stirred at RT overnight under a balloon of H$_2$. The mixture was filtered and the filtrate concentrated in vacuo to give the title compound, which was used directly in the next step.

Step 3: 2-(2-Methoxyethyl)benzoic acid (Intermediate D)

A mixture of the product from step 2 (2.2 g, 11.3 mmol) and LiOH (1.43 g, 33.9 mmol) in methanol (15 mL) and water (15 mL) was stirred at RT overnight. The mixture was adjusted to pH ~3 with 1N HCl and concentrated in vacuo. The residue was extracted with EtOAc (30 mL×3), and the combined organic layers were dried over Na$_2$SO$_4$, filtered and the filtrate was concentrated in vacuo to give the title compound as a solid, which was used without further purification.

Intermediate E

Preparation of 3-(1H-Pyrazol-1-yl)pyrazine-2-carboxylic Acid

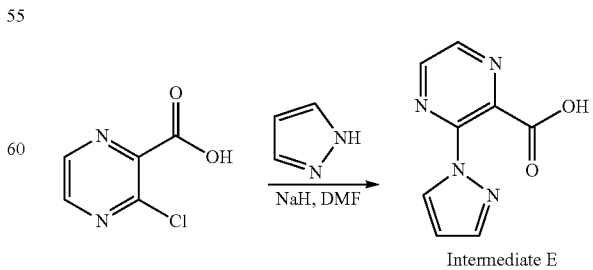

Intermediate E

To a suspension of sodium hydride (278 mg, 6.95 mmol, 60% in oil) in DMF (10 mL) was added 1H-pyrazole (279 mg, 4.11 mmol) at RT and the resulting mixture stirred at RT for 0.5 h. 3-Chloropyrazine-2-carboxylic acid (500 mg, 3.16 mmol) was added and the mixture heated to 60° C. for 2 h. After cooling to RT, water (20 mL) was added and the mixture extracted with 4.7% MeOH in DCM (20 mL×3). The combined organic layers were washed with brine, dried over $Na_2SO_4$, filtered and concentrated in vacuo to give the title compound as a solid. LRMS m/z (M+H) 191.0 found, 191.0 required.

Intermediate F

Preparation of 3-(Pyridin-2-yl)pyrazine-2-carboxylic Acid

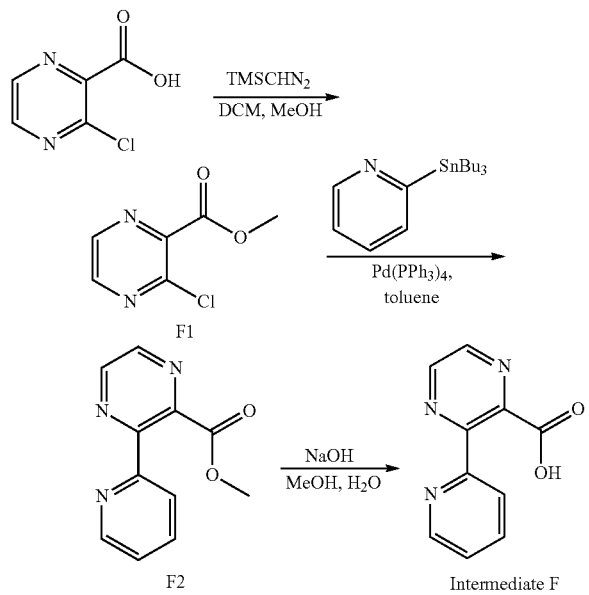

Step 1: Methyl 3-chloropyrazine-2-carboxylate (F1)

To a solution of 3-chloropyrazine-2-carboxylic acid (100 mg, 0.63 mmol) in DCM/MeOH (2 mL: 0.2 mL) was added $TMSCHN_2$ (0.47 mL, 0.95 mmol) at RT and the resulting mixture stirred at RT for 2 h. Acetic acid (0.2 mL) was added and the mixture diluted with water (2 mL) and extracted with DCM (4 mL×3). The combined organic layers were washed with brine, dried over $Na_2SO_4$, filtered and concentrated in vacuo to give the title compound as an oil. LRMS m/z (M+H) 173.0 found, 173.0 required.

Step 2: Methyl 3-(pyridin-2-yl)pyrazine-2-carboxylate (F2)

To a solution of the product from step 1 (100 mg, 0.58 mmol) in toluene (2 mL) was added $Pd(PPh_3)_4$ (134 mg, 0.12 mmol) and 2-(tributylstannyl)pyridine (213 mg, 0.58 mmol) at room temperature and the resulting mixture heated to 100° C. overnight. After cooling to RT, the mixture was filtered and 5 mL of aq. KF solution was added to the filtrate. The resulting mixture was stirred for 30 mins and extracted with EtOAc (5 mL×3). The combined organic layers were washed with brine, dried over $Na_2SO_4$, filtered and concentrated in vacuo. The residue was purified by chromatography (30% EtOAc in petroleum ether) to provide the title compound as an oil. LRMS m/z (M+H) 216.1 found, 216.1 required.

Step 3: 3-(Pyridin-2-yl)pyrazine-2-carboxylic acid (Intermediate F)

A solution of the product from step 2 (50 mg, 0.23 mmol) and NaOH (27.8 mg, 0.69 mmol) in 2 mL of methanol and 0.1 mL of water was stirred at RT overnight. After adjusting to pH=5 with 1N HCl, the mixture was concentrated in vacuo. The residue was dissolved in EtOAc (8 mL), stirred for 10 mins and filtered. The filtrate was concentrated in vacuum to give the title compound as a solid. LRMS m/z (M+H) 202.1 found, 202.1 required.

Intermediate G

Preparation of 4-Fluoro-2-(2H-1,2,3-triazol-2-yl)benzoic Acid

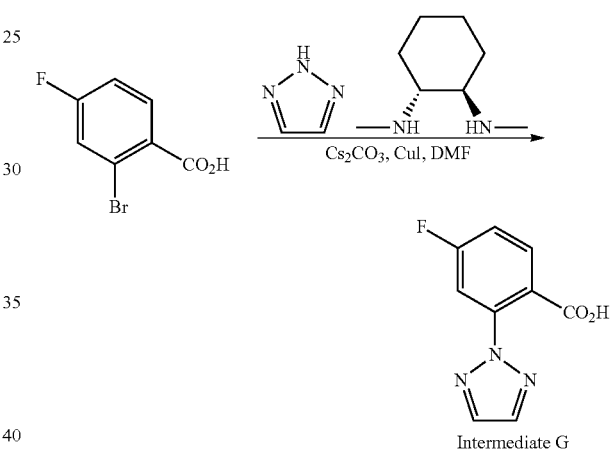

To a mixture of 2-bromo-4-fluorobenzoic acid (30 g, 137 mmol), cesium carbonate (89.26 g, 274 mmol) and CuI (5.27 g, 27.4 mmol) in DMF (200 mL) were added N,N'-dimethylcyclohexane-1,2-diamine (3.7 mL, 23.3 mmol) and 1H-1,2,3-triazole (18.92 g, 274 mmol). The resulting mixture was stirred at 110° C. overnight, cooled, concentrated in vacuo and diluted with water (150 mL). The aqueous layer was extracted with EtOAc (300 mL×3). The aqueous layer was acidified with 2N HCl and extracted with EtOAc (300 mL×4). The combined organic layers were washed with brine (150 mL×3), dried over $Na_2SO_4$, filtered and the filtrate concentrated in vacuo. The residue was purified by chromatography on silica gel (petroleum ether:EtOAc=100:1~5:1) to provide the title compound as a solid. LRMS m/z (M+H) 208.0 found, 208.0 required.

Intermediates H, I and J

Preparation of 3-Fluoro-2-(2H-1,2,3-triazol-2-yl) benzoic Acid (H), 5-Fluoro-2-(2H-1,2,3-triazol-2-yl)benzoic Acid (I) and 6-Fluoro-2-(2H-1,2,3-triazol-2-yl)benzoic acid (J)

Intermediates H, I, J were prepared in a similar manner to that described for Intermediate G, replacing 2-bromo-4- fluorobenzoic acid with the appropriate bromo or iodo substituted fluorobenzoic acids.

Intermediate H

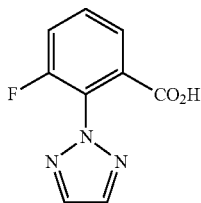

Intermediate I

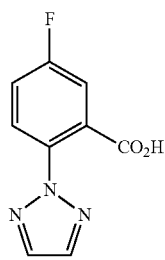

Intermediate J

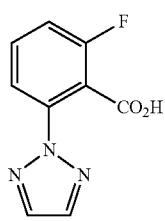

Intermediate K

Preparation of 2-(2H-Tetrazol-2-yl)benzoic Acid

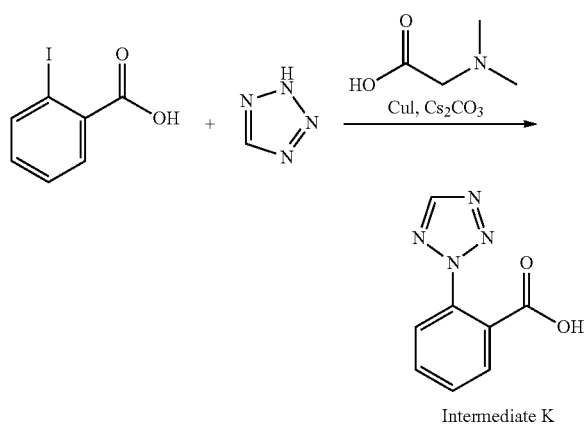

Intermediate K

To a 20 mL microwave tube was charged 2-iodobenzoic acid (1.85 g, 7.46 mmol), cesium carbonate (4.06 g, 12.5 mmol), copper(I) iodide (0.128 g, 0.671 mmol), and DMA (8.0 mL). N,N'-Dimethylglycine (0.131 g, 1.27 mmol) and tetrazole (1.29 g, 18.4 mmol) were added, and the solution was irradiated in a microwave reactor at 100° C. for 1 h. The reaction was diluted with water and 1 N aqueous sodium hydroxide and washed with EtOAc. The aqueous fraction was acidified with conc. HCl and extracted 2× with EtOAc. The combined organic fractions were washed with brine, dried over magnesium sulfate, filtered, and concentrated. The residue was purified by silica gel gradient chromatography [0-85% (1% acetic acid in EtOAc) in hexanes], providing the title compound. $^1$H NMR (400 MHz, CD$_3$OD): δ 7.72-7.84 (m, 3 H), 8.07 (dd, J=7.6, 1.6 Hz, 1 H), 8.90 (s, 1 H) ppm. LRMS m/z (M+H) 191.1 found, 191.2.

Intermediate L

Preparation of 2-(2H)-1,2,3-Triazol-2-yl)thiophene-3-carboxylic Acid

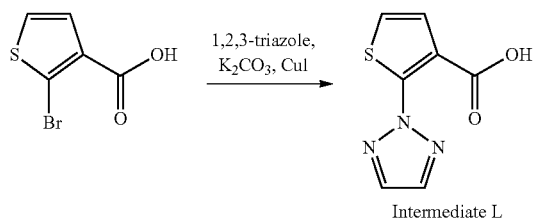 [SMILES: O=C(O)c1ccsc1Br ; O=C(O)c1ccsc1-n1nccn1]

Intermediate L

A solution of 2-bromo-3-thiophene carboxylic acid (1.50 g, 7.24 mmol), 1H-1,2,3-triazole (0.600 g, 8.69 mmol), potassium carbonate (2.00 g, 14.5 mmol), and copper iodide (0.138 g, 0.724 mmol) in DMF (36.2 mL) was purged subsurface with nitrogen and heated to 75° C. for 96 h. The reaction was diluted with water, washed with ether, and acidified with conc. HCl. The acidic aqueous solution was extracted 3× with EtOAc and the combined organic fractions were washed with brine, dried over magnesium sulfate, filtered, and concentrated. The crude material was purified by silica gel gradient chromatography [0-70% (1% acetic acid in EtOAc) in hexanes], providing the title compound as a solid. LRMS m/z (M+H) 196.2 found, 196.1 required.

Intermediate M

Preparation of Potassium 2-(pyrimidin-2-yl)thiophene-3-carboxylate

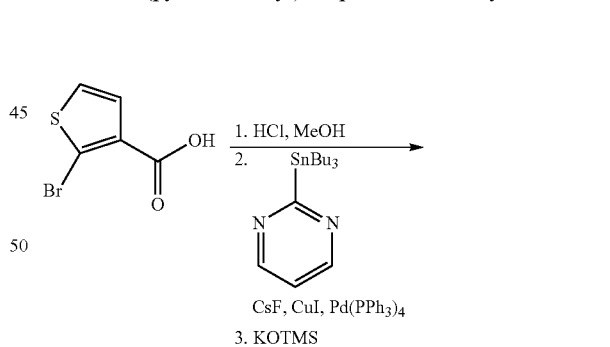

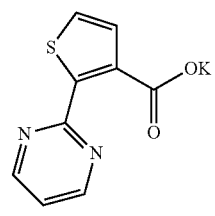

Intermediate M

A solution of 2-bromo-3-thiophene carboxylic acid (3.35 g, 16.2 mmol) in methanol (50 mL) was cooled to 0° C. and saturated with gaseous HCl. The solution was heated to 60°

C. overnight, then concentrated in vacuo. The residue was redissolved in EtOAc, washed with saturated aqueous sodium bicarbonate and brine, dried over sodium sulfate, filtered, and concentrated, providing methyl 2-bromothiophene-3-carboxylate as an oil. LRMS m/z (M+H) 221.1 found, 221.0 required.

A solution of methyl 2-bromothiophene-3-carboxylate (1.74 g, 7.87 mmol), 2-(tributylstannyl)pyrimidine (4.36 g, 11.81 mmol), cesium fluoride (4.78 g, 31.5 mmol), and copper(I) iodide (0.450 g, 2.36 mmol) in DMF (16 mL) in a pressure vessel was purged subsurface with nitrogen and treated with palladium tetrakis (0.455 g, 0.394 mmol). The mixture was sealed and heated at 120° C. overnight. The reaction was partitioned between EtOAc and water and filtered through celite. The organic layer was washed with saturated aqueous sodium bicarbonate and brine, dried over MgSO$_4$, filtered, and concentrated. The residue was purified by silica gel gradient chromatography (0-30% EtOAc in hexanes), providing methyl 2-(pyrimidin-2-yl)thiophene-3-carboxylate as a solid. LRMS m/z (M+H) 221.2 found, 221.1 required.

A solution of methyl 2-(pyrimidin-2-yl)thiophene-3-carboxylate (0.695 g, 3.16 mmol) and potassium trimethylsilanolate (0.506 g, 3.94 mmol) in THF (16 mL) was stirred at RT overnight, then diluted with ether and filtered through a glass frit. The solids were washed with ether, and the filtrate was concentrated, providing the title compound as a solid. LRMS m/z (M+H) 207.3 found, 207.1 required.

Intermediate N

Preparation of 4-[1,2,3]Triazol-2-yl-thiophene-3-carboxylic Acid

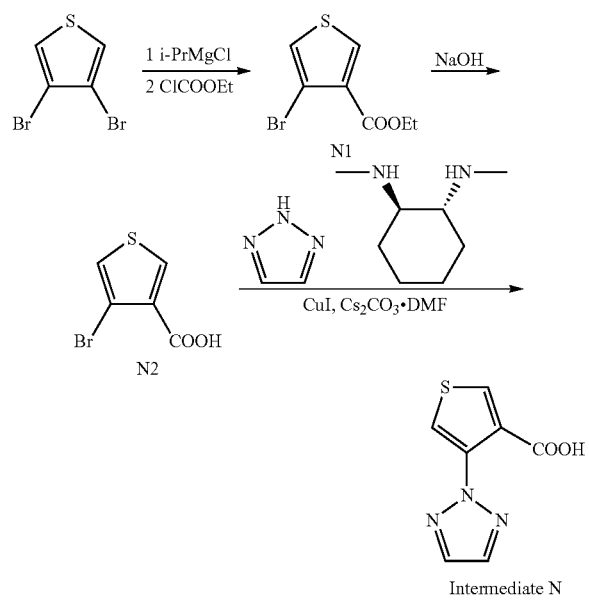

Step 1: 4-Bromo-thiophene-3-carboxylic acid ethyl ester (N1)

To a solution of 3,4-dibromothiophene (30 g, 0.12 mol) in THF (200 mL) at 0° C. was added i-PrMgCl (2.0 M solution in THF, 77 mL, 0.15 mol), keeping the temperature below 5° C. The resulting mixture was stirred at 0-5° C. for 5 h, ethyl chloroformate (14.4 mL, 0.15 mol) added dropwise with <10° C. and the resulting mixture warmed to RT, stirred overnight and quenched with saturated aqueous NH$_4$Cl. Most of the THF was then removed in vacuo, water added and the mixture extracted with EtOAc (80 mL×4). The combined organic layers were dried over Na$_2$SO$_4$, filtered, the filtrate concentrated in vacuo and the crude product purified by chromatography on silica (Petroleum ether: EtOAc=300:1) to provide the title compound as an oil.

Step 2: 4-Bromo-thiophene-3-carboxylic acid (N2)

To a solution of the product from step 1 (10 g, 43 mmol) in methanol (60 mL) was added sodium hydroxide (3.4 g, 86 mmol) and water (1 mL) and the mixture was stirred at RT overnight. The mixture was concentrated in vacuo, the residue diluted with water (30 mL) and extracted with EtOAc (25 mL×4). The pH of aqueous layer was adjusted to ~3 with 1M HCl and the aqueous phase extracted with EtOAc (25 mL×4). The combined extracts were dried over Na$_2$SO$_4$, filtered and the filtrate concentrated in vacuo to provide the title compound as a solid. LRMS m/z (M+H) 206.9, 208.9 found, 206.9, 208.9 required.

Step 3: 4-[1,2,3]Triazol-2-yl-thiophene-3-carboxylic acid (Intermediate N)

To a mixture of the product from step 2 (7.9 g, 38 mmol), Cs$_2$CO$_3$ (24.8 g, 76 mmol) and CuI (2.88 g, 7.6 mmol) in DMF (200 mL) were added 2H-[1,2,3]triazole (5.24 g, 76 mmol) and N,N'-dimethyl-cyclohexane-1,2-diamine (0.9 g, 6.5 mmol) and the mixture was stirred at 110° C. overnight. The cooled mixture was adjusted to pH ~12 with 1M sodium hydroxide and extracted with EtOAc (50 mL×3). The aqueous layer was adjusted to pH ~4 with 1M HCl and extracted with EtOAc (50 mL×4). The extracts were dried over Na$_2$SO$_4$, filtered, the filtrate concentrated in vacuo and the residue purified by chromatography on silica (Petroleum ether:EtOAc=10:1) to provide the title compound. LRMS m/z (M+H) 196.0 found, 196.0 required.

Intermediate P

Preparation of 2-(1-Cyanocyclopropyl)benzoic Acid

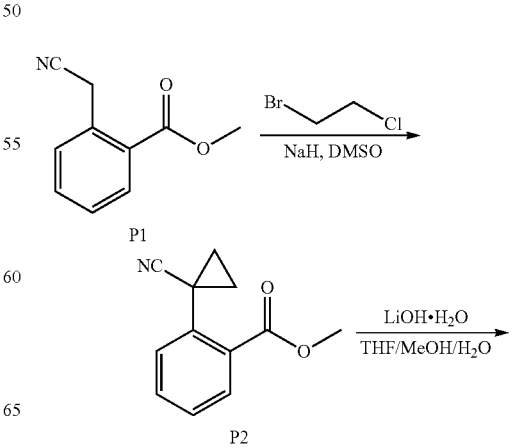

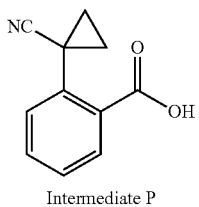

Intermediate P

Step 1: Methyl 2-(1-cyanocyclopropyl)benzoate (P2)

To a solution of NaH (1.1 g, 26.2 mmol) in DMSO (20 mL) was added compound P1 (2 g, 11.4 mmol); after stirring at RT under nitrogen for 1 h, 1-bromo-2-chloroethane (1.8 g, 12.6 mmol) was added and the mixture stirred at RT for 2 h. The mixture was quenched with ice water (10 mL) and extracted with EtOAc (10 mL×3). The organic layer was combined, dried and concentrated in vacuo to give the crude compound, purified by column chromatography on silica (Petroleum Ether/EtOAc 20:1) to give the title compound as a solid. MS (ESI) m/e (M+H+) was detected.

Step 2: 2-(1-Cyanocyclopropyl)benzoic acid (Intermediate P)

A solution of compound P2 in THF/MeOH/H$_2$O (3:1:1, 16 mL) was treated with lithium hydroxide in water (3 mL). The mixture was stirred overnight at RT. The THF and MeOH were removed in vacuo and the resulting solution acidified to pH ~1 with HCl (1 N) to give a white crystalline precipitate. The crystals were isolated by filtration, washed with water and dried in vacuo affording intermediate P as a solid. MS (ESI) m/e (M+H$^+$): 187.9.

Intermediate Q

Preparation of 2-(2,2-Difluoroethoxy)benzoic Acid

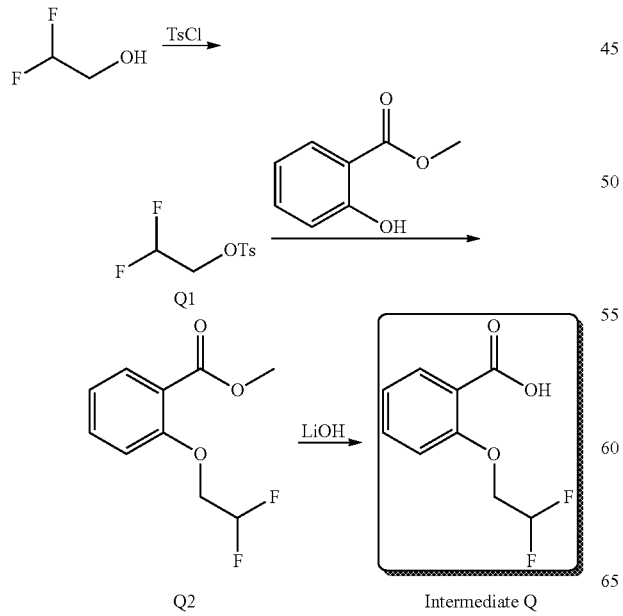

Step 1: 2,2-Difluoroethyl 4-methylbenzenesulfonate (Q1)

To a solution of 2,2-difluoroethanol (8.2 g, 100 mmol) in DCM (200 mL) at 0° C. was added Et$_3$N (15.1 g, 150 mmol) and TsCl (19.0 g, 100 mmol). The resulting mixture was stirred at 0° C. for 0.5 h, poured into water and extracted with DCM (200 mL×3). The combined organic layers were dried over MgSO$_4$, filtered and concentrated in vacuo to give the title compound as an oil, used without further purification.

$^1$HNMR (Methanol-d4, 400 MHz): δ 7.74 (d, J=8.2 Hz, 1H), 7.31 (d, J=8.2 Hz, 1H), 5.65-6.07 (m, 1H), 4.10 (td, J=12.6, 4.1 Hz, 2H), 2.40 (s, 3H).

Step 2: Methyl 2-(2,2-difluoroethoxy)benzoate (Q2)

To a suspension of the product from step 1 (7.6 g, 50.0 mmol) and K$_2$CO$_3$ (13.8 g, 100 mmol) in THF (300 mL) was added methyl 2-hydroxybenzoate (11.8 g, 50.0 mmol). The resulting mixture was stirred at 70° C. overnight, cooled to RT, poured into water and extracted with EtOAc (200 mL×3). The combined organic layers were dried over MgSO4, filtered and concentrated in vacuo. The residue was purified by chromatography on silica (3.2% EtOAc in petroleum ether) to give the title compound as a solid.

$^1$H NMR (CDCl$_3$, 400 MHz): δ 7.73-7.89 (m, 1H), 7.41-7.60 (m, 1H), 7.07 (t, J=7.4 Hz, 1H), 6.96 (d, J=8.2 Hz, 1H), 5.87-6.33 (m, 1H), 4.24 (td, J=12.9, 3.9 Hz, 2H), 3.88 (s, 3H)

Step 3: 2-(2,2-Difluoroethoxy)benzoic acid (Intermediate Q)

To a solution of the product from step 2 (4.5 g, 20.8 mmol) in methanol/water (100 mL/100 mL) was added LiOH.H2O (4.37 g, 104 mmol) and the resulting mixture stirred at RT overnight. The mixture was diluted with water (100 mL) and extracted with EtOAc (100 mL ×3). The aqueous layer was acidified with HCl (2M) to pH~2 and extracted with DCM (100 mL ×4). The combined organic layers were washed with brine, dried over Na$_2$SO$_4$, filtered and the filtrate concentrated in vacuo to give the title compound as a solid. LRMS m/z (M+H) 203.1 found, 203.1 required. $^1$HNMR (Methanol-d4, 400MHz): δ 7.80 (dd, J=7.5, 1.5 Hz, 1H), 7.44-7.62 (m, 1H), 7.03-7.28 (m, 2H), 5.97-6.45 (m, 1H), 4.31 (td, J=13.4, 4.0 Hz, 2H).

Intermediate R

Preparation of 2-(2,2-Difluorocyclopropyl)benzoic Acid

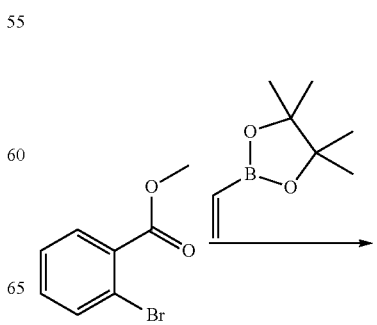

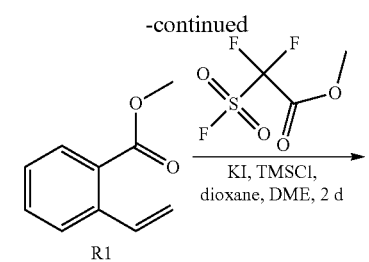
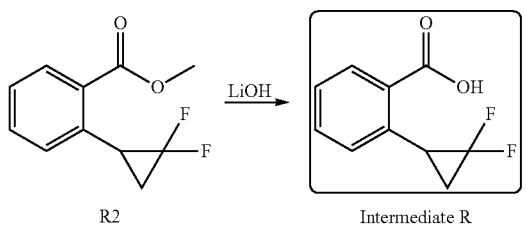

Step 1: Methyl 2-vinylbenzoate (R1)

To a solution of methyl 2-bromobenzoate (1.2 g, 5.5 mmol) in dioxane/water (15 mL/0.6 mL) were added 4,4,5,5-tetramethyl-2-vinyl-1,3,2-dioxa borolane (1.7 g, 11.1 mmol), K$_2$CO$_3$ (1.53 g, 11.1 mmol) and Pd(dppf)Cl$_2$ (0.4 g) and the resulting mixture stirred at 100° C. overnight. The cooled mixture was diluted with water (20 mL) and extracted with EtOAc (30 mL×3). The combined organic layers were washed with brine, dried over Na$_2$SO$_4$, filtered and the filtrate concentrated in vacuo. The residue was purified by preparative TLC (10% EtOAc in petroleum ether) to give the title compound as an oil. LRMS m/z (M+H) 163.1 found, 163.1 required. $^1$H NMR (Methanol-d4, 400MHz): δ 7.87 (d, J=7.6 Hz, 1H), 7.28-7.57 (m, 4H), 5.61 (d, J=17.6 Hz, 1H), 5.35 (d, J=11.2 Hz, 1H), 3.88 (s, 3H).

Step 2: Methyl 2-(2,2-difluorocyclopropyl)benzoate (R2)

A mixture of the product from step 1 (500 mg, 3.09 mmol) and KI (1.15 g, 6.94 mmol) in DME (27.8 mg, 0.31 mmol) and dioxane (461.7 mg, 5.25 mmol) was stirred at 120° C. for 5 minutes. TMSCl (667 mg, 6.17 mmol) and methyl 2,2-difluoro-2-(fluorosulfonyl)acetate (1.2 g, 6.17 mmol) were added and the resulting mixture stirred at 120° C. for 24 h. The cooled mixture was diluted with water and extracted with EtOAc (10 mL×3). The combined organic layers were dried over Na$_2$SO$_4$, filtered and concentrated in vacuo. The residue was purified by preparative HPLC to afford the desired product as a solid. LRMS m/z (M+H) 213.2 found, 213.2 required.

Step 3: 2-(2,2-Difluorocyclopropyl)benzoic acid (Intermediate R)

A solution of the product from step 2 (170 mg, 0.8 mmol) and LiOH (23 mg, 0.55 mmol) in mixed solvent THF:H$_2$O:MeOH (2:2:1) was stirred at 0° C. overnight. The reaction mixture was diluted with water (6 mL), adjusted pH to ~2 with 1 M HCl and extracted with EtOAc (8 mL×3). The combined organic layers were washed with brine (10 mL), dried over Na$_2$SO$_4$, filtered and concentrated in vacuo. The residue was purified by preparative HPLC to give the title compound as a solid. LRMS m/z (M+H) 199.1 found, 199.1 required. $^1$H (Methanol-d4, 400MHz): δ 7.95 (d, J=7.2 Hz, 1H), 7.34-7.53 (m, 3H), 3.31-3.36 (m, 1H), 1.81-1.84 (m, 1H), 1.62-1.66 (m, 1H).

EXAMPLE 1

(1 2-{3-[(3R,6R)-6-Methyl-1-{[2-(2H-1,2,3-triazol-2-yl)phenyl]carbonyl}piperidin-3-yl]isoxazol-5-yl}propan-2-ol)

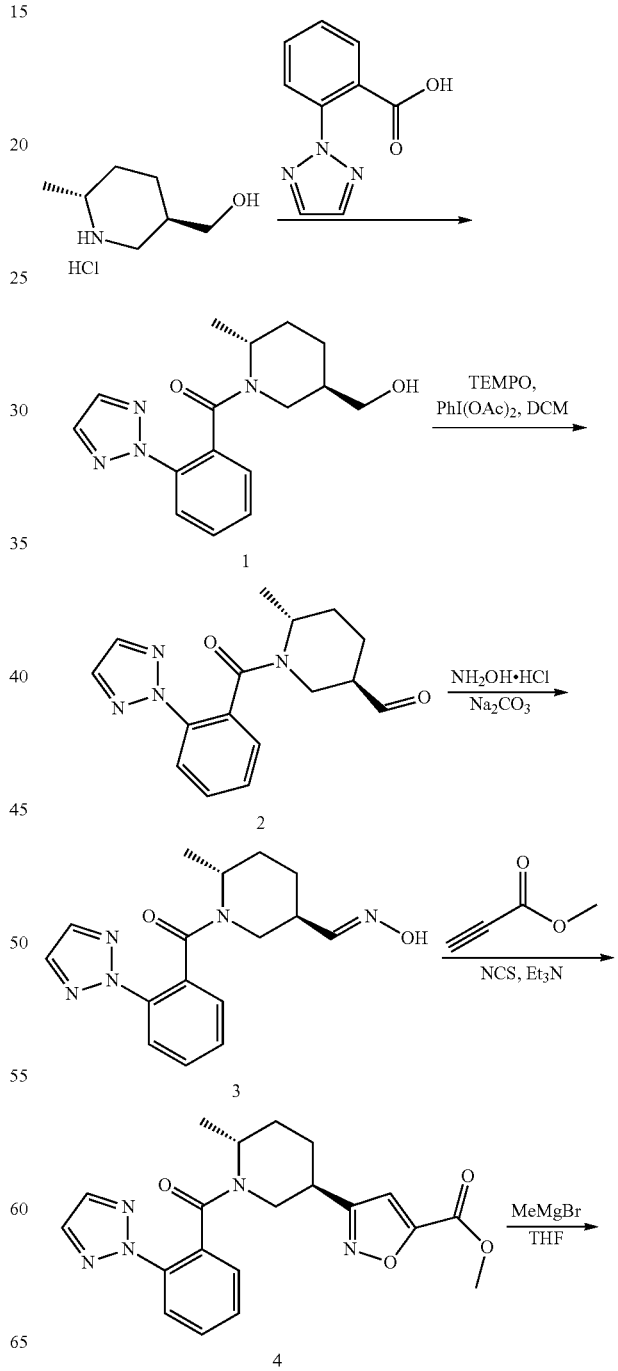

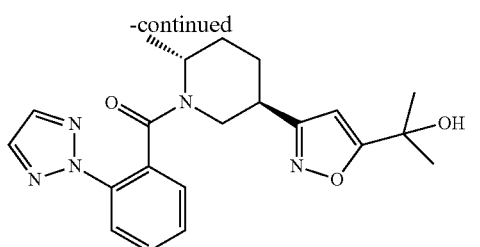

Example 1

Step 1: (2-(2H-1,2,3-Triazol-2-yl)phenyl)((2R,5R)-5-(hydroxymethyl)-2-methylpiperidin-1-yl)methanone (1)

A solution of 2-(2H-1,2,3-triazol-2-yl)benzoic acid (500 mg, 2.64 mmol) in SOCl₂ (5 mL) was heated to reflux for 1 h, cooled to RT and concentrated in vacuo. The residue was dissolved in toluene (5 mL) and added to a solution of ((3R,6R)-6-methylpiperidin-3-yl)methanol hydrochloride (437 mg, 2.65 mmol) in toluene (5 mL), followed by addition of aq. NaOH (5.3 mL, 1M, 5.3 mmol). The resulting mixture was stirred at 10° C. for 12 h, poured into water (5 mL) and extracted with EtOAc (5 mL×3). The combined organic layers were dried over Na₂SO₄, filtered and concentrated in vacuo. The residue was purified by chromatography on silica (20-50% EtOAc in petroleum ether) to afford the title compound as a solid. LRMS m/z (M+H) 301.1 found, 301.2 required.

Step 2: (3R,6R)-1-(2-(2H-1,2,3-Triazol-2-yl)benzoyl)-6-methylpiperidine-3-carbaldehyde (2)

To a solution of the product from step 1 (728 mg, 2.43 mmol) in DCM (10 mL) was added TEMPO (227 mg, 1.45 mmol) and iodobenzene diacetate (939 mg, 2.92 mmol). The mixture was stirred at 10° C. for 1 h, diluted with aq.Na₂S₂O₃ (10 mL) and extracted with DCM (10 mL×3). The combined organic layers were washed with brine (10 mL), dried over Na₂SO₄, filtered and concentrated in vacuo. The residue was purified by chromatography on silica (20-50% EtOAc in petroleum ether) to afford the title compound as an oil. LRMS m/z (M+H) 299.1 found, 299.2 required.

Step 3: (E)-1-(2-(2H-1,2,3-Triazol-2-yl)benzoyl)-6-methylpiperidine-3-carbaldehyde oxime (3)

To a solution of the product from step 2 (300 mg, 1 mmoL) in EtOH/water (5 mL, 10:1) was added NH₂OH·HCl (90 mg, 1.3 mmol) and Na₂CO₃ (138 mg, 1.3 mmol). The resulting mixture was stirred at RT for 2 h and extracted with EtOAc (10 mL×3). The combined organic layers were washed with water (10 mL) and brine (10 mL), dried over Na₂SO₄, filtered and concentrated in vacuo to afford the title compound as an oil. LRMS m/z (M+H) 314.2 found, 314.2 required.

Step 4: Methyl 3-((3R,6R)-1-(2-(2H-1,2,3-triazol-2-yl)benzoyl)-6-methylpiperidin-3-yl)isoxazole-5-carboxylate (4)

To a solution of the product from step 3 (80 mg, 0.255 mmol) in DMF (5 mL) was added NCS (37 mg, 0.275 mmol). The resulting mixture was stirred at 50° C. for 1.5 h, cooled to 0-5° C. and TEA (39 mg, 0.38 mmol) and methyl propiolate (32 mg, 0.38 mmol) added. The resulting mixture was stirred at RT overnight, filtered and the filtrate purified by preparative HPLC to give the title compound as an oil. LRMS m/z (M+H) 396.2 found, 396.2 required.

Step 5: 2-{3-[(3R,6R)-6-Methyl-1-{[2-(2H-1,2,3-triazol-2-yl)phenyl]carbonyl}piperidin-3-yl]isoxazol-5-yl}propan-2-ol (Example 1)

To a solution of the product from step 4 (150 mg, 0.379 mmol) in THF (5 mL) at 0° C. was added MeMgBr (0.38 mL, 3M, 1.14 mmoL). The resulting mixture was stirred at RT overnight, diluted with aqueous NH₄Cl (3 mL), and extracted with EtOAc (5 mL×3). The combined organic layers were washed with brine (5 mL), dried over Na₂SO₄ and concentrated in vacuo. The residue was purified by preparative HPLC to give the title compound as an oil. LRMS m/z (M+H) 396.2 found, 396.2 required.

EXAMPLE 2

(1-(2-((2R,5R)-5-(5-(2-Hydroxypropan-2-yl)isoxazol-3-yl)-2-methylpiperidine-1-carbonyl)phenyl)cyclopropanecarbonitrile)

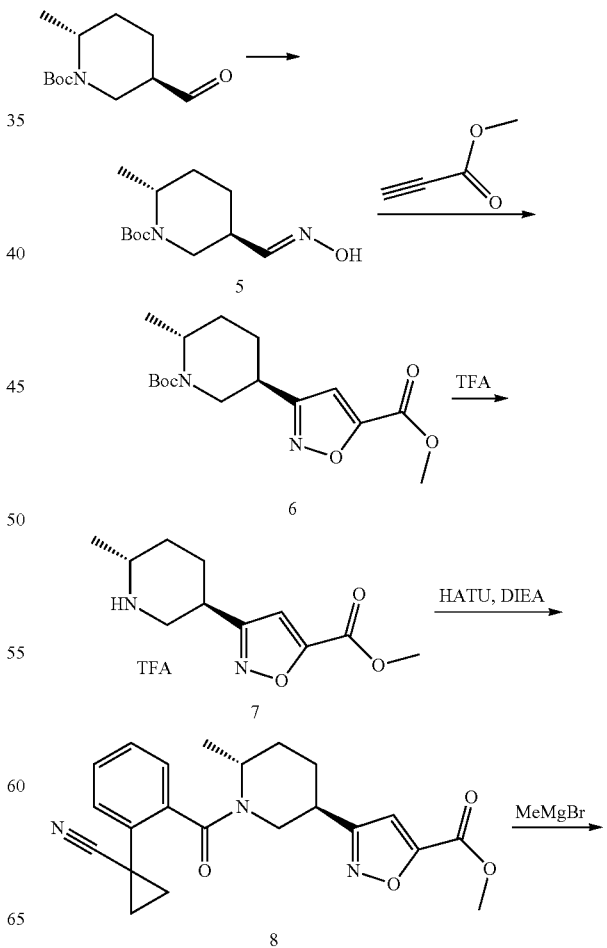

-continued

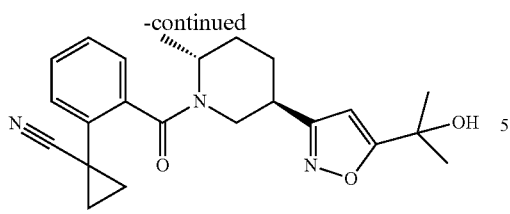

Example 2

Step 1: (2R,5R)-tert-Butyl 5-((E)-(hydroxyimino)methyl)-2-methylpiperidine-1-carboxylate (5)

A mixture of (2R,5R)-tert-butyl 5-formyl-2-methylpiperidine-1-carboxylate (1.3 g, 5.73 mmol), hydroxylamine hydrochloride (597 mg, 8.59 mmol) and $Na_2CO_3$ (911 mg, 8.59 mmol) in EtOH (20 mL) and water (2 mL) was heated to reflux overnight. The cooled mixture was concentrated in vacuo, diluted with water (10 mL) and EtOAc (50 mL) and extracted with EtOAc (20 mL×3). The combined organic layers were dried over $Na_2SO_4$, filtered and concentrated in vacuo to give the title compound as a solid, which was used directly in the next step. LRMS m/z (M+1) 243.1 found, 243.1 required.

Step 2: Methyl 3-((3R,6R)-1-(tert-butoxycarbonyl)-6-methylpiperidin-3-yl)isoxazole-5-carboxylate (6)

To a solution of the product from step 1 (200 mg, 0.82 mmol) in DMF (5 mL) was added NCS (131 mg, 0.98 mmol). The resulting mixture was stirred at 50° C. for 1.5 h, cooled to 0-5° C. and TEA (124 mg, 1.23 mmol) and methyl propiolate (103 mg, 1.23 mmol) added. The reaction mixture was stirred at RT overnight, filtered and the filtrate purified by preparative TLC (20% EtOAc in petroleum ether) to give the title compound as an oil. LRMS m/z (M+H) 325.1 found, 325.2 required.

Step 3: Methyl 3-((3R,6R)-6-methylpiperidin-3-yl)isoxazole-5-carboxylate 2,2,2-trifluoroacetate (7)

To a solution of the product from step 2 (200 mg, 0.61 mmol) in DCM (2 mL) was added TFA (2 mL) at RT and the mixture stirred at RT for 0.5 h and concentrated in vacuo to give the title compound, which was used directly in the next step. LRMS m/z (M+H) 225.1 found, 225.1 required.

Step 4: Methyl 3-((3R,6R)-1-(2-(1-cyanocyclopropyl)benzoyl)-6-methylpiperidin-3-yl)isoxazole-5-carboxylate (8)

To a solution of the product from step 3 (72 mg, 0.21 mmol) in DCM (2 mL) was added HATU (182 mg, 0.48 mmol), DIEA (83 mg, 0.64 mmol) and 2-(1-cyanocyclopropyl)benzoic acid (60 mg, 0.32 mmol). The resulting mixture was stirred at RT for 9 h, poured into water and extracted with EtOAc (50 mL×3). The combined organic layers were washed with brine, dried over $MgSO_4$, filtered and concentrated in vacuo. The residue was purified by preparative TLC (50% EtOAc in petroleum ether) to give the title compound as an oil. LRMS m/z (M+H) 394.2 found, 394.2 required.

Step 5: 1-(2-((2R,5R)-5-(5-(2-Hydroxypropan-2-yl)isoxazol-3-yl)-2-methylpiperidine-1-carbonyl)phenyl)cyclopropanecarbonitrile (Example 2)

To a solution of the product from step 4 (100 mg, 0.25 mmol) in THF (2 mL) at 0° C. was added MeMgBr (2 mL, 3M, 6.0 mmol) dropwise. The resulting mixture was stirred at 0° C. for 1 h, saturated aqueous $NH_4Cl$ added and the mixture extracted with EtOAc (200 mL×3). The combined organic layers were washed with brine, dried over $MgSO_4$, filtered, and concentrated in vacuo. The residue was purified by preparative HPLC to give the title compound as a solid. LRMS m/z (M+H) 394.2 found, 394.2 required.

EXAMPLES 3-4

Compounds in Examples 3-4 were prepared according to the methodology herein and the general procedure provided in Example 2. The starting materials are either commercially available or may be prepared as described in the intermediates preparation section, or may be prepared from commercially available reagents using conventional reactions well known in the art.

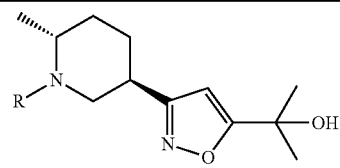

| Example | R | Name | LRMS or HRMS (M + H⁺) |
|---|---|---|---|
| 3 | ![Cl-phenyl-triazolyl] | (5-Chloro-2-(2H-1,2,3-triazol-2-yl)phenyl)((2R,5R)-5-(5-(2-hydroxypropan-2-yl)isoxazol-3-yl)-2-methylpiperidin-1-yl)methanone | Calc'd 430.2 found 430.1 |

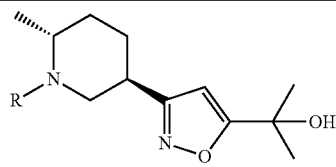

| Example | R | Name | LRMS or HRMS (M + H⁺) |
|---|---|---|---|
| 4 | 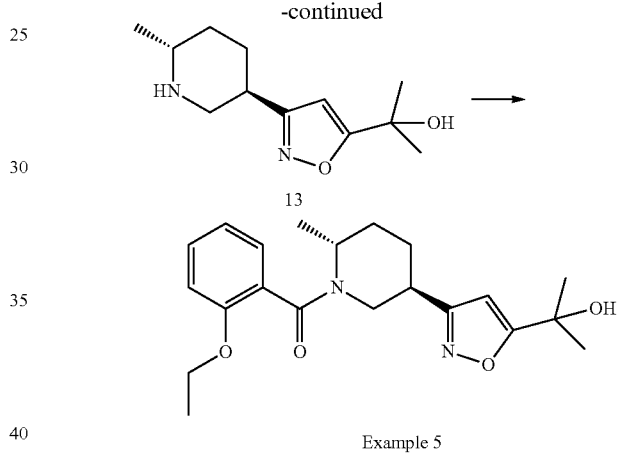 | (5-Fluoro-2-(2H-1,2,3-triazol-2-yl)phenyl)((2R,5R)-5-(5-(2-hydroxypropan-2-yl)isoxazol-3-yl)-2-methylpiperidin-1-yl)methanone | Calc'd 414.2 found 414.2 |

EXAMPLE 5

((2-Ethoxyphenyl)((2R,5R)-5-(5-(2-hydroxypropan-2-yl)isoxazol-3-yl)-2-methylpiperidin-1-yl)methanone

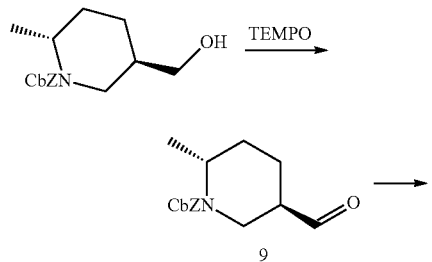

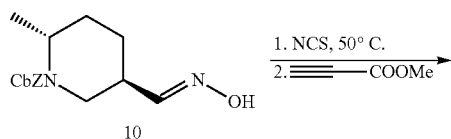

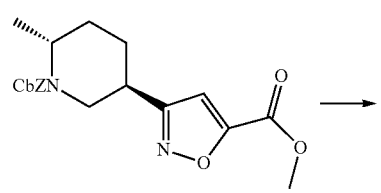

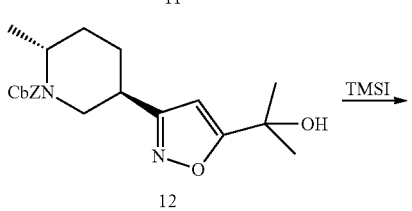

Step 1: (2R,5R)-Benzyl 5-formyl-2-methylpiperidine-1-carboxylate (9)

TEMPO (1.424 g, 9.11 mmol) was added to a stirred mixture of iodobenzene diacetate (5.87 g, 18.23 mmol) and (2R,5R)-benzyl 5-(hydroxymethyl)-2-methyl-piperidine-1-carboxylate (4 g, 15.19 mmol) in DCM (40 mL) at 0° C. The resulting mixture was stirred at RT for 4 h, diluted with DCM and washed with water, brine, dried over MgSO₄, filtered and concentrated in vacuo. The residue was purified by chromatography on silica (2-25% EtOAc in petroleum ether) to give the title compound as an oil. LRMS m/z (M+H) 262.2 found, 262.2 required.

Step 2: (2R,5R)-Benzyl 5-((E)-(hydroxyimino)methyl)-2-methylpiperidine-1-carboxylate (10)

To a solution of the product from step 1 (7.5 g, 28.7 mmol) in EtOH (70 mL) at 0° C. were added Na₂CO₃ (4.56 g, 43.1 mmol) and hydroxylamine hydrochloride (2.99 g, 43.1 mmol). The resulting mixture was stirred at 90° C. overnight, cooled to RT, filtered and concentrated in vacuo. The residue was purified by chromatography on silica (0-50% EtOAc in petroleum ether) to give the title compound as an oil. LRMS m/z (M+H) 277.1 found, 277.2 required.

Step 3: Ethyl 3-((3R,6R)-1-((benzyloxy)carbonyl)-6-methylpiperidin-3-yl)isoxazole-5-carboxylate (11)

To a solution of the product from step 2 (5.5 g, 19.90 mmol) in DMF (100 mL) at 0° C. was added NCS (3.19 g, 23.88 mmol). The resulting mixture was stirred at 50° C. for 90 min, cooled to 0° C. and TEA (4.16 ml, 29.9 mmol) added, followed by ethyl propiolate (2.93 g, 29.9 mmol). The mixture was stirred at 20° C. for 4 h, diluted with EtOAc (200 mL), washed with water and brine, dried over MgSO$_4$, filtered and concentrated in vacuo. The residue was purified by chromatography on silica (0-50% EtOAc in petroleum ether) to give the title compound as an oil. LRMS m/z (M+H) 373.2 found, 373.2 required.

Step 4: (2R,5R)-Benzyl 5-(5-(2-hydroxypropan-2-yl)isoxazol-3-yl)-2-methylpiperidine-1-carboxylate (12)

To a mixture of CeCl$_3$ (265 mg, 1.07 mmol) in THF (10 mL) was added CH$_3$MgBr (3.6 mL, 3M, 10.7 mmol, 3M in diethyl ether) and the mixture stirred at 70° C. for 1 h before cooling to −20° C. The product from step 3 (800 mg, 2.15 mmol) in THF (30 mL) was added and the resulting mixture stirred at −20° C. for 30 min and then at 0° C. for 2 h. Saturated aqueous NH$_4$Cl was added and the mixture extracted with EtOAc (60 mL×3). The combined organic layers were dried over MgSO$_4$, filtered and the filtrate concentrated in vacuo. The residue was purified by chromatography on silica (0-40% EtOAc in petroleum ether) to give the title compound as an oil. LRMS m/z (M+H) 359.2 found, 359.2 required.

Step 5: 2-(3-((3R,6R)-6-Methylpiperidin-3-yl)isoxazol-5-yl)propan-2-ol (13)

To a solution of the product from step 4 (40 mg, 0.112 mmol) in DCM (3 mL) at 0° C. was added TMSI (0.030 mL, 0.223 mmol) in DCM (1 mL). The resulting mixture was stirred at RT for 12 h, diluted with aq. NaHCO$_3$ and extracted with DCM. The combined organic layers were dried over MgSO$_4$, filtered and concentrated in vacuo to give the title compound as an oil. LRMS m/z (M+H) 225.1 found, 225.2 required.

Step 6: (2-Ethoxyphenyl)((2R,5R)-5-(5-(2-hydroxypropan-2-yl)isoxazol-3-yl)-2-methylpiperidin-1-yl)methanone (Example 5)

A solution of 2-ethoxybenzoic acid (17.94 mg, 0.108 mmol), HATU (41.0 mg, 0.108 mmol) and DIEA (0.047 mL, 0.270 mmol) in DMF (3 mL) was stirred at RT for 10 min, followed by addition of the product from step 5 (20 mg, 0.090 mmol). The resulting mixture was stirred at RT for 12 h and purified directly by preparative HPLC to give the title compound as a solid. LRMS m/z (M+H) 373.3 found, 373.2 required.

EXAMPLE 6

(((2R,5R)-5-(5-(2-Hydroxypropan-2-yl)isoxazol-3-yl)-2-methylpiperidin-1-yl)(2-isopropoxypyridin-3-yl)methanone)

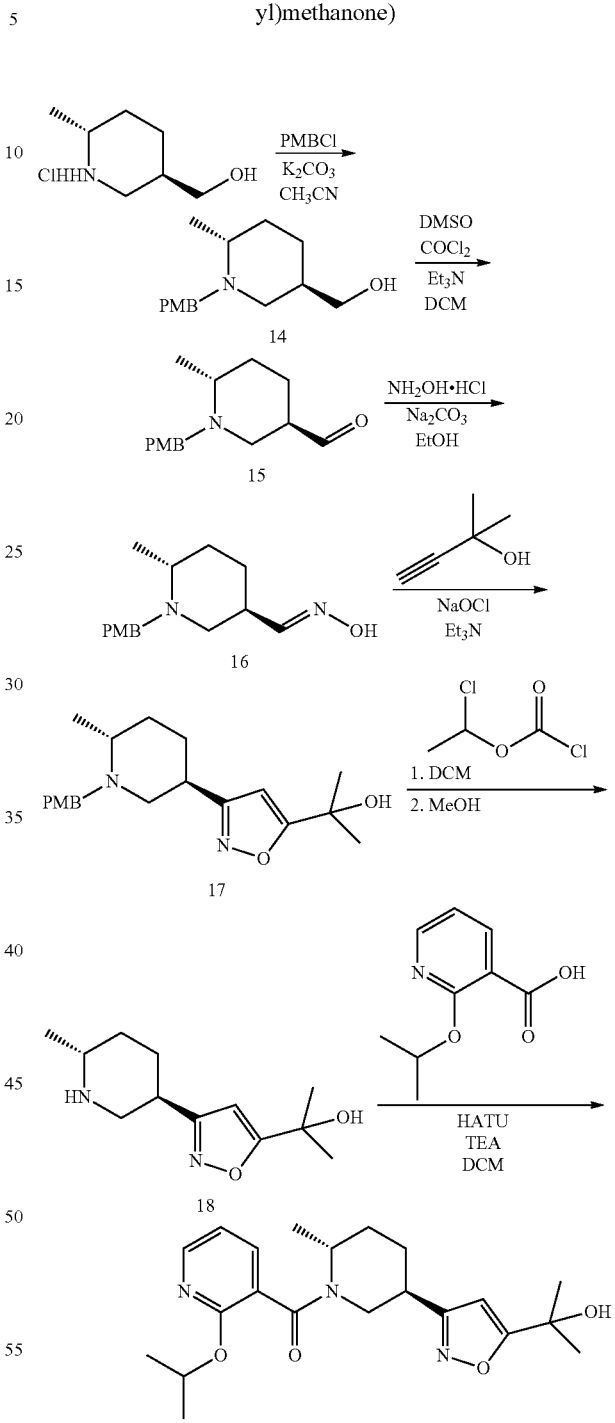

Example 6

Step 1: ((3R,6R)-1-(4-Methoxybenzyl)-6-methylpiperidin-3-yl)methanol (14)

A mixture of ((3R,6R)-6-methylpiperidin-3-yl)methanol hydrochloride (2.5 g, 15.09 mmol) and K$_2$CO$_3$ (5.21 g, 37.7 mmol) in MeCN (50 mL) was stirred at RT for 30 min and then 1-(chloromethyl)-4-methoxybenzene (2.363 g, 15.09 mmol) added. The resulting mixture was heated to 45° C. overnight, cooled to RT, filtered and the resulting cake washed with EtOAc (50 mL×3). The combined organics were dried over $Na_2SO_4$, filtered and concentrated in vacuo. The residue was purified by chromatography on silica (80% EtOAc in petroleum ether) to give the title compound as a solid. LRMS m/z (M+H) 250.1 found, 250.1 required.

Step 2: (3R,6R)-1-(4-Methoxybenzyl)-6-methylpiperidine-3-carbaldehyde (15)

A solution of DMSO (1.081 g, 13.84 mmol) in DCM (10 mL) at −70° C. was treated with oxalyl chloride (1.639 g, 12.91 mmol) and the mixture stirred at −70° C. for 30 min. The product from step 1 (2.3 g, 9.22 mmol) in DCM (20 mL) was added dropwise, the resulting mixture stirred for 1 h and TEA (4.67 g, 46.1 mmol) was added, maintaining the temperature below −50° C. The mixture was allowed to warm up to RT over 3 h, water (60 mL) added and the mixture extracted with DCM (80 mL×3). The combined organic layers were washed with water (70 mL) and brine (60 mL), dried over $Na_2SO_4$, filtered and concentrated in vacuo to give the title compound as an oil. LRMS m/z (M+H) 248.1 found, 248.1 required.

Step 3: (E)-1-(4-Methoxybenzyl)-6-methylpiperidine-3-carbaldehyde oxime (16)

A mixture of the product from step 2 (2.0 g, 8.09 mmol), hydroxylamine hydrochloride (0.674 g, 9.70 mmol) and $Na_2CO_3$ (2.143 g, 20.22 mmol) in EtOH (50 mL) was stirred at 30° C. overnight, concentrated in vacuo and the residue partitioned between EtOAc (100 mL) and water (50 mL). The mixture was separated and the organic layer dried over $Na_2SO_4$, filtered and concentrated in vacuo. The residue was purified by chromatography on silica (10% EtOAc in petroleum ether) to give the title compound as a solid. LRMS m/z (M+H) 263.1 found, 263.1 required.

Step 4: 2-(3-((3R,6R)-1-(4-Methoxybenzyl)-6-methylpiperidin-3-yl)isoxazol-5-yl)propan-2-ol (17)

To a solution of the product from step 3 (200 mg, 0.762 mmol), 2-methylbut-3-yn-2-ol (77 mg, 0.915 mmol) and TEA (10.63 μL, 0.076 mmol) in $CHCl_3$ (5 mL) at 0° C. was added aq. NaClO solution (1.9 mL, 0.762 mmol). The resulting mixture was stirred at 25° C. overnight, then water (10 mL) and $CHCl_3$ (20 mL) were added. The mixture was separated and the organic layer was concentrated in vacuo. The residue was purified by preparative HPLC to give the title compound as an oil. LRMS m/z (M+H) 345.1 found, 345.1 required.

Step 5: 2-(3-((3R,6R)-6-Methylpiperidin-3-yl)isoxazol-5-yl)propan-2-ol (18)

A mixture of the product from step 4 (105 mg, 0.305 mmol) and 1-chloroethyl chloroformate (87 mg, 0.610 mmol) in DCE (4 mL) was heated to reflux. The cooled mixture was concentrated in vacuo, dissolved in MeOH (2 mL) and heated to reflux for 1 h. The mixture was cooled to RT and concentrated in vacuo to give the title compound as an oil, which was used in the next step directly. LRMS m/z (M+H) 225.1 found, 225.1 required.

Step 6: ((2R,5R)-5-(5-(2-Hydroxypropan-2-yl)isoxazol-3-yl)-2-methylpiperidin-1-yl)(2-isopropoxypyridin-3-yl)methanone (Example 6)

A mixture of the product from step 5 (40 mg, 0.178 mmol), 2-isopropoxynicotinic acid (35.5 mg, 0.196 mmol), HATU (81 mg, 0.214 mmol) and TEA (0.075 mL, 0.535 mmol) in DCM (5 mL) was stirred at RT overnight. The mixture was concentrated in vacuo and the residue purified by preparative HPLC to give the title compound as a solid. LRMS m/z (M+H) 388.1 found, 388.2 required.

EXAMPLE 7

The compound in Example 7 was prepared according to the methodology herein and the general procedure provided in Example 6. The starting materials are either commercially available or may be prepared as described in the intermediates preparation section, or may be prepared from commercially available reagents using conventional reactions well known in the art.

| Example | R | Name | LRMS or HRMS (M + H+) |
|---|---|---|---|
| 7 | 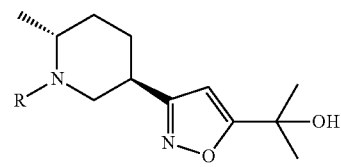 | ((2R,5R)-5-(5-(2-Hydroxypropan-2-yl)isoxazol-3-yl)-2-methylpiperidin-1-yl)(2-(2,2,2-trifluoroethoxy)pyridin-3-yl)methanone | Calc'd 428.2, found 428.1 |

EXAMPLE 8

(2-(2H-1,2,3-Triazol-2-yl)phenyl)((2R,5R)-5-(5-(3-hydroxypentan-3-yl)isoxazol-3-yl)-2-methylpiperidin-1-yl)methanone)

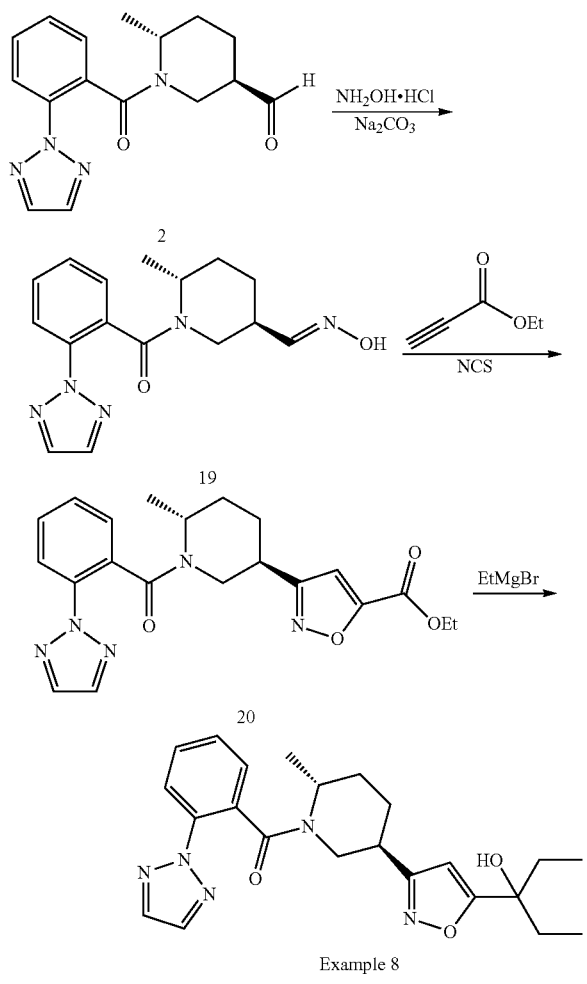

Example 8

Step 1: (E)-1-(2-(2H-1,2,3-triazol-2-yl)benzoyl)-6-methylpiperidine-3-carbaldehyde oxime (19)

To a solution of compound 2 (Example 1, Step 2) (500 mg, 1.68 mmol) in EtOH/water (5 mL/0.5 mL) was added hydroxylamine hydrochloride (174 mg, 2.52 mmol) and Na₂CO₃ (279 mg, 3.36 mmol). The resulting mixture was stirred at RT for 2 h diluted with water (50 mL) and extracted with EtOAc (100 mL×3). The combined organic layers were washed with brine (20 mL×3), dried over Na₂SO₄, filtered and concentrated in vacuo. The residue was purified by chromatography on silica (50% EtOAc in petroleum ether) to give the title compound as a solid. LRMS m/z (M+H) 314.1 found, 314.1 required.

Step 2: Ethyl 3-((3R,6R)-1-(2-(2H-1,2,3-triazol-2-yl)benzoyl)-6-methylpiperidin-3-yl)isoxazole-5-carboxylate (20)

To a solution of the product from step 1 (150 mg, 0.48 mmol) in DMF (2 mL) was added NCS (77 mg, 0.58 mmol).

The resulting mixture was stirred at 50° C. for 1.5 h, cooled to 0-5° C. with ice-bath and TEA (73 mg, 0.72 mmol) and methyl propiolate (60 mg, 0.72 mmol) added. The resulting mixture was stirred at RT overnight, diluted with water (10 mL) and extracted with EtOAc (50 mL×3). The combined organic layers were washed with brine (20 mL×3), dried over Na₂SO₄, filtered and concentrated in vacuo. The residue was purified by chromatography on silica (50% EtOAc in petroleum ether) to give the title compound as an oil. LRMS m/z (M+H) 410.2 found, 410.2 required.

Step 3: (2-(2H-1,2,3-triazol-2-yl)phenyl)((2R,5R)-5-(5-(3-hydroxypentan-3-yl)isoxazol-3-yl)-2-methylpiperidin-1-yl)methanone (Example 8)

To a solution of the product from step 2 (200 mg, 0.49 mmol) in THF (3 mL) at 0° C. under nitrogen was added ethyl magnesium bromide (0.5 mL, 3M, 1.5 mmol). The resulting mixture was stirred at 0° C. for 1 h, aqueous with ammonium chloride solution (3 mL) added, and the mixture extracted with EtOAc (200 mL×3). The combined organic layers were washed with brine (10 mL), dried over Na₂SO₄, filtered and concentrated in vacuo. The residue was purified by preparative HPLC to give the title compound as a solid. LRMS m/z (M+H) 424.2 found, 424.2 required.

EXAMPLES 9-10

(1-Cyclopropyl-1-{3-[(3R,6R)-6-methyl-1-{[2-(2H-1,2,3-triazol-2-yl)phenyl]carbonyl}piperidin-3-yl]isoxazol-5-yl}ethanol) (Ex. 9) and (1-Cyclopropyl-1-{3-[(3R,6R)-6-methyl-1-{[2-(2H-1,2,3-triazol-2-yl)phenyl]carbonyl}piperidin-3-yl]isoxazol-5-yl}ethanol) (Ex. 10)

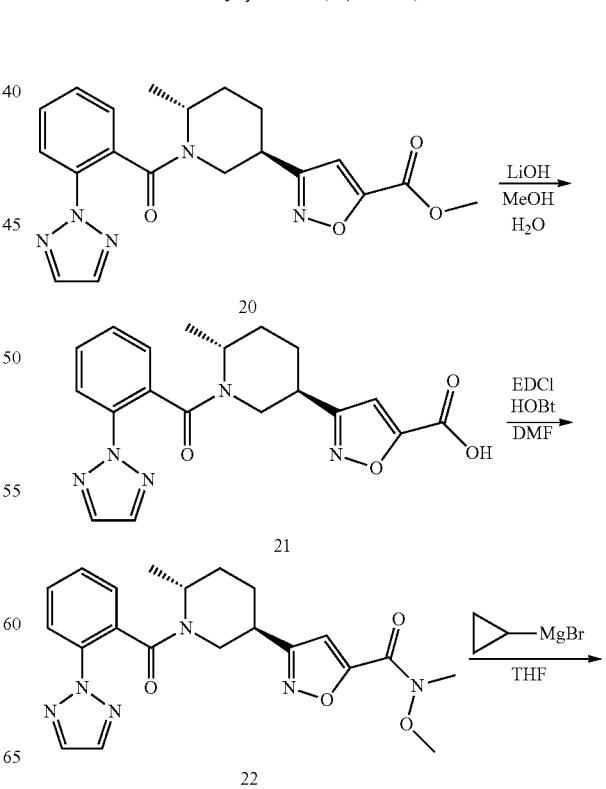

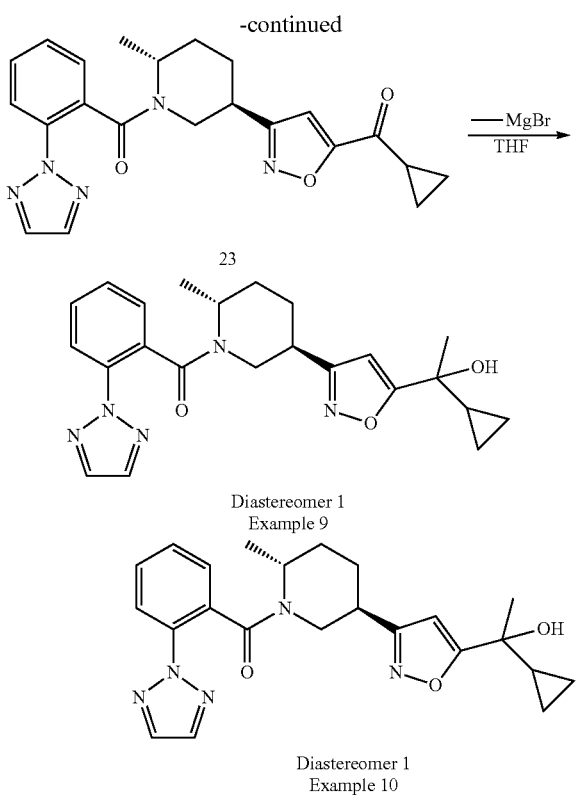

Step 1: 3-((3R,6R)-1-(2-(2H-1,2,3-Triazol-2-yl)benzoyl)-6-methylpiperidin-3-yl)isoxazole-5-carboxylic acid (21)

A solution of compound 4 (Example 1, Step 4) (400 mg, 1.01 mmol) and LiOH (42.5 mg, 1.01 mmol) in 5 mL of MeOH and 0.5 mL of $H_2O$ was stirred at RT overnight, the pH adjusted to ~6 with 1N HCl and the MeOH was removed in vacuo. The residue was diluted with water (20 mL) and extracted with EtOAc (30 mL×3). The combined organic layers were dried over $Na_2SO_4$, filtered and the filtrate was concentrated in vacuo to give the title compound as a solid, used directly in the next step without further purification. LRMS m/z (M+H) 382.2 found, 382.2 required.

Step 2: 3-((3R,6R)-1-(2-(2H-1,2,3-Triazol-2-yl)benzoyl)-6-methylpiperidin-3-yl)-N-methoxy-N-methylisoxazole-5-carboxamide (22)

To a solution of the product from step 1 (300 mg, 0.787 mmol) in DMF (10 mL) at RT were added MeONHMe.HCl (381 mg, 3.93 mmol), HOBt (127 g, 0.944 mmol), EDCI (300 mg, 1.57 mol) and $Et_3N$ (158 mg, 1.57 mmol). The resulting mixture was stirred at RT overnight, diluted with water and extracted with DCM (50 mL×3). The combined organic layers were washed with brine (20 mL), dried over $Na_2SO_4$, filtered and the filtrate concentrated in vacuo. The residue was purified by chromatography on silica (20% EtOAc in petroleum ether) to give the title compound as an oil. LRMS m/z (M+H) 425.2 found, 425.2 required.

Step 3: (3-((3R,6R)-1-(2-(2H-1,2,3-Triazol-2-yl)benzoyl)-6-methylpiperidin-3-yl)isoxazol-5-yl)(cyclopropyl)methanone (23)

To a solution of the product from step 2 (500 mg, 1.18 mmol) in THF (7 mL) at 0° C. was added cyclopropyl magnesium bromide (9.45 mL, 0.5M, 4.72 mmol). The mixture was stirred at RT for 1 h, diluted with aq. $NH_4Cl$ (10 mL) and extracted with EtOAc (10 mL×3). The combined organic layers were washed with preparative TLC (50% EtOAc in petroleum ether) to give the title compound as an oil. LRMS m/z (M+H) 406.2 found, 406.2 required.

Step 4: 1-Cyclopropyl-1-{3-[(3R,6R)-6-methyl-1-{[2-(2H-1,2,3-triazol-2-yl)phenyl]carbonyl}piperidin-3-yl]isoxazol-5-yl}ethanol (Example 9) and 1-cyclopropyl-1-{3-[(3R,6R)-6-methyl-1-{[2-(2H-1,2,3-triazol-2-yl)phenyl]carbonyl}piperidin-3-yl]isoxazol-5-yl}ethanol (Example 10)

To a solution of the product from step 3 (100 mg, 0.25 mmol) in THF (3 mL) at 0° C. was added methyl magnesium bromide (0.25 mL, 0.75 mmol). The resulting mixture was stirred at 0° C. for 1 h, aq. $NH_4Cl$ (5 mL) added and the mixture extracted with EtOAc (10 mL×3). The combined organic layers were washed with brine (10 mL), dried over $Na_2SO_4$, filtered and the filtrate was concentrated in vacuo. The residue was purified by preparative HPLC to give the title compound Example 9 (21 mg, faster eluting isomer in HPLC) as an oil and Example 10 (slower eluting isomer in HPLC) as an oil. Example 9: LRMS m/z (M+H) 422.2 found, 422.2 required. Example 10: LRMS m/z (M+H) 422.2 found, 422.2 required.

EXAMPLES 11-12

((2R)-2-{3-[(3R,6R)-6-Methyl-1-{[2-(2H-1,2,3-triazol-2-yl)phenyl]carbonyl}piperidin-3-yl]isoxazol-5-yl}butan-2-ol) (Ex. 11) and ((2S)-2-{3-[(3R,6R)-6-Methyl-1-{[2-(2H-1,2,3-triazol-2-yl)phenyl]carbonyl}piperidin-3-yl]isoxazol-5-yl}butan-2-ol) (Ex. 12)

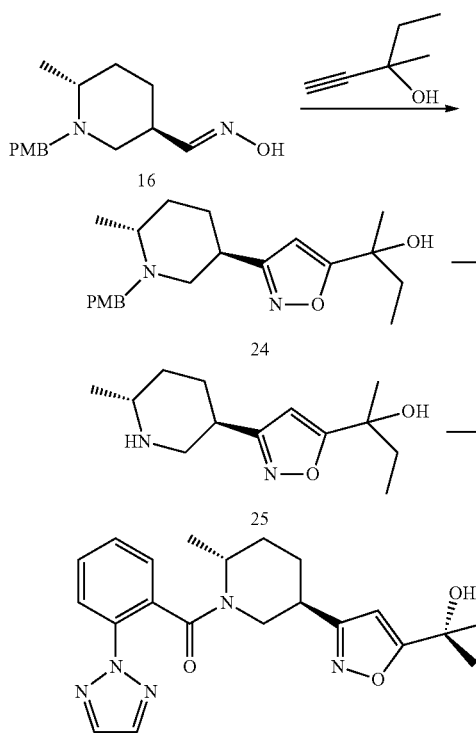

example 11

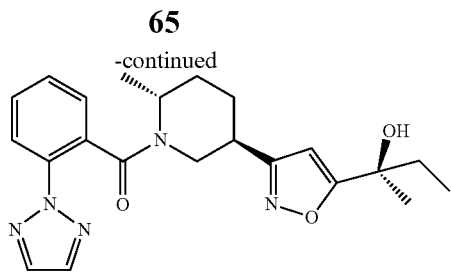

example 12

Step 1: 2-(3-((3R,6R)-1-(4-Methoxybenzyl)-6-methylpiperidin-3-yl)isoxazol-5-yl)butan-2-ol (24)

To a solution of compound 16 (Example 6, Step 3) (850 mg, 3.24 mmol), 3-methylpent-1-yn-3-ol (382 mg, 3.89 mmol) and TEA (0.045 mL, 0.324 mmol) in CHCl₃ (15 mL) at 0° C. was added aq. NaClO solution (3.44 mL, 3.24 mmol). The resulting mixture was stirred at 25° C. overnight, water (10 mL) added and the mixture extracted with CHCl₃ (20 mL). The organic layer was dried over Na₂SO₄, filtered and concentrated in vacuo. The residue was purified by preparative HPLC to give the title compound as an oil. LRMS m/z (M+H) 359.2 found, 359.2 required.

Step 2: 2-(3-((3R,6R)-6-Methylpiperidin-3-yl)isoxazol-5-yl)butan-2-ol (25)

A mixture of the product from step 1 (500 mg, 1.395 mmol), 1-chloroethyl chloroformate (399 mg, 2.79 mmol) and TEA (0.389 mL, 2.79 mmol) in DCE (20 mL) was heated to reflux overnight, the mixture cooled to RT and concentrated in vacuo. The residue was dissolved in MeOH (10 mL) and heated to reflux for 1 h, cooled to RT and concentrated in vacuo. The residue was purified by chromatography on silica (50% EtOAc in petroleum ether, then 10% MeOH in DCM) to give the title compound as an oil. LRMS m/z (M+H) 239.1 found, 239.1 required.

Step 3: (2-(2H-1,2,3-Triazol-2-yl)phenyl)((2R,5R)-5-(5-((R)-2-hydroxybutan-2-yl)isoxazol-3-yl)-2-methylpiperidin-1-yl)methanone (Example 11) and (2-(2H-1,2,3-triazol-2-yl)phenyl)((2R,5R)-5-(5-((S)-2-hydroxybutan-2-yl)isoxazol-3-yl)-2-methylpiperidin-1-yl)methanone (Example 12)

A mixture of the product from step 2 (350 mg, 1.469 mmol), 2-(2H-1,2,3-triazol-2-yl)benzoic acid (333 mg, 1.762 mmol), HATU (670 mg, 1.762 mmol) and DIEA (0.513 mL, 2.94 mmol) in DMF (10 mL) was stirred at RT overnight. The mixture was concentrated in vacuo and the residue purified by chromatography on silica (70% EtOAc in petroleum ether) to give a mixture of compounds (450 mg) as yellow oil, which were separated by SFC HPLC (Column: Chiralcel OD-3 150×4.6 mm I.D., 3 um Mobile phase: isopropanol (0.05% DEA) in CO₂ from 5% to 40% Flow rate: 2.5 mL/min Wavelength: 220 nm) to give Example 11 (faster eluting isomer) and Example 12 (slower eluting isomer) as solids. LRMS m/z (M+H) 410.0 found, 410.2 required.

EXAMPLE 13

(1-{3-[(3R,6R)-6-Methyl-1-{[2-(2H-1,2,3-triazol-2-yl)phenyl]carbonyl}piperidin-3-yl]isoxazol-5-yl}cyclobutanol)

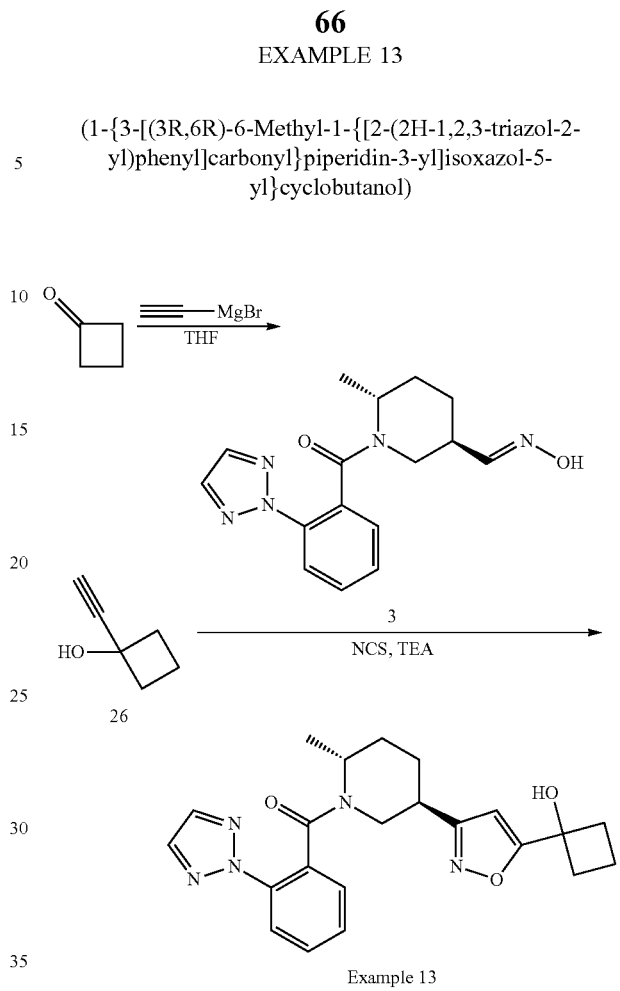

Example 13

Step 1: 1-Ethynylcyclobutanol (26)

To a solution of ethynylmagnesium bromide (28.5 mL, 14.2 mmoL) was added a solution of cyclobutanone (500 mg, 7.14 mmol) in THF (50 mL) at −78° C. The resulting mixture was stirred at −78° C. for 2 h, then aq. NH₄Cl (30 mL) added and the mixture extracted with EtOAc (30 mL×3). The combined organic layers were washed with brine (10 mL), dried over Na₂SO₄, filtered and the filtrate concentrated in vacuo to give the title compound as an oil.

Step 2: 1-{3-[(3R,6R)-6-Methyl-1-{[2-(2H-1,2,3-triazol-2-yl)phenyl]carbonyl}piperidin-3-yl]isoxazol-5-yl}cyclobutanol (Example 13)

To a solution of compound 3 (Example 1, Step 3) (978 mg, 3.12 mmol) in DMF (6 mL) was added NCS (623 mg, 4.68 mmol). The resulting mixture was stirred at 50° C. for 1.5 h, cooled to 0-5° C., TEA (473 mg, 4.68 mmol) and the product from step 1 (300 mg, 3.12 mmol) were added respectively. The resulting mixture was stirred at RT overnight, filtered, the filtrate concentrated in vacuo and the residue purified by preparative HPLC to give the title compound as a solid. LRMS m/z (M+H) 408.2 found, 408.2 required.

EXAMPLES 14-15

(1,1,1-Trifluoro-2-{3-[(3R,6R)-6-methyl-1-{[2-(2H-1,2,3-triazol-2-yl)phenyl]carbonyl}piperidin-3-yl]isoxazol-5-yl}propan-2-ol) (Ex. 14) and (1,1,1-Trifluoro-2-{3-[(3R,6R)-6-methyl-1-{[2-(2H-1,2,3-triazol-2-yl)phenyl]carbonyl}piperidin-3-yl]isoxazol-5-yl}propan-2-ol) (Ex. 15)

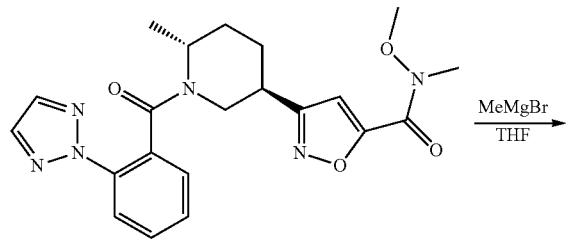

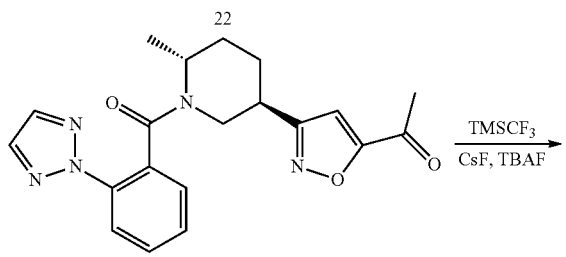

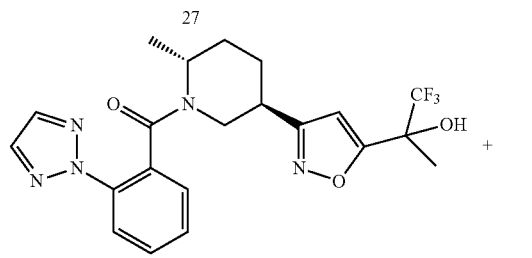

Step 1: 1-(3-((3R,6R)-1-(2-(2H-1,2,3-triazol-2-yl)benzoyl)-6-methylpiperidin-3-yl)isoxazol-5-yl)ethanone (27)

To a solution of compound 22 (Examples 9&10, Step 2) (200 mg, 0.47 mmol) in THF (5 mL) at 0° C. was added MeMgBr (0.31 mL, 3M, 0.94 mmol). The mixture was stirred at RT for 1 h, aq. NH₄Cl (5 mL) added and the mixture extracted with EtOAc (10 mL×3). The combined organic layers were washed with brine (10 mL), dried over Na₂SO₄, filtered and the filtrate concentrated in vacuo to give the title compound as an oil. LRMS m/z (M+H) 380.1 found, 380.2 required.

Step 2: 1,1,1-Trifluoro-2-{3-[(3R,6R)-6-methyl-1-{[2-(2H-1,2,3-triazol-2-yl)phenyl]carbonyl}piperidin-3-yl]isoxazol-5-yl}propan-2-ol (Example 14) and 1,1,1-trifluoro-2-{3-[(3R,6R)-6-methyl-1-{[2-(2H-1,2,3-triazol-2-yl)phenyl]carbonyl}piperidin-3-yl]isoxazol-5-yl}propan-2-ol (Example 15)

To a solution of the product from step 1 (300 mg, 0.79 mmol) in dry THF (5 mL) at 0° C. was added CsF (144 mg, 0.95 mmol) and TMSCF₃ (134 mg, 0.95 mmol). The resulting mixture was stirred at 0° C. for 1 h, TBAF (248 mg) added, the mixture stirred at RT for another 1 h and concentrated in vacuo. The residue was purified by preparative HPLC to give Example 14 (faster eluting isomer in HPLC) as an oil and Example 15 (slower eluting isomer in HPLC) as an oil. Example 14: LRMS m/z (M+H) 450.1 found, 450.2 required. Example 15: LRMS m/z (M+H) 450.1 found, 450.2 required.

EXAMPLES 16-17

(3-Methyl-2-{3-[(3R,6R)-6-methyl-1-{[2-(2H-1,2,3-triazol-2-yl)phenyl]carbonyl}piperidin-3-yl]isoxazol-5-yl}butan-2-ol) (Ex. 16) and (3-Methyl-2-{3-[(3R,6R)-6-methyl-1-{[2-(2H-1,2,3-triazol-2-yl)phenyl]carbonyl}piperidin-3-yl]isoxazol-5-yl}butan-2-ol) (Ex. 17)

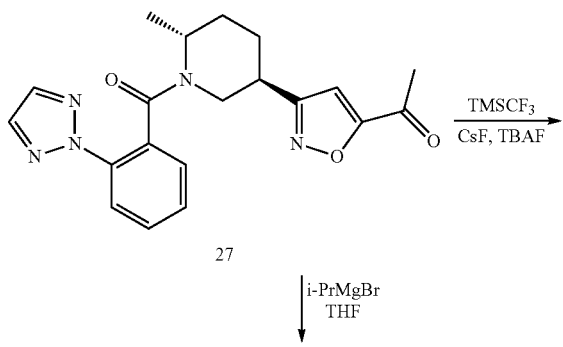

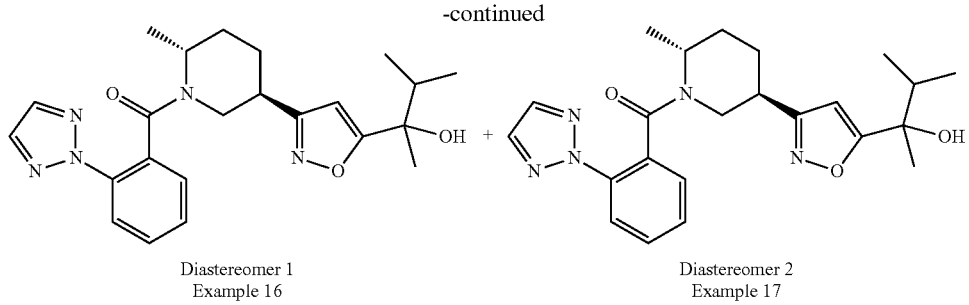

Diastereomer 1
Example 16

Diastereomer 2
Example 17

3-Methyl-2-{3-[(3R,6R)-6-methyl-1-{[2-(2H-1,2,3-triazol-2-yl)phenyl]carbonyl}piperidin-3-yl]isoxazol-5-yl}butan-2-ol (Example 16) and 3-methyl-2-{3-[(3R,6R)-6-methyl-1-{[2-(2H-1,2,3-triazol-2-yl)phenyl]carbonyl}piperidin-3-yl]isoxazol-5-yl}butan-2-ol (Example 17)

To a solution of compound 27 (Examples 14&15, Step 1) (300 mg, 0.79 mmol) in THF (5 mL) at 0° C. was added i-PrMgBr (0.79 mL, 1.58 mmol). The mixture was stirred at RT overnight, aq. NH$_4$Cl (5 mL) added and the mixture extracted with EtOAc (10 mL×3). The combined organic layers were washed with brine (10 mL), dried over Na$_2$SO$_4$, filtered and the filtrate concentrated in vacuo. The residue was purified by preparative HPLC to give Example 16 (faster eluting isomer in HPLC) as an oil and Example 17 (slower eluting isomer in HPLC) as an oil. Example 16: LRMS m/z (M+H) 424.2 found, 424.2 required. Example 17: LRMS m/z (M+H) 424.2 found, 424.2 required.

EXAMPLE 18

((2S)-1,1-Difluoro-2-{3-[(3R,6R)-6-methyl-1-{[2-(2H-1,2,3-triazol-2-yl)phenyl]carbonyl}piperidin-3-yl]isoxazol-5-yl}propan-2-ol)

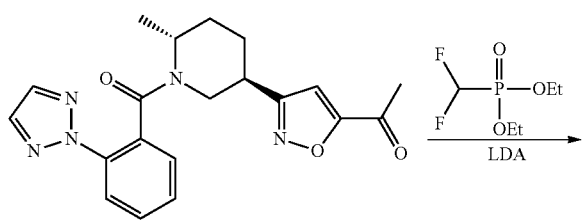

27

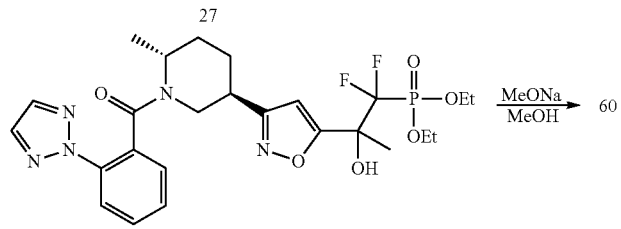

28

-continued

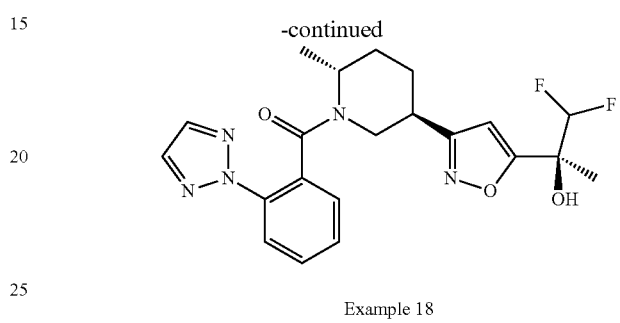

Example 18

Step 1: Diethyl (2-(3-((3R,6R)-1-(2-(2H-1,2,3-triazol-2-yl)benzoyl)-6-methylpiperidin-3-yl)isoxazol-5-yl)-1,1-difluoro-2-hydroxypropyl)phosphonate (28)

To a solution of diethyl difluoromethylphosphonate (99.2 mg, 0.527 mmol) in THF (3.0 mL) at −78° C. was added LDA (0.4 mL, 2M, 0.79 mmol) dropwise. The mixture was stirred at −78° C. for 1 h, and a solution of compound 27 (Examples 14&15, Step 1) (200 mg, 0.527 mmol) in THF (2 mL) was added. The resulting mixture was stirred at RT for 2 h, aq. NH$_4$Cl added and the mixture extracted with EtOAc (20 mL×3). The combined organic layers were washed with brine, dried over Na$_2$SO$_4$, filtered and the filtrate concentrated in vacuo. The residue was purified by preparative HPLC to give the title compound as an oil. LRMS m/z (M+H) 568.2 found, 568.2 required.

Step 2: (2S)-1,1-Difluoro-2-{3-[(3R,6R)-6-methyl-1-{[2-(2H-1,2,3-triazol-2-yl)phenyl]carbonyl}piperidin-3-yl]isoxazol-5-yl}propan-2-ol (Example 18)

To a solution of the product from step 1 (50 mg, 0.09 mmol) in THF (0.2 mL) was added NaOMe in MeOH (0.3 mmol, concentrated in vacuo. The residue was purified by preparative HPLC to give the title compound (only slower eluting isomer in HPLC was received well) as an oil. LRMS m/z (M+H) 432.1 found, 432.2 required.

EXAMPLE 19

((2R,5R)-5-[5-(1-Methoxy-1-methylethyl)isoxazol-3-yl]-2-methyl-1-{[2-(2H-1,2,3-triazol-2-yl)phenyl]carbonyl}piperidine)

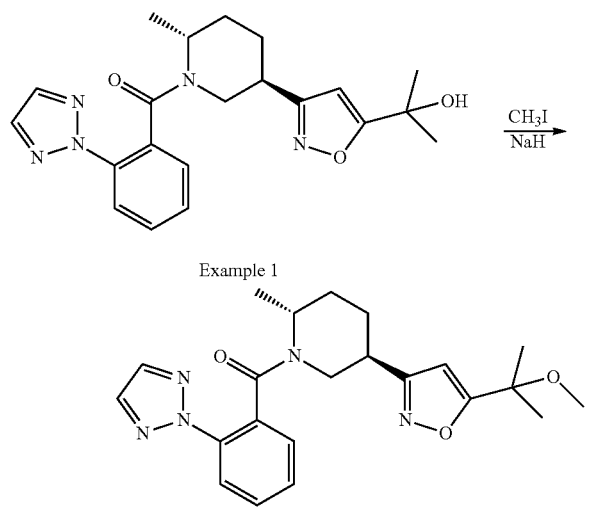

Example 19

(2R,5R)-5-[5-(1-methoxy-1-methylethyl)isoxazol-3-yl]-2-methyl-1-{[2-(2H-1,2,3-triazol-2-yl)phenyl]carbonyl}piperidine (Example 19)

To a solution of Example 1 (50 mg, 0.126 mmol) in DMF (3 mL) at 0° C. was added NaH (7.56 mg, 0.189 mmol, 60 wt. % in oil). The mixture was stirred at 0° C. for 30 min, MeI (17.8 mg, 0.126 mmol) added and the resulting mixture stirred at 0° C. for 1 h. Water (0.5 mL) was added and the mixture purified by preparative HPLC to give the title compound as an oil. LRMS m/z (M+H) 410.2 found, 410.2 required.

EXAMPLE 20

(2-{5-[(3R,6R)-6-Methyl-1-{[2-(2H-1,2,3-triazol-2-yl)phenyl]carbonyl}piperidin-3-yl]isoxazol-3-yl}propan-2-ol)

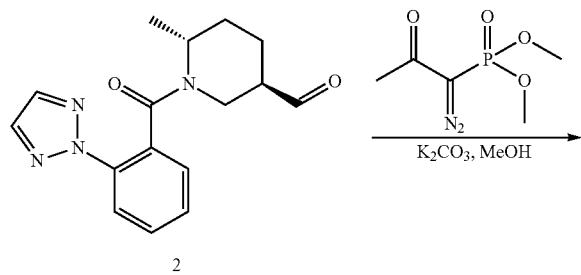

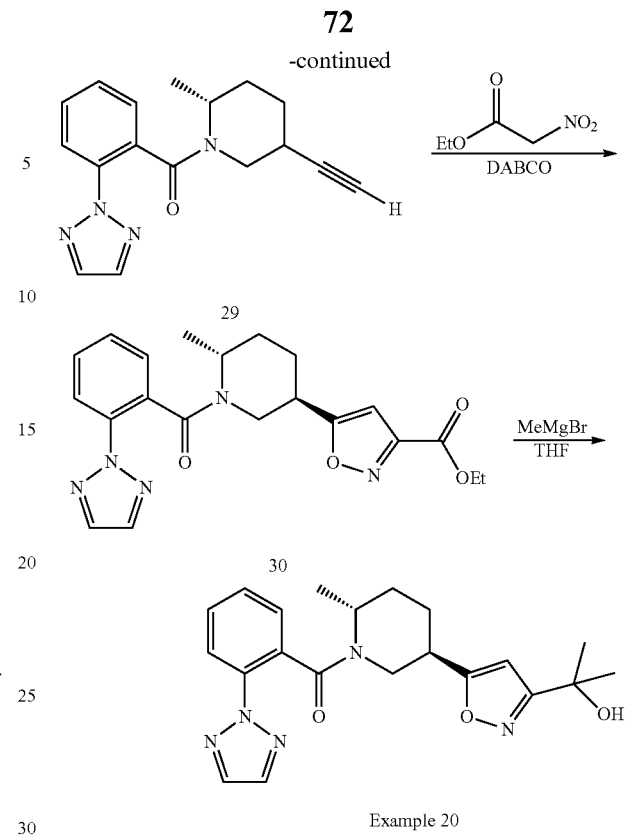

Step 1: (2-(2H-1,2,3-triazol-2-yl)phenyl)((2R)-5-ethynyl-2-methylpiperidin-1-yl)methanone (29)

To a solution of compound 2 (Example 1, Step 2) (2.5 g, 8.3 mmol) in MeOH (250 mL) were added (1-diazo-2-oxopropyl)-phosphonic acid dimethyl ester (1.93 g, 10.06 mmol) and K₂CO₃ (2.29 g, 16.6 mmol). The resulting mixture was stirred at RT overnight, then concentrated in vacuo to remove most of MeOH, diluted with aq. NaHCO₃ (50 mL) and extracted with EtOAc (30 mL×3). The combined organic layers were dried over Na₂SO₄, filtered and the filtrate concentrated in vacuo to give the title compound as an oil. LRMS m/z (M+H) 295.2 found, 295.2 required.

Step 2: Ethyl 5-((3R,6R)-1-(2-(2H-1,2,3-triazol-2-yl)benzoyl)-6-methylpiperidin-3-yl)isoxazole-3-carboxylate (30)

To a solution of the product from step 1 (400 mg, 1.36 mmol) in EtOH (10 mL) was added ethyl 2-nitroacetate (2 mL, 2.72 mmol) and DABCO (299 mg, 1.36 mmol) at RT. The resulting mixture was stirred at 80° C. overnight, cooled to RT and concentrated in vacuo. The residue was purified by preparative TLC to give the title compound as a solid. LRMS m/z (M+H) 410.2 found, 410.2 required.

Step 3: 2-{5-[(3R,6R)-6-Methyl-1-{[2-(2H-1,2,3-triazol-2-yl)phenyl]carbonyl}piperidin-3-yl]isoxazol-3-yl}propan-2-ol (Example 20)

To a solution of the product from step 2 (560 mg, 1.37 mmol) in THF (10 mL) at 0° C. was added CH₃MgBr solution (2.74 mL, 3M, 8.22 mmol). The resulting mixture was allowed to warm up to RT and stirred for additional 12 h, water (5 mL) added and the mixture extracted with EtOAc (10 mL×3). The combined organic layers were washed with brine (5 mL), dried over Na$_2$SO$_4$, filtered and concentrated in vacuo. The residue was purified by preparative HPLC to give the title compound as an oil. LRMS m/z (M+H) 396.2 found, 396.2 required.

EXAMPLE 21

(2-{5-[(3R,6R)-1-{[2-(Methoxymethyl)phenyl]carbonyl}-6-methylpiperidin-3-yl]isoxazol-3-yl}propan-2-ol)

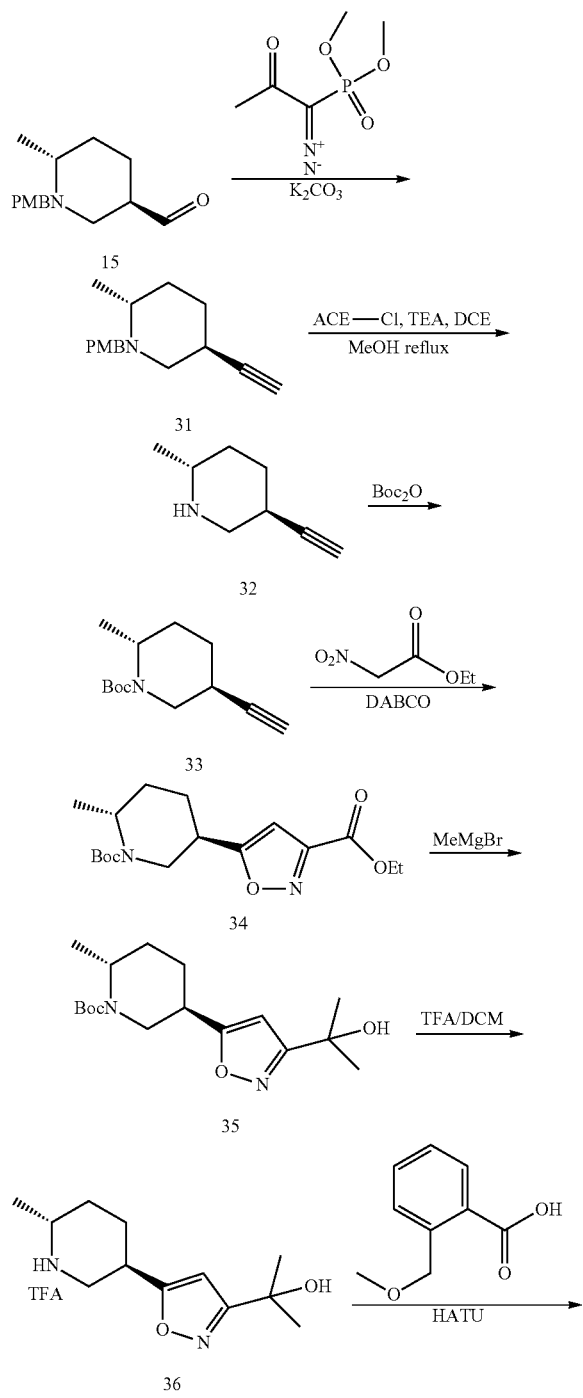

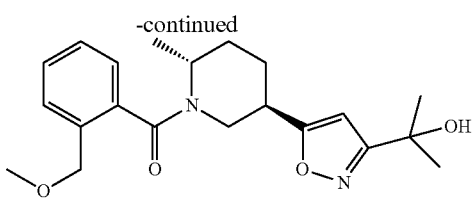

Example 21

Step 1: (2R,5S)-5-Ethynyl-1-(4-methoxybenzyl)-2-methylpiperidine (31)

To a suspension of compound 15 (Example 6, Step 2) (3.2 g, 12.96 mmol) and K$_2$CO$_3$ (4.5 g, 32.4 mmol) in MeOH (40 mL) at RT was added (1-diazo-2-oxo-propyl)-phosphonic acid dimethyl ester (3.7 g, 19.44 mmol). The mixture was stirred at RT overnight, concentrated in vacuo to remove most of MeOH, poured into water (50 mL) and extracted with DCM (60 mL×3). The combined organic layers were washed with water (50 mL) and brine (50 mL), dried over Na$_2$SO$_4$, filtered and concentrated in vacuo. The residue was purified by chromatography on silica (10% EtOAc in petroleum ether) to give the title compound as a solid. LRMS m/z (M+H) 244.2 found, 244.2 required.

Step 2: (2R,5S)-5-ethynyl-2-methylpiperidine (32)

A solution of the product from step 1 (1 g, 4.12 mmol) and ACE-Cl (1.2 g, 8.24 mmol) in DCE (10 mL) was heated to reflux overnight. TEA (400 mg, 3.96 mmol) was added and the mixture heated to reflux for an additional 1 h. The cooled mixture was concentrated in vacuo, the residue dissolved in MeOH (10 mL), heated to reflux for 1 h, cooled and concentrated in vacuo. The residue was poured into water (50 mL) and extracted with DCM (60 mL×3). The combined organic layers were washed with water (50 mL) and brine (50 mL), dried over Na$_2$SO$_4$, filtered and concentrated in vacuo to give the title compound as a solid. 124.2 found, 124.2 required.

Step 3: (2R,5S)-tert-Butyl 5-ethynyl-2-methylpiperidine-1-carboxylate (33)

A solution of the product from step 2 (500 mg, 4.06 mmol) in 1 M of NaOH (10 mL) and THF (10 mL) was treated with Boc$_2$O (1.8 g, 8.13 mmol). The mixture was stirred at RT for 0.5 h, poured into water (30 mL), and extracted with EtOAc (60 mL×3). The combined organic layers were washed with water (50 mL) and brine (50 mL), dried over Na$_2$SO$_4$, filtered and concentrated in vacuo. The residue was purified by chromatography on silica (10% EtOAc in petroleum ether) to give the title compound as an oil. LRMS m/z (M+H−56) 168.2 found, 168.2 required.

Step 4: Ethyl 5-((3R,6R)-1-(tert-butoxycarbonyl)-6-methylpiperidin-3-yl)isoxazole-3-carboxylate (34)

A solution of the product from step 3 (800 mg, 3.6 mmol), ethyl 2-nitroacetate (2.8 g, 21.6 mmol) in EtOH (10 mL) at RT was added DABCO (200 mg, 1.8 mmol). The mixture was heated to reflux overnight, cooled and concentrated in vacuo. The residue was poured into water (30 mL) and extracted with DCM (60 mL×3). The combined organic layers were washed with water (50 mL) and brine (40 mL), dried over Na$_2$SO$_4$, filtered and concentrated in vacuo. The residue was purified by chromatography on silica (10% EtOAc in petroleum ether) to give the title compound as an oil. LRMS m/z (M+H−56) 283.2 found, 283.2 required.

Step 5: (2R,5R)-tert-Butyl 5-(3-(2-hydroxypropan-2-yl)isoxazol-5-yl)-2-methylpiperidine-1-carboxylate (35)

A solution of the product from step 4 (600 mg, 1.78 mmol) in THF (10 mL) was treated with MeMgBr (1.5 mL, 3M, 4.43 mmol) at 0° C. The mixture was allowed to warm up to RT for 3 h, sat. aqueous NH$_4$Cl solution (10 mL) added and the mixture extracted with EtOAc (30 mL×3). The combined organic layers were washed with water (20 mL) and brine (20 mL), dried over Na$_2$SO$_4$, filtered and concentrated in vacuo. The residue was purified by chromatography on silica (30% EtOAc in petroleum ether) to give the title compound as an oil. LRMS m/z (M+H−56) 269.2 found, 269.2 required.

Step 6: 2-(5-((3R,6R)-6-Methylpiperidin-3-yl)isoxazol-3-yl)propan-2-ol TFA salt (36)

A solution of the product from step 5 (300 mg, 0.73 mmol) in TFA/DCM (1 mL/4 mL) was stirred at RT for 3 h and concentrated in vacuo to give the title compound as an oil. LRMS m/z (M+H) 225.2 found, 225.2 required.

Step 7: 2-{5-[(3R,6R)-1-{[2-(Methoxymethyl)phenyl]carbonyl}-6-methylpiperidin-3-yl]isoxazol-3-yl}propan-2-ol (Example 21)

To a solution of the product from step 6 (30 mg, 0.09 mmol) and 2-methoxymethylbenzoic acid (23 mg, 0.14 mmol) and TEA (0.5 mL) in DMF (3 mL) at RT was added HATU (105 mg, 0.28 mmol). The mixture was stirred at RT for 16 h and purified directly by preparative HPLC to give the title compound as a solid. LRMS m/z (M+H) 373.2 found, 373.2 required.

EXAMPLES 22-38

Examples 22-38 shown in the following table were prepared according to the methodology herein and the general procedure provided in Example 21. The starting materials are either commercially available or may be prepared as described in the intermediates preparation section, or may be prepared from commercially available reagents using conventional reactions well known in the art.

| Example # | R | Chemical Name | LRMS or HRMS (M + H⁺) |
|---|---|---|---|
| 22 | 2-pyrimidin-2-ylphenyl-C(O)- | 2-(5-{(3R,6R)-6-Methyl-1-[(2-pyrimidin-2-ylphenyl)carbonyl]piperidin-3-yl}isoxazol-3-yl)propan-2-ol | Calc'd 407.2, found 407.2 |
| 23 | 2-ethoxypyridin-3-yl-C(O)- | 2-(5-{(3R,6R)-1-[(2-Ethoxypyridin-3-yl)carbonyl]-6-methylpiperidin-3-yl}isoxazol-3-yl)propan-2-ol | Calc'd 374.2, found 374.2 |
| 24 | 5-fluoro-2-(2H-1,2,3-triazol-2-yl)phenyl-C(O)- | 2-{5-[(3R,6R)-1-{[5-Fluoro-2-(2H-1,2,3-triazol-2-yl)phenyl]carbonyl}-6-methylpiperidin-3-yl]isoxazol-3-yl}propan-2-ol | Calc'd 414.2, found 414.2 |

-continued

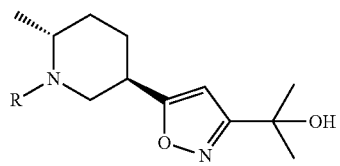

| Example # | R | Chemical Name | LRMS or HRMS (M + H+) |
|---|---|---|---|
| 25 | pyrazinyl-pyrazolyl ketone | 2-{5-[(3R,6R)-6-methyl-1-{[3-(1H-pyrazol-1-yl)pyrazin-2-yl]carbonyl}piperidin-3-yl]isoxazol-3-yl}propan-2-ol | Calc'd 397.2, found 397.2 |
| 26 | biphenyl ketone | 2-{5-[(3R,6R)-1-(Biphenyl-2-ylcarbonyl)-6-methylpiperidin-3-yl]isoxazol-3-yl}propan-2-ol | Calc'd 405.2, found 405.2 |
| 27 | 5-chloro-2-(triazol-2-yl)phenyl ketone | 2-{5-[(3R,6R)-1-{[5-Chloro-2-(2H-1,2,3-triazol-2-yl)phenyl]carbonyl}-6-methylpiperidin-3-yl]isoxazol-3-yl}propan-2-ol | Calc'd 430.2, found 430.1 |
| 28 | pyrazinyl-pyridyl ketone | 2-(5-{(3R,6R)-6-Methyl-1-[(3-pyridin-2-ylpyrazin-2-yl)carbonyl]piperidin-3-yl}isoxazol-3-yl)propan-2-ol | Calc'd 408.2, found 408.2 |
| 29 | 2-(1-cyanocyclopropyl)phenyl ketone | 1-[2-({(2R,5R)-5-[3-(1-Hydroxy-1-methylethyl)isoxazol-5-yl]-2-methylpiperidin-1-yl}carbonyl)phenyl]cyclopropane carbonitrile | Calc'd 394.2, found 394.2 |
| 30 | 2-(methoxycarbonyl)phenyl ketone | Methyl 2-({(2R,5R)-5-[3-(1-hydroxy-1-methylethyl)isoxazol-5-yl]-2-methylpiperidin-1-yl}carbonyl)benzoate | Calc'd 387.2, found 387.2 |

-continued

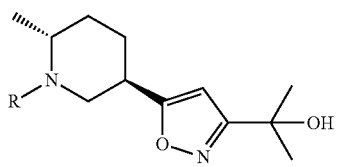

| Example # | R | Chemical Name | LRMS or HRMS (M + H+) |
|---|---|---|---|
| 31 | 2-ethoxyphenyl carbonyl group | 2-(5-{(3R,6R)-1-[(2-Ethoxyphenyl)carbonyl]-6-methylpiperidin-3-yl}isoxazol-3-yl)propan-2-ol | Calc'd 373.2, found 373.2 |
| 32 | 2-(2H-tetrazol-2-yl)phenyl carbonyl group | 2-{5-[(3R,6R)-6-Methyl-1-{[2-(2H-tetrazol-2-yl)phenyl]carbonyl}piperidin-3-yl]isoxazol-3-yl}propan-2-ol | Calc'd 397.2, found 397.2 |
| 33 | 2-phenylpyridin-3-yl carbonyl group | 2-(5-{(3R,6R)-6-Methyl-1-[(2-phenylpyridin-3-yl)carbonyl]piperidin-3-yl}isoxazol-3-yl)propan-2-ol | Calc'd 406.2, found 406.2 |
| 34 | 3-phenylpyridin-2-yl carbonyl group | 2-(5-{(3R,6R)-6-Methyl-1-[(3-phenylpyridin-2-yl)carbonyl]piperidin-3-yl}isoxazol-3-yl)propan-2-ol | Calc'd 406.2, found 406.2 |
| 35 | 2-(2,2-difluoroethoxy)phenyl carbonyl group | 2-{5-[(3R,6R)-1-{[2-(2,2-Difluoroethoxy)phenyl]carbonyl}-6-methylpiperidin-3-yl]isoxazol-3-yl}propan-2-ol | Calc'd 409.2, found 409.2 |
| 36 | 2-(2,2,2-trifluoroethoxy)phenyl carbonyl group | 2-{5-[(3R,6R)-6-Methyl-1-{[2-(2,2,2-trifluoroethoxy)phenyl]carbonyl}piperidin-3-yl]isoxazol-3-yl}propan-2-ol | Calc'd 427.2, found 427.1 |

| Example # | R | Chemical Name | LRMS or HRMS (M + H⁺) |
|---|---|---|---|
| 37 | | 2-(5-{(3R,6R)-6-Methyl-1-[(2-pyrazin-2-ylphenyl)carbonyl]piperidin-3-yl}isoxazol-3-yl)propan-2-ol | Calc'd 407.2, found 407.2 |
| 38 | | 2-{5-[(3R,6R)-1-{[2-(2,2-Difluorocyclopropyl)phenyl]carbonyl}-6-methylpiperidin-3-yl]isoxazol-3-yl}propan-2-ol | Calc'd 405.2, found 405.1 |
EXAMPLE 39
(2-{5-[(3R,6R)-6-Ethyl-1-{[2-(2H-1,2,3-triazol-2-yl)phenyl]carbonyl}piperidin-3-yl]isoxazol-3-yl}propan-2-ol)
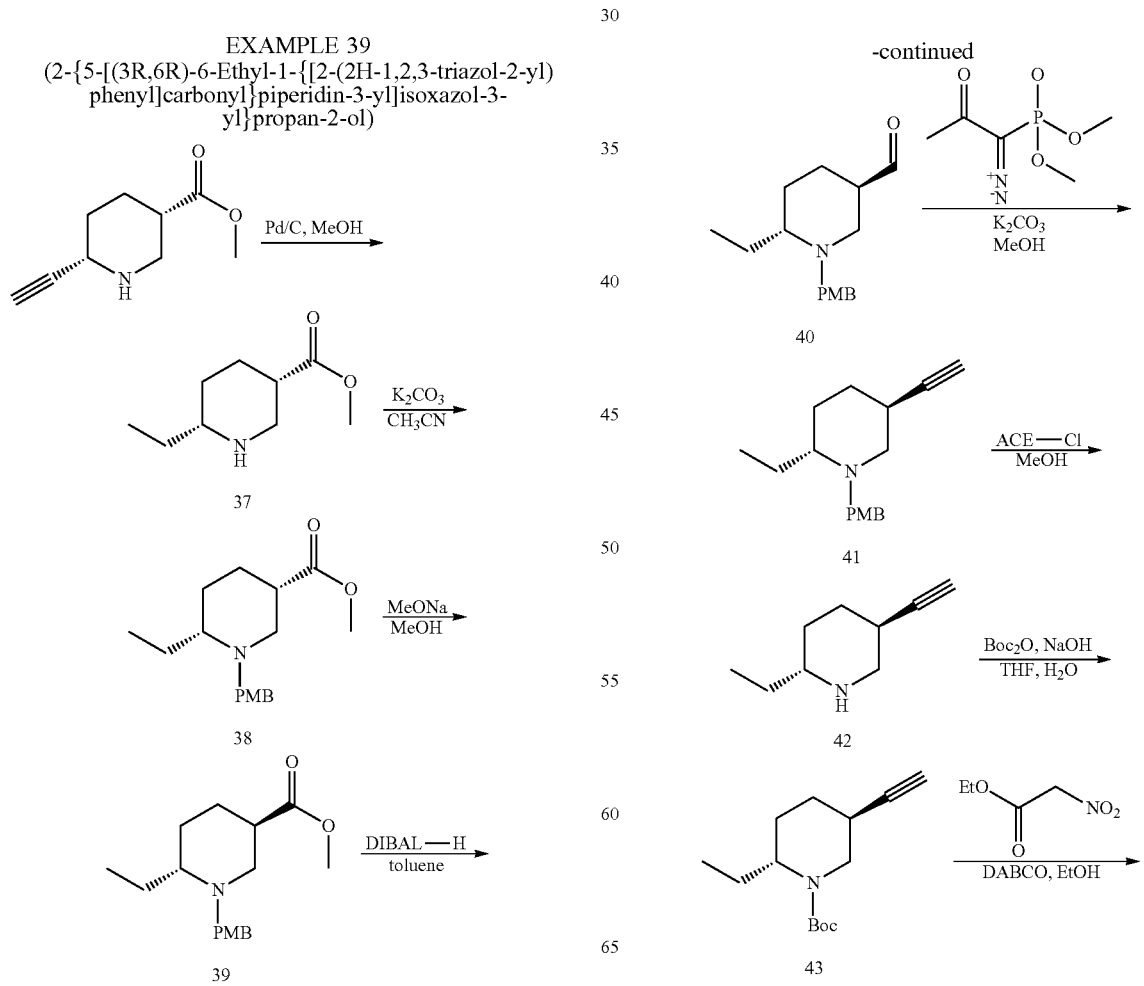

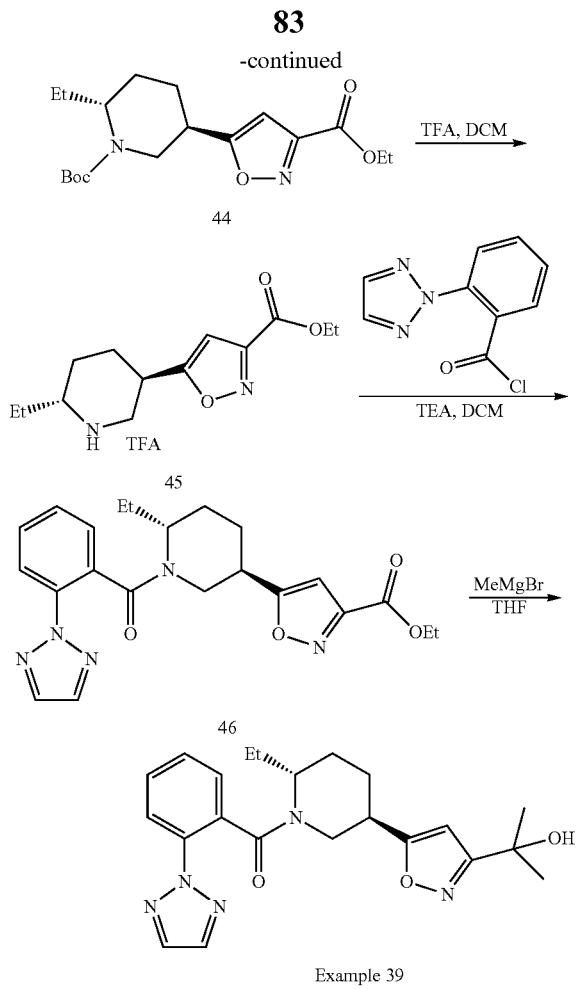

Example 39

Step 1: (3S,6R)-Methyl 6-ethylpiperidine-3-carboxylate (37)

To a solution (3S,6S)-methyl 6-ethynylpiperidine-3-carboxylate (3.0 g, 18.0 mmol) in 30 mL of MeOH was added Pd/C (300 mg). The mixture was stirred under 1 atm of H₂ at RT for 2 h, filtered and concentrated in vacuo to give the title compound as an oil, which was used directly in the next step. LRMS m/z (M+H) 172.2 found, 172.2 required.

Step 2: (3S,6R)-Methyl 6-ethyl-1-(4-methoxybenzyl)piperidine-3-carboxylate (38)

A mixture of the product from step 1 (2.9 g, 17.0 mmol), 1-(chloromethyl)-4-methoxybenzene (2.6 g, 17.0 mmol) and K₂CO₃ (4.7 g, 34.0 mmol) in CH₃CN (30 mL) was heated to 50° C. for 3 h, cooled to RT, filtered, and the filtrate concentrated in vacuo. The residue was purified by chromatography on silica (10% EtOAc in petroleum ether) to give the title compound as an oil. LRMS m/z (M+H) 292.2 found, 292.2 required.

Step 3: (3R,6R)-Methyl 6-ethyl-1-(4-methoxybenzyl)piperidine-3-carboxylate (39)

To a freshly prepared solution of CH₃ONa from Na (0.43 g, 18.9 mmol) in MeOH (15 mL) was added the product from step 2 (2.2 g, 7.56 mmol). The resulting mixture was stirred at 50° C. overnight, cooled to RT, poured into water (50 mL), and extracted with EtOAc (30 mL×3). The combined organic layers were dried over Na₂SO₄, filtered and the filtrate concentrated in vacuo. The crude product was purified by chromatography on silica (10% EtOAc in petroleum ether) to give the title compound as an oil. LRMS m/z (M+H) 292.2 found, 292.2 required.

Step 4: (3R,6R)-6-Ethyl-1-(4-methoxybenzyl)piperidine-3-carbaldehyde (40)

To a solution of the product from step 3 (1.7 g, 5.8 mmol) in toluene (10 mL) −78° C. was added DIBAL-H (8.8 mL, 1M, 8.8 mmol) dropwise. The resulting mixture was stirred at the RT for 3 h, quenched by slow addition of MeOH (20 mL) at −78° C., warmed to RT and the solution was used for the next step directly. LRMS m/z (M+H) 262.3 found, 262.2 required.

Step 5: (2R,5S)-2-Ethyl-5-ethynyl-1-(4-methoxybenzyl)piperidine (41)

To the solution from step 4 was added K₂CO₃ (1.6 g, 11.6 mmol) and (1-diazo-2-oxo-propyl)-phosphonic acid dimethyl ester (1.7 g, 8.8 mmol) at RT. The mixture was stirred overnight and concentrated in vacuo. The residue was partitioned between EtOAc (50 mL) and H₂O (30 mL). The organic layer was collected and the aqueous layer was extracted with EtOAc (50 mL×2). The combined organic layers were washed with brine (50 mL) and dried over Na₂SO₄, filtered and concentrated in vacuo. The residue was purified by chromatography on silica (5% EtOAc in petroleum ether) to give the title compound as an oil. LRMS m/z (M+H) 258.2 found, 258.2 required.

Step 6: (2R,5S)-2-Ethyl-5-ethynylpiperidine (42)

A solution of the product from step 5 (375 mg, 1.29 mmol) and ACE-Cl (737 mg, 5.15 mmol) in DCE (4 mL) was heated to reflux overnight, cooled and concentrated in vacuo. The residue was dissolved in MeOH (5 mL), refluxed for 1 h, cooled, concentrated in vacuo, the residue poured into water (20 mL), and extracted with DCM (20 mL×3). The combined organic layers were washed with water (20 mL) and brine (30 mL), dried over Na₂SO₄, filtered and concentrated in vacuo to give the title compound as an oil. LRMS m/z (M+H) 138.2 found, 138.2 required.

Step 7: (2R,5S)-tert-Butyl 2-ethyl-5-ethynylpiperidine-1-carboxylate (43)

To a solution of the product from step 6 (120 mg, 0.88 mmol) in 1 M of NaOH (5 mL) and THF (50 mL) was added Boc₂O (210 mg, 0.96 mmol). The mixture was stirred at RT for 0.5 h, poured into water (20 mL), and extracted with EtOAc (20 mL×3). The combined organic layers were washed with brine (30 mL), dried over Na₂SO₄, filtered and concentrated in vacuo. The residue was purified by preparative TLC (17% EtOAc in petroleum ether) to give the title compound as an oil. LRMS m/z (M+H) 238.2 found, 238.2 required.

Step 8: Ethyl 5-((3R,6R)-1-(tert-butoxycarbonyl)-6-ethylpiperidin-3-yl)isoxazole-3-carboxylate (44)

To a solution of the product from step 7 (162 mg, 0.68 mmol), ethyl 2-nitroacetate (272 mg, 2.05 mmol) in EtOH (10 mL) at RT was added DABCO (76 mg, 0.68 mmol). The resulting mixture was heated to reflux overnight, cooled and concentrated in vacuo. The residue was poured into water (10 mL), and extracted with DCM (20 mL×3). The combined organic layers were washed with brine (40 mL), dried over Na$_2$SO$_4$, filtered and concentrated in vacuo. The residue was purified by preparative TLC (17% EtOAc in petroleum ether) to give the title compound as a solid. LRMS m/z (M+H) 353.2 found, 353.2 required.

Step 9: Ethyl 5-((3R,6R)-6-ethylpiperidin-3-yl)isoxazole-3-carboxylate TFA salt (45)

A solution of the product from step 8 (40 mg, 0.11 mmol) in trifluoroacetic acid /dichloromethane (0.5 mL/5 mL) was stirred at RT for 0.5 h. and concentrated in vacuo to give the title compound as a solid. LRMS m/z (M+H) 253.3 found, 253.2 required.

Step 10: Ethyl 5-((3R,6R)-1-(2-(2H-1,2,3-triazol-2-yl)benzoyl)-6-ethylpiperidin-3-yl)isoxazole-3-carboxylate (46)

To a solution of the product from step 9 (29 mg, 0.08 mmol) and TEA (23 mg, 0.22 mmol) in DCM (20 mL) at 0° C. was dropwise added 2-(2H-1, 2, 3-triazol-2-yl) benzoyl chloride (26 mg, 0.13 mmol). The resulting mixture was stirred at RT for 1 h, concentrated in vacuo and the residue purified by preparative TLC (50% EtOAc in petroleum ether) to give the title compound as a solid. LRMS m/z (M+H) 424.2 found, 424.2 required.

Step 11: 2-{5-[(3R,6R)-6-Ethyl-1-{[2-(2H-1,2,3-triazol-2-yl)phenyl]carbonyl}piperidin-3-yl]isoxazol-3-yl}propan-2-ol (39)

To a solution of the product from step 10 (40 mg, 0.09 mmol) in dry THF (1 mL) at 0° C. was added MeMgBr solution (0.13 mL, 3M, 0.37 mmol) dropwise. The resulting mixture was stirred at RT for 1 h, sat. NH$_4$Cl solution (10 mL) added and the mixture extracted with EtOAc (10 mL×3). The combined organic layers were dried over Na$_2$SO$_4$, filtered and concentrated in vacuo. The residue was purified by preparative HPLC to give the title compound as a solid. LRMS m/z (M+H) 410.2 found, 410.2 required.

EXAMPLES 40 and 41

((1R)-2,2,2-Trifluoro-1-{5-[(3R,6R)-6-methyl-1-{[2-(2H-1,2,3-triazol-2-yl)phenyl]carbonyl}piperidin-3-yl]isoxazol-3-yl}ethanol) (Ex. 40) and ((1S)-2,2,2-Trifluoro-1-{5-[(3R,6R)-6-methyl-1-{[2-(2H-1,2,3-triazol-2-yl)phenyl]carbonyl}piperidin-3-yl]isoxazol-3-yl}ethanol) (Ex. 41)

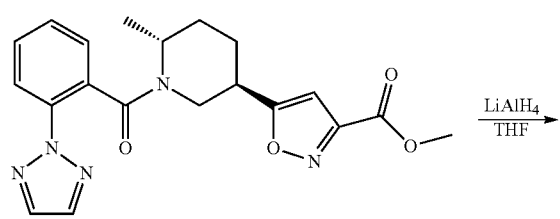

30

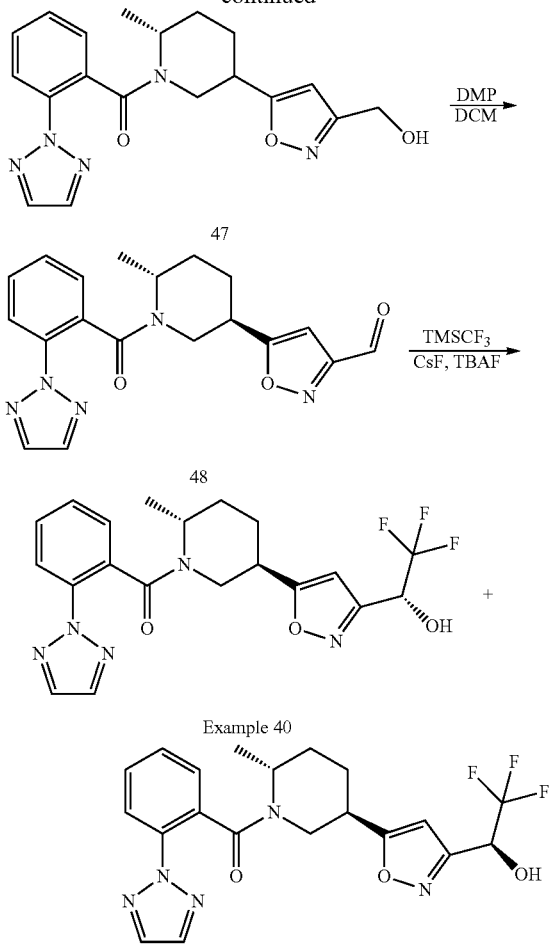

Step 1: (2-(2H-1,2,3-Triazol-2-yl)phenyl)((2R)-5-(3-(hydroxymethyl)isoxazol-5-yl)-2-methylpiperidin-1-yl)methanone (47)

To a solution of compound 30 (Example 20, Step 2) (200 mg, 0.488 mmol) in THF (54 mL) at 0° C. was added LiAlH$_4$ (37 mg, 0.977 mmol) in portions. The reaction mixture was stirred at 0° C. for 2 h, water (0.1 mL) added, the mixture stirred for 10 min, dried over Na$_2$SO$_4$, filtered and concentrated in vacuo. The residue was purified by preparative HPLC to give the title compound as an oil. LRMS m/z (M+H) 368.1 found, 368.2 required.

Step 2: 5-((3R,6R)-1-(2-(2H-1,2,3-Triazol-2-yl)benzoyl)-6-methylpiperidin-3-yl)isoxazole-3-carbaldehyde (48)

To a solution of the product from step 1 (700 mg, 1.9 mmol) in DCM (10 mL) was added DMP (1.6 g, 3.8 mmol). The resulting mixture was stirred at RT for 4 h, diluted with water (10 mL) and extracted with DCM (10 mL×3). The combined organic layers were dried over Na$_2$SO$_4$, filtered and concentrated in vacuo to give the title compound as an oil. LRMS m/z (M+H) 366.1 found, 366.2 required.

Step 3: (1R)-2,2,2-Trifluoro-1-{5-[(3R,6R)-6-methyl-1-{[2-(2H-1,2,3-triazol-2-yl)phenyl]carbonyl}piperidin-3-yl]isoxazol-3-yl}ethanol (Example 40) and (1S)-2,2,2-trifluoro-1-{5-[(3R,6R)-6-methyl-1-{[2-(2H-1,2,3-triazol-2-yl)phenyl]carbonyl}piperidin-3-yl]isoxazol-3-yl}ethanol (Example 41)

To a solution of the product from step 2 (100 mg, 0.282 mmol) in dry THF (5 mL) at 0° C. were added CsF (62 mg, 0.41 mmol) and TMSCF₃ (350 mg, 2.46 mmol). The resulting mixture was stirred at 0° C. for 1 h, TBAF (300 mg) added and stirring at RT continued for 1 hour, then concentrated in vacuo. The residue was purified by preparative HPLC to give Example 40 (faster eluting isomer in HPLC) as an oil and Example 41 (slower eluting isomer in HPLC) as an oil. Example 40: LRMS m/z (M+H) 436.1 found, 436.2 required. Example 41: LRMS m/z (M+H) 436.1 found, 436.2 required.

EXAMPLES 42 and 43

((1R)-2,2,2-Trifluoro-1-{5-[(3R,6R)-6-methyl-1-{[2-(2H-1,2,3-triazol-2-yl)thiophen-3-yl]carbonyl}piperidin-3-yl]isoxazol-3-yl}ethanol) (Ex. 42) and ((1S)-2,2,2-Trifluoro-1-{5-[(3R,6R)-6-methyl-1-{[2-(2H-1,2,3-triazol-2-yl)thiophen-3-yl]carbonyl}piperidin-3-yl]isoxazol-3-yl}ethanol) (Ex. 43)

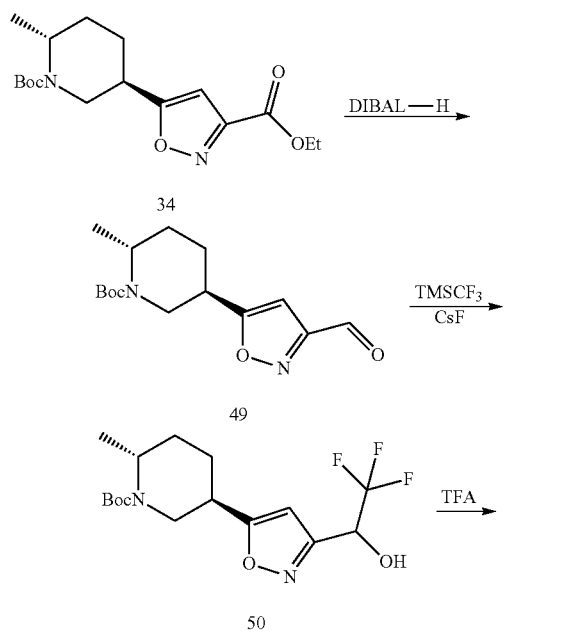

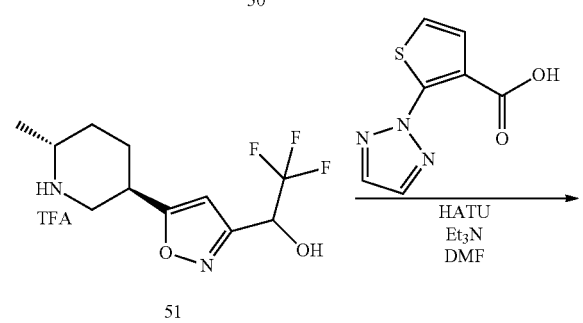

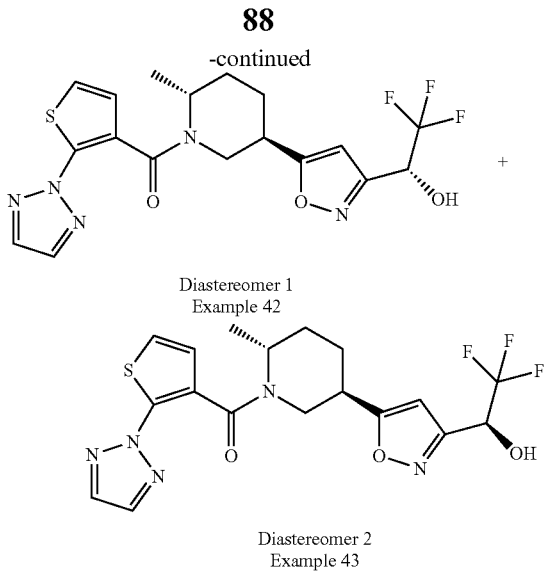

Diastereomer 1
Example 42

Diastereomer 2
Example 43

Step 1: (2R,5R)-tert-Butyl 5-(3-formylisoxazol-5-yl)-2-methylpiperidine-1-carboxylate (49)

To a solution of compound 34 (Example 21, Step 4) (300 mg, 0.89 mmol) in toluene (5 mL) at −78° C. was added DIBAL-H (4.4 mL, 4.4 mmol) dropwise. The resulting mixture was stirred at −78° C. for 3.5 h, MeOH (10 mL) added carefully and the mixture filtered through a celite pad and concentrated in vacuo. The residue was purified by chromatography on silica (3% EtOAc in petroleum ether) to give the tile compound as an oil. LRMS m/z (M+H) 295.0 found, 295.2 required.

Step 2: (2R,5R)-tert-Butyl 2-methyl-5-(3-(2,2,2-trifluoro-1-hydroxyethyl)isoxazol-5-yl)piperidine-1-carboxylate (50)

To a mixture of the product from step 1 (130 mg, 0.44 mmol) and CsF (66 mg, 0.44 mmol) in THF (5 mL) was added TMSCF₃ (172 mg, 1.32 mmol) at 0° C. The resulting mixture was stirred at 0° C. for 1 h water (10 mL) was added and the mixture extracted with EtOAc (30 mL×3). The combined organic layers were washed with water (20 mL) and brine (20 mL), dried over Na₂SO₄, filtered and concentrated in vacuo. The residue was purified by preparative TLC (25% EtOAc in petroleum ether) to give the title compound as an oil. LRMS m/z (M+H) 365.2 found, 365.2 required.

Step 3: 2,2,2-Trifluoro-1-(5-((3R,6R)-6-methylpiperidin-3-yl)isoxazol-3-yl)ethanol TFA salt (51)

A solution of the product from step 2 (80 mg, 0.22 mmol) in TFA/DCM (0.5 mL/3 mL) was stirred at RT for 1 h and concentrated in vacuo to give the title compound as a solid. LRMS m/z (M+H) 265.2 found, 265.2 required.

Step 4: (1R)-2,2,2-Trifluoro-1-{5-[(3R,6R)-6-methyl-1-{[2-(2H-1,2,3-triazol-2-yl)thiophen-3-yl]carbonyl}piperidin-3-yl]isoxazol-3-yl}ethanol (Example 42) and (1S)-2,2,2-trifluoro-1-{5-[(3R,6R)-6-methyl-1-{[2-(2H-1,2,3-triazol-2-yl)thiophen-3-yl]carbonyl}piperidin-3-yl]isoxazol-3-yl}ethanol (Example 43)

To a solution of the product from step 3 (45 mg, 0.12 mmol), 2-[1,2,3]triazol-2-yl-thiophene-3-carboxylic acid (32 mg, 0.17 mmol) and TEA (0.5 mL) in DMF (3 mL) at RT was added HATU (129 mg, 0.34 mmol). The resulting mixture was stirred at RT for 16 h and purified directly by preparative HPLC, and then chiral SFC HPLC to give Example 42 (faster eluting isomer in SFC) as an oil and Example 43 (slower eluting isomer in SFC) as an oil. Example 42: LRMS m/z (M+H) 442.1 found, 442.1 required. Example 43: LRMS m/z (M+H) 442.1 found, 442.1 required.

EXAMPLES 44 to 47

Examples 44-47 in the following table were prepared according to the methodology herein and the general procedure provided in Example 42 and 43. The starting materials are either commercially available or may be prepared as described in the intermediates preparation section, or may be prepared from commercially available reagents using conventional reactions well known in the art.

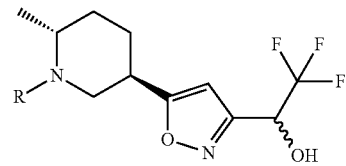

(product may be racemic)

| Example # | R | Chemical Name | LRMS or HRMS (M + H⁺) |
|---|---|---|---|
| 44 | (2-cyanocyclopropyl-phenyl-carbonyl group) | 1-(2-{[(2R,5R)-2-Methyl-5-{3-[(1R)-2,2,2-Trifluoro-1-hydroxyethyl]isoxazol-5-yl}piperidin-1-yl]carbonyl}phenyl)cyclopropanecarbonitrile | Calc'd 434.2, found 434.1 |
| 45 | (2-cyanocyclopropyl-phenyl-carbonyl group) | 1-(2-{[(2R,5R)-2-Methyl-5-{3-[(1S)-2,2,2-trifluoro-1-hydroxyethyl]isoxazol-5-yl}piperidin-1-yl]carbonyl}phenyl)cyclopropanecarbonitrile | Calc'd 434.2, found 434.1 |
| 46 | (2-tetrazolyl-phenyl-carbonyl group) | (1R)-2,2,2-Trifluoro-1-{5-[(3R,6R)-6-methyl-1-{[2-(2H-tetrazol-2-yl)phenyl]carbonyl}piperidin-3-yl]isoxazol-3-yl}ethanol | Calc'd 437.2, found 437.1 |
| 47 | (2-tetrazolyl-phenyl-carbonyl group) | (1S)-2,2,2-Trifluoro-1-{5-[(3R,6R)-6-methyl-1-{[2-(2H-tetrazol-2-yl)phenyl]carbonyl}piperidin-3-yl]isoxazol-3-yl}ethanol | Calc'd 437.2, found 437.1 |

EXAMPLES 48 and 49

((1S)-2,2,2-Trifluoro-1-(5-{(3R,6R)-6-methyl-1-[(2-pyrimidin-2-ylthiophen-3-yl)carbonyl]piperidin-3-yl}isoxazol-3-yl)ethanol) (Ex. 48) and ((1R)-2,2,2-Trifluoro-1-(5-{(3R,6R)-6-methyl-1-[(2-pyrimidin-2-ylthiophen-3-yl)carbonyl]piperidin-3-yl}isoxazol-3-yl)ethanol) (Ex. 49)

(1S)-2,2,2-Trifluoro-1-(5-{(3R,6R)-6-methyl-1-[(2-pyrimidin-2-ylthiophen-3-yl)carbonyl]piperidin-3-yl}isoxazol-3-yl)ethanol (Example 48) and (1R)-2,2,2-trifluoro-1-(5-{(3R,6R)-6-methyl-1-[(2-pyrimidin-2-ylthiophen-3-yl)carbonyl]piperidin-3-y}isoxazol-3-yl)ethanol (Example 49)

A solution of 2-pyrimidin-2-yl-thiophene-3-carboxylic acid (31 mg, 0.15 mmol) and SOCl₂ (0.5 mL) in toluene (5 mL) was heated to reflux for 30 min, cooled to RT and concentrated in vacuo. The residue was dissolved in toluene (2 mL), which was dropwise added to a solution of compound 51 (Examples 42&43, Step 3) (40 mg, 0.11 mmol) and TEA (0.5 mL) in toluene (2 mL). The resulting mixture was stirred for 1 h and purified directly by preparative HPLC, and then chiral SFC HPLC to give Example 48 (faster eluting isomer in SFC) as an oil and Example 49 (slower eluting isomer in SFC) as an oil. Example 48: LRMS m/z (M+H) 453.1 found, 453.1 required. Example 49: LRMS m/z (M+H) 453.1 found, 453.1 required.

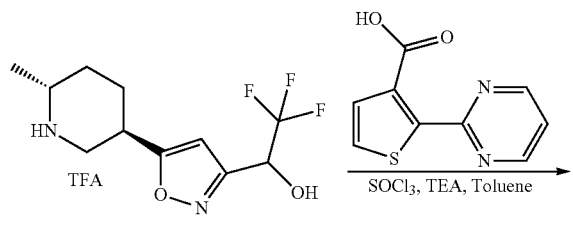

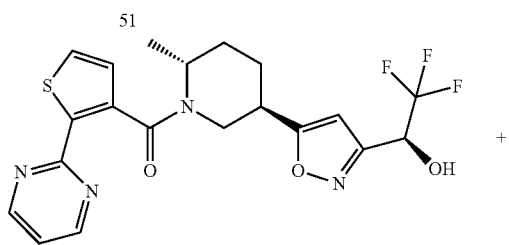

Example 48

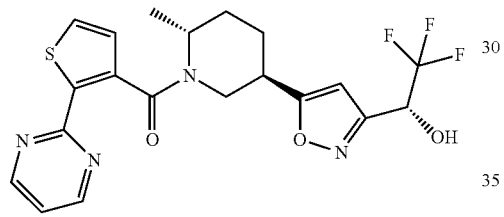

Example 49

EXAMPLES 50 and 51

((1R)-2,2,2-Trifluoro-1-(5-{(3R,6R)-6-methyl-1-[(2-pyrimidin-2-ylphenyl)carbonyl]piperidin-3-yl}isoxazol-3-yl)ethanol) (Ex. 50) and ((1S)-2,2,2-Trifluoro-1-(5-{(3R,6R)-6-methyl-1-[(2-pyrimidin-2-ylphenyl)carbonyl]piperidin-3-yl}isoxazol-3-yl)ethanol) (Ex. 51)

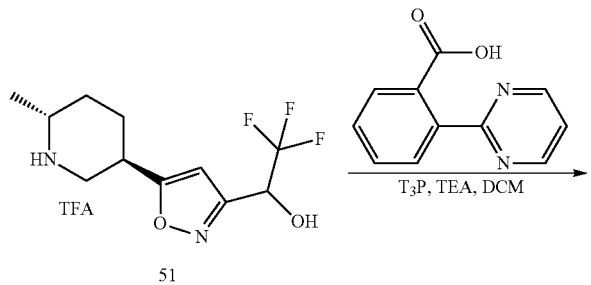

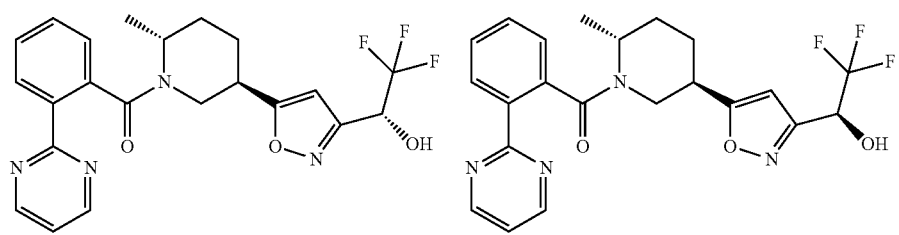

Example 50     Example 51

93

((1R)-2,2,2-Trifluoro-1-(5-{(3R,6R)-6-methyl-1-[(2-pyrimidin-2-ylphenyl)carbonyl]piperidin-3-yl}isoxazol-3-yl)ethanol (Example 50) and (1S)-2,2,2-trifluoro-1-(5-{(3R,6R)-6-methyl-1-[(2-pyrimidin-2-ylphenyl)carbonyl]piperidin-3-yl}isoxazol-3-yl)ethanol (Example 51)

To a solution of compound 51 (Examples 42&43, Step 3) (45 mg, 0.12 mmol) and 2-pyrimidin-2-yl-benzoic acid (34 mg, 0.17 mmol) and TEA (0.5 mL) in DCM (5 mL) at 0° C. was added T$_3$P (0.5 mL). The mixture was heated to 50° C. for 16 h, cooled, water (1 mL) added and the mixture concentrated in vacuo. The residue was purified by preparative HPLC, and then chiral SFC HPLC to give Example 50 (faster eluting isomer in SFC) as a solid and Example 51 (slower eluting isomer in SFC) as a solid. Example 50: LRMS m/z (M+H) 447.1 found, 447.2 required. Example 51: LRMS m/z (M+H) 447.2 found, 447.2 required.

EXAMPLES 52 and 53

(1-Cyclopropyl-1-{5-[(3R,6R)-6-methyl-1-{[2-(2H-1,2,3-triazol-2-yl)phenyl]carbonyl}piperidin-3-yl]isoxazol-3-yl}ethanol) (Ex. 52) and (1-Cyclopropyl-1-{5-[(3R,6R)-6-methyl-1-{[2-(2H-1,2,3-triazol-2-yl)phenyl]carbonyl}piperidin-3-yl]isoxazol-3-yl}ethanol) (Ex. 53)

94

Step 1: 5-((3R,6R)-1-(2-(2H-1,2,3-Triazol-2-yl)benzoyl)-6-methylpiperidin-3-yl)isoxazole-3-carboxylic acid (52)

To a solution of compound 30 (Example 20, Step 2) (4.5 g, 11 mmol) in MeOH (50 mL) was added LiOH.H$_2$O (0.508 g, 12.1 mmol). The resulting mixture was stirred at RT overnight, then concentrated in vacuo to remove most of MeOH, diluted with water (50 mL) and extracted with EtOAc (30 mL×3). The combined organic layer was washed with water (20 mL) and brine (20 mL), dried over Na$_2$SO$_4$, filtered and concentrated in vacuo to give the desired product as a solid. LRMS m/z (M+H) 382.2 found, 382.2 required.

Step 2: 5-((3R,6R)-1-(2-(2H-1,2,3-Triazol-2-yl)benzoyl)-6-methylpiperidin-3-yl)-N-methoxy-N-methylisoxazole-3-carboxamide (53)

To a solution of the product from step 1 (3.0 g, 7.8 mmol) in DCM (50 mL) was added EDCI (2.9 g, 15.6 mmol) and HOBt (2.1 g, 15.6 mmol). The resulting mixture was stirred at RT for 1 h, then O,N-Dimethyl-hydroxylamine hydrochloride (2.29 g, 23.6 mmol) and Et$_3$N (2.4 g, 23.6 mmol) were added. The mixture was stirred at RT overnight, diluted with water (30 mL), and extracted with EtOAc (30 mL×3). The combined organic layers were washed with water (20

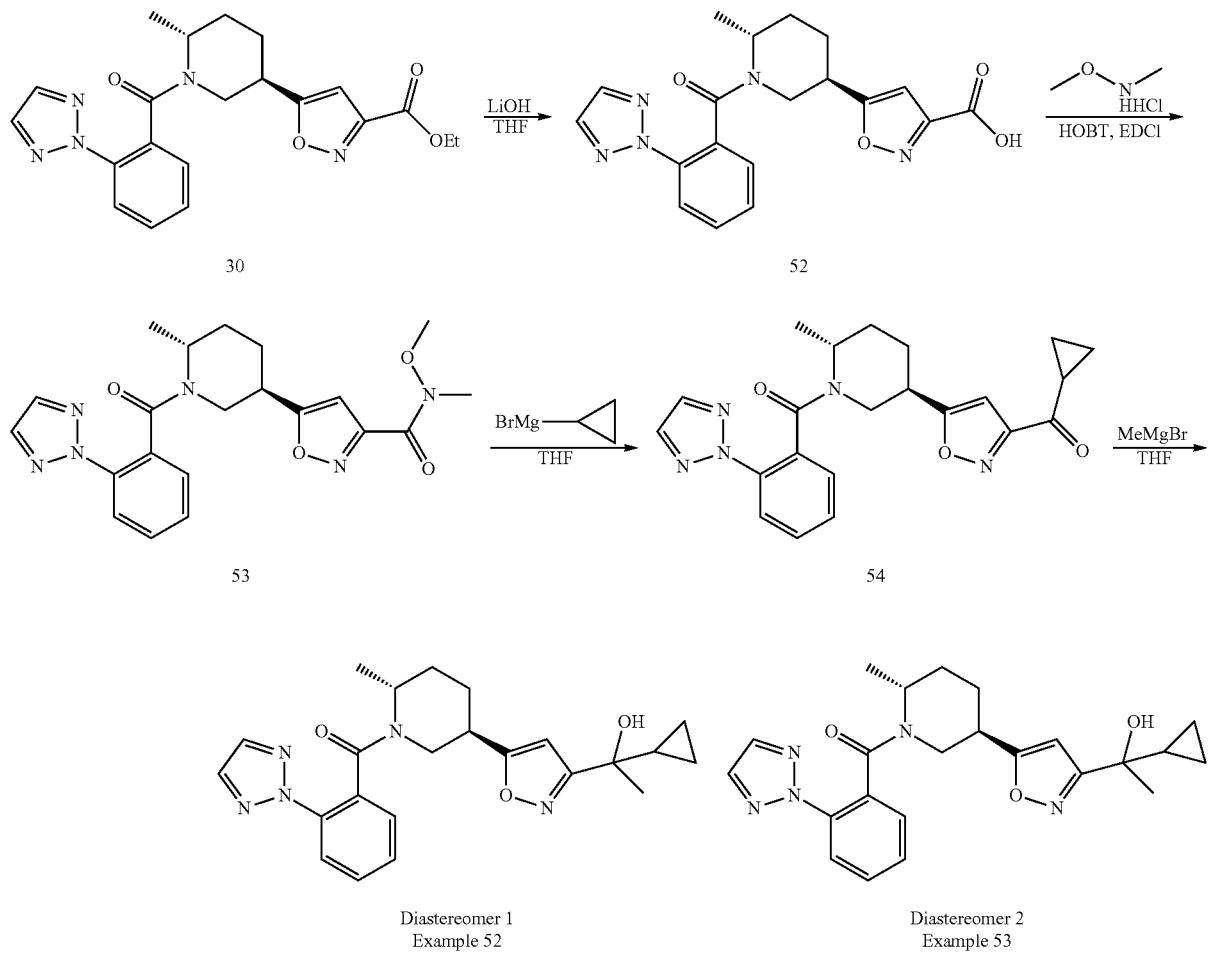

Diastereomer 1
Example 52

Diastereomer 2
Example 53 mL) and brine (20 mL), dried over Na₂SO₄, filtered and concentrated in vacuo. The residue was purified by chromatography on silica (20% EtOAc in petroleum ether) to give the desired product as a solid. LRMS m/z (M+H) 425.2 found, 425.2 required.

Step 3: (5-((3R,6R)-1-(2-(2H-1,2,3-Triazol-2-yl) benzoyl)-6-methylpiperidin-3-yl)isoxazol-3-yl)(cyclopropyl)methanone (54)

To a solution of the product from step 2 (500 mg, 1.18 mmol) in THF (7 mL) was added cyclopropylmagnesium bromide (9.45 mL, 4.72 mmol) at 0° C. The resulting mixture was stirred at RT for 1 h, quenched with aq. NH₄Cl (10 mL) and extracted with EtOAc (10 mL×3). The combined organic layers were washed with brine (20 mL), dried over Na₂SO₄, filtered and the filtrate was concentrated in vacuo. The residue was purified by preparative TLC to give the title compound as an oil. LRMS m/z (M+H) 406.2 found, 406.2 required Step 4: 1-Cyclopropyl-1-{5-[(3R,6R)-6-methyl-1-{[2-(2H-1,2,3-triazol-2-yl)phenyl]carbonyl}piperidin-3-yl]isoxazol-3-yl}ethanol (Example 52) and 1-cyclopropyl-1-{5-[(3R,6R)-6-methyl-1-{[2-(2H-1,2,3-triazol-2-yl)phenyl]carbonyl}piperidin-3-yl]isoxazol-3-yl}ethanol (Example 53)

To a solution of the product from step 3 (30 mg, 0.074 mmol) in THF (3 mL) at 0° C. was added MeMgBr (0.074 mL, 0.22 mmol). The resulting mixture was stirred at 0° C. for 1 h, quenched with aq. NH₄Cl (5 mL) and extracted with EtOAc (10 mL×3). The combined organic layers were washed with brine (10 mL) at 0° C. and the filtrate was concentrated in vacuo. The residue was purified by preparative HPLC to give Example 52 (faster eluting isomer in HPLC) as an oil and Example 53 (slower eluting isomer in HPLC) as an oil. Example 52: LRMS m/z (M+H) 422.2 found, 422.2 required. Example 53: LRMS m/z (M+H) 422.2 found, 422.2 required.

EXAMPLES 54 and 55

Examples 54-55 in the following table were prepared according to the methodology herein and the general procedure provided in Examples 52 and 53. The starting materials are either commercially available or may be prepared as described in the intermediates preparation section, or may be prepared from commercially available reagents using conventional reactions well known in the art.

| Example # | R | Chemical Name | LRMS or HRMS (M + H⁺) |
|---|---|---|---|
| 54 | (structure) | 2-{5-[(3R,6R)-6-Methyl-1-{[2-(2H-1,2,3-triazol-2-yl)phenyl]carbonyl}piperidin-3-yl]isoxazol-3-yl}butan-2-ol | Calc'd 410.2, found 410.2 |
| 55 | (structure) | 2-{5-[(3R,6R)-6-Methyl-1-{[2-(2H-1,2,3-triazol-2-yl)phenyl]carbonyl}piperidin-3-yl]isoxazol-3-yl}butan-2-ol | Calc'd 410.2, found 410.2 |

EXAMPLE 56

((2R,5R)-2-Methyl-5-[3-(tetrahydrofuran-2-yl)isoxazol-5-yl]-1-{[2-(2H-1,2,3-triazol-2-yl)phenyl]carbonyl}piperidine

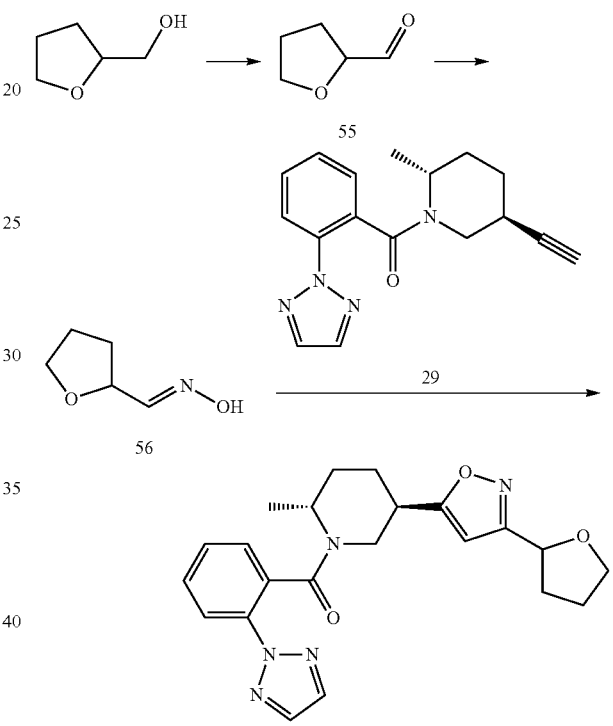

Example 56

Step 1: Tetrahydrofuran-2-carbaldehyde (55)

To a solution of (tetrahydrofuran-2-yl)methanol (2.0 g, 19.6 mmol) in DCM (150 mL) was added DMP (9.6 g, 22.6 mmol) at RT. The mixture was stirred at RT overnight, diluted with water (100 mL) and extracted with DCM (100 mL×3). The combined organic layers were washed with brine, dried over MgSO₄, filtered, and the filtrate concentrated in vacuo. The residue was purified by chromatography on silica (20% EtOAc in petroleum ether) to give the title compound as an oil.

Step 2: (E)-Tetrahydrofuran-2-carbaldehyde oxime (56)

To a solution of the product from step 1 (800 mg, 8 mmol) and hydroxylamine hydrochloride (828 mg, 12 mmol) in EtOH/H₂O (10 mL/1 mL) was added Na₂CO₃ (1.27 g, 12 mmol) at RT. The reaction mixture was stirred at 70° C.

overnight, cooled to RT, quenched with saturated aq. NaHCO₃ and extracted with EtOAc (20 mL×3). The combined organic layers were washed with brine, dried over MgSO₄, filtered, and the filtrate was concentrated in vacuo. The residue was purified by chromatography on silica (30% EtOAc in petroleum ether) to give the title compound as an oil. LRMS m/z (M+H) 116.2 found, 116.2 required.

Step 3: (2R,5R)-2-Methyl-5-[3-(tetrahydrofuran-2-yl)isoxazol-5-yl]-1-{[2-(2H-1,2,3-triazol-2-yl)phenyl]carbonyl}piperidine (Example 56)

A solution of compound 29 (Example 20, Step 2) (50 mg, 0.17 mmol) and NCS (68 mg, 0.51 mmol) in DMF (2 mL) was stirred at RT for 1 h. The product from step 2 (58 mg, 0.51 mmol) in DMF (1 mL) was added, followed by TEA (52 mg, 0.51 mmol). The reaction mixture was stirred at 50° C. overnight, cooled to RT, concentrated in vacuo and purified directly by preparative HPLC to give the title compound as an oil. LRMS m/z (M+H) 408.2 found, 408.2 required.

EXAMPLE 57

((2R,5R)-5-[3-(1-Methoxy-1-methylethyl)isoxazol-5-yl]-2-methyl-1-{[2-(2H-1,2,3-triazol-2-yl)phenyl]carbonyl}piperidine)

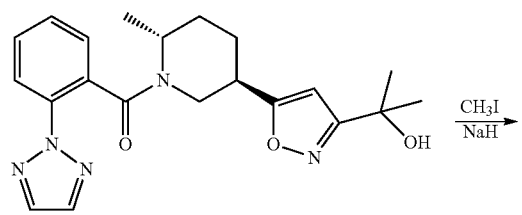

Example 20

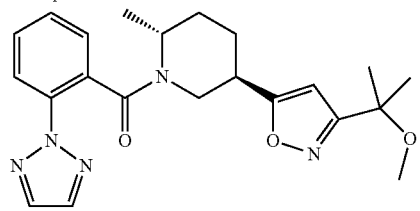

Example 57

(2R,5R)-5-[3-(1-Methoxy-1-methylethyl)isoxazol-5-yl]-2-methyl-1-{[2-(2H-1,2,3-triazol-2-yl)phenyl]carbonyl}piperidine (Example 57)

To a solution of Example 20 (400 mg, 1.01 mmol) in DMF (10 mL) at 0° C. was added NaH (80 mg, 2 mmol, 60 wt. % in oil). The mixture was stirred at 0° C. for 30 min, MeI (142 mg, 1.01 mmol) added and the mixture stirred at 0° C. for 1 h, then quenched with 0.5 mL of water and purified directly by preparative HPLC to give the title compound as an oil. LRMS m/z (M+H) 410.2 found, 410.2 required.

EXAMPLE 58

(2-{3-[(3R,6R)-6-Methyl-1-{[2-(2H-1,2,3-triazol-2-yl)phenyl]carbonyl}piperidin-3-yl]isothiazol-5-yl}propan-2-ol}piperidine)

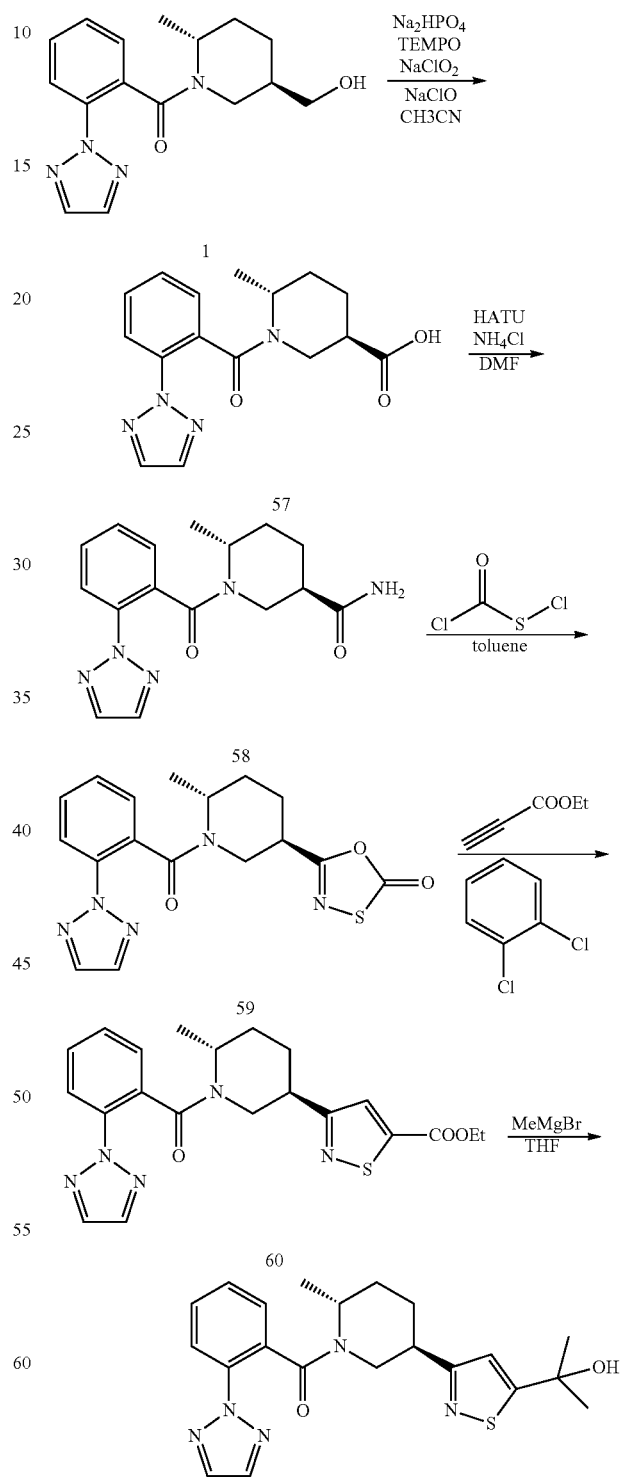

Example 58

Step 1: (3R,6R)-1-(2-(2H-1,2,3-Triazol-2-yl)benzoyl)-6-methylpiperidine-3-carboxylic acid (57)

To a solution of compound 1 (Example 1, Step 1) (5.0 g, 16.7 mmol) in CH$_3$CN (50 mL) were added Na$_2$HPO$_4$ buffer (100 mL) and TEMPO (0.26 g, 1.67 mmol). The resulting mixture was warmed to 35° C., and a solution of NaClO$_2$ (3 g, 33.2 mmol) in water (500 mL) and NaClO (3.5 mL) added simultaneously over 10 min. The resulting mixture was stirred at 35° C. overnight, cooled to RT and concentrated in vacuo to remove most of CH$_3$CN. EtOAc (200 mL) and water (100 mL) were added to the residue, the mixture acidified to pH~3 and extracted with EtOAc (100 mL×2). The combined organic layers were washed with brine, dried over Na$_2$SO$_4$, filtered and concentrated in vacuo to give the title compound as a solid, which was used directly in the next step. LRMS m/z (M+H) 315.1 found, 315.1 required

Step 2: (3R,6R)-1-(2-(2H-1,2,3-Triazol-2-yl)benzoyl)-6-methylpiperidine-3-carboxamide (58)

To a solution of the product from step 1 (8 g, 25.5 mmol) in DMF (100 mL) were added HATU (11.6 g, 30.6 mmol), DIEA (16.4 g, 127 mmol) and NH$_4$Cl (4.09 g, 76.5 mmol). The resulting mixture was stirred at RT overnight, water (150 mL) added, and the mixture extracted with DCM (200 mL×4). The combined organic layers were washed with brine (100 mL×5), dried over Na$_2$SO$_4$, filtered and the filtrate concentrated in vacuo. The residue was purified by chromatography on silica (60% EtOAc in petroleum ether) to give the title compound as a solid. LRMS m/z (M+H) 314.1 found, 314.1 required.

Step 3: 5-((3R,6R)-1-(2-(2H-1,2,3-Triazol-2-yl)benzoyl)-6-methylpiperidin-3-yl)-1,3,4-oxathiazol-2-one (59)

To a solution of the product from step 2 (5.5 g, 17.6 mmol) in toluene (50 mL) was added carbonochloridic hypochlorous thioanhydride (4.6 g, 35 mmol). The mixture was stirred at 100° C. for 12 h, cooled to RT and concentrated in vacuo. The residue was purified by chromatography on silica (30% EtOAc in petroleum ether) to give the title compound as a solid. LRMS m/z (M+H) 372.1 found, 372.2 required.

Step 4: Ethyl 3-((3R,6R)-1-(2-(2H-1,2,3-triazol-2-yl)benzoyl)-6-methylpiperidin-3-yl)isothiazole-5-carboxylate (60)

To a solution of the product from step 3 (2.1 g, 5.66 mmol) in dichlorobenzene (25 mL) was added propynoic acid ethyl ester (5.5 g, 56 mmol) and the mixture heated at 135° C. for 12 h. The cooled mixture was concentrated in vacuo and the residue purified by chromatography on silica (30% EtOAc in petroleum ether) to give the title compound as an oil. LRMS m/z (M+H) 426.2 found, 426.2 required.

Step 5: 2-{3-[(3R,6R)-6-Methyl-1-{[2-(2H-1,2,3-triazol-2-yl)phenyl]carbonyl}piperidin-3-yl]isothiazol-5-yl}propan-2-ol (Example 58)

To a solution of the product from step 4 (213 mg, 0.5 mmol) in THF (5 mL) was added MeMgBr solution (2.0 mL, 3M, 6 mmol). The resulting mixture was stirred at RT for 3 h, quenched with NH$_4$Cl (10 mL) and extracted with EtOAc (20 mL×3). The combined organic layers were washed with brine (100 mL), dried over Na$_2$SO$_4$, filtered and the filtrate concentrated in vacuo. The residue was purified by preparative HPLC to give the title compound as a solid. LRMS m/z (M+H) 412.2 found, 412.2 required.

EXAMPLE 59

(2-{3-[(3R,6R)-6-Methyl-1-{[2-(2H-1,2,3-triazol-2-yl)thiophen-3-yl]carbonyl}piperidin-3-yl]isothiazol-5-yl}propan-2-ol)

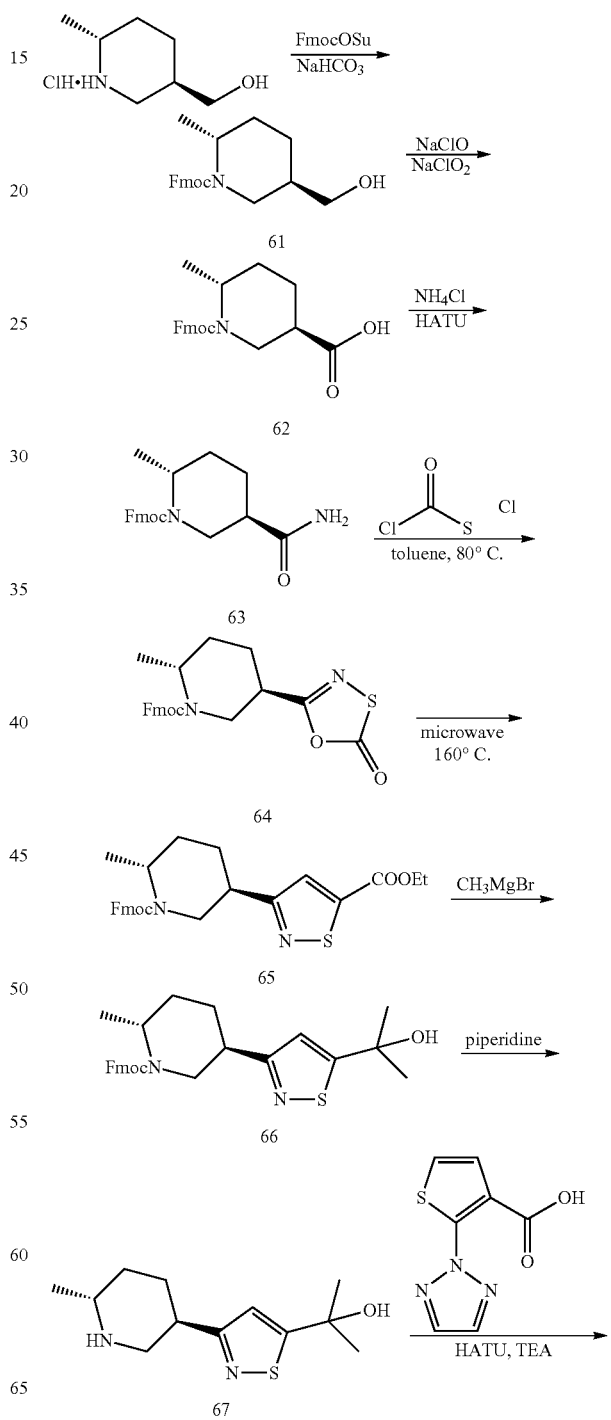

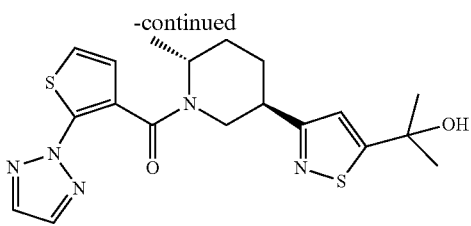

Example 59

Step 1: (2R,5R)-(9H-Fluoren-9-yl)methyl 5-(hydroxymethyl)-2-methylpiperidine-1-carboxylate (61)

To a solution of ((3R,6R)-6-methylpiperidin-3-yl)methanol hydrochloride (2.0 g, 12.0 mmol) in dioxane (20 mL) was added NaHCO$_3$ (2.5 g, 30.0 mmol) in 5 mL of water at 0° C. followed by slow addition of FmocOSu (4.48 g, 13.3 mmol) in dioxane (10 mL). The resulting mixture was stirred at RT overnight, diluted with water (20 mL) extracted with EtOAc (50 mL×3). The combined organic layers were washed with brine (20 mL×3), dried over MgSO$_4$, filtered and the filtrate concentrated in vacuo. The residue was purified by chromatography on silica (25% EtOAc in petroleum ether) to give the title compound as a solid. LRMS m/z (M+H) 352.2 found, 352.2 required.

Step 2: (3R,6R)-1-(((9H-fluoren-9-yl)methoxy)carbonyl)-6-methylpiperidine-3-carboxylic acid (62)

To a solution of the product from step 1 (3.0 g, 8.55 mol) in CH$_3$CN (40 mL) was added a solution of Na$_2$HPO$_4$ (840 mg, 5.91 mmol) in 24 mL of water, and TEMPO (133 mg, 0.855 mol). The mixture was heated to 35° C. A solution of NaClO$_2$ (1.54 g, 17.1 mmoL) in water (10 mL) and NaClO (1.9 mL) were added simultaneously. The mixture was stirred at 35° C. overnight, concentrated in vacuo, water (50 mL) added and the mixture adjusted to pH~5 with 2 M HCl, and extracted with EtOAc (50 mL×3). The combined organic layers were washed with brine (20 mL×3), dried over MgSO$_4$, filtered and the filtrate concentrated in vacuo to give the title compound as a solid. LRMS m/z (M+H) 366.1 found, 366.2 required.

Step 3: (2R,5R)-(9H-Fluoren-9-yl)methyl 5-carbamoyl-2-methylpiperidine-1-carboxylate (63)

To a solution of the product from step 2 (3.0 g, 8.20 mmol) in DCM (30 mL) were added HATU (4.20 g, 11.0 mmol), TEA (3.00 mL, 20.0 mmol) and ammonium chloride (660 mg, 12.3 mmol). The mixture was stirred at RT overnight, water (30 mL) added and the mixture extracted with DCM (50 mL×3). The combined organic layers were washed with brine, dried over MgSO$_4$, filtered and the filtrate concentrated in vacuo. The residue was purified by chromatography on silica (100% EtOAc in petroleum ether) to give the title compound as a solid. LRMS m/z (M+H) 365.1 found, 365.2 required.

Step 4: (2R,5R)-(9H-Fluoren-9-yl)methyl 2-methyl-5-(2-oxo-1,3,4-oxathiazol-5-yl)piperidine-1-carboxylate (64)

To a solution of the product from step 3 (1.00 g, 2.75 mol) in toluene (20 mL) was added carbonochloridic hypochlorous thioanhydride (720 mg, 5.50 mmol). The mixture was heated at 80° C. overnight, cooled to RT and concentrated in vacuo. The residue was purified by chromatography on silica (25% EtOAc in petroleum ether) to give the title compound as a solid. LRMS m/z (M+H) 423.1 found, 423.2 required.

Step 5: Ethyl 3-((3R,6S)-1-(((9H-fluoren-9-yl)methoxy)carbonyl)-6-methylpiperidin-3-yl)isothiazole-5-carboxylate (65)

To a solution of the product from step 4 (900 mg, 2.13 mol) in 1,2-dichlorobenzene (20 mL) was added ethyl propiolate (2.09 g, 21.3 mmol). The mixture was heated under MW irradiation at 160° C. for 20 min, cooled to RT, and concentrated in vacuo. The residue was purified by chromatography on silica (25% EtOAc in petroleum ether) to give the title compound as a solid. LRMS m/z (M+H) 477.1 found, 477.2 required.

Step 6: (2S,5R)-(9H-Fluoren-9-yl)methyl 5-(5-(2-hydroxypropan-2-yl)isothiazol-3-yl)-2-methylpiperidine-1-carboxylate (66)

To a solution of the product from step 5 (600 mg, 1.24 mmol) in dry THF (20 mL) at 0° C. was added a solution of CH$_3$MgBr solution (2.1 mL, 3 M, 6.3 mmol) dropwise. The mixture was stirred at 0° C. for 2 h, then quenched with water (20 mL), and extracted with EtOAc (30 mL×3). The combined organic layers were dried over MgSO$_4$, filtered, the filtrate concentrated in vacuo and the residue purified by preparative HPLC to give the title compound as an oil. LRMS m/z (M+H) 463.2 found, 463.2 required.

Step 7: 2-(3-((3R,6R)-6-Methylpiperidin-3-yl)isothiazol-5-yl)propan-2-ol (67)

To a solution of the product from step 6 (140 mg, 0.300 mmol) in dry MeOH (10 mL) was added piperidine (0.75 mL) at RT. The mixture was stirred at RT overnight, concentrated in vacuo and the residue was purified by preparative TLC (9% MeOH in dichloromethane) to give the title compound as an oil. LRMS m/z (M+H) 241.1 found, 241.2 required.

Step 8: 2-{3-[(3R,6R)-6-Methyl-1-{[2-(2H-1,2,3-triazol-2-yl)thiophen-3-yl]carbonyl}piperidin-3-yl]isothiazol-5-yl}propan-2-ol (Example 59)

To a solution of the product from step 7 (30.0 mg, 0.125 mmol) in DCM (5 mL) was added HATU (57.0 mg, 0.150 mmol), 2-(2H-1,2,3-triazol-2-yl)thiophene-3-carboxylic acid (30.0 mg, 0.150 mmol) and TEA (32.0 mg, 0.300 mmol). The mixture was stirred at RT overnight, concentrated in vacuo and the residue was purified directly by preparative HPLC to give the title compound as an oil. LRMS m/z (M+H) 418.2 found, 418.1 required.

EXAMPLES 60 to 63

Examples 60-63 in the following table were prepared according to the methodology herein and the general procedure provided in Example 59. The starting materials are either commercially available or may be prepared as described in the intermediates preparation section, or may be prepared from commercially available reagents using conventional reactions well known in the art.

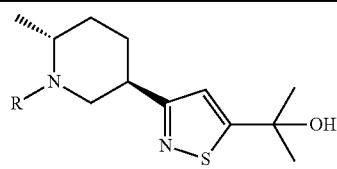

| Example # | R | Chemical Name | LRMS or HRMS (M + H⁺) |
|---|---|---|---|
| 60 | (2-(2H-tetrazol-2-yl)phenyl)carbonyl group | 2-{3-[(3R,6R)-6-Methyl-1-{[2-(2H-tetrazol-2-yl)phenyl]carbonyl}piperidin-3-yl]isothiazol-5-yl}propan-2-ol | Calc'd 413.2, found 413.2 |
| 61 | [4-Fluoro-2-(2H-1,2,3-triazol-2-yl)phenyl]carbonyl group | 2-{3-[(3R,6R)-1-{[4-Fluoro-2-(2H-1,2,3-triazol-2-yl)phenyl]carbonyl}-6-methylpiperidin-3-yl]isothiazol-5-yl}propan-2-ol | Calc'd 430.2, found 430.1 |
| 62 | 1-(2-cyanocyclopropyl)-phenyl carbonyl group | 1-[2-({(2R,5R)-5-[5-(1-Hydroxy-1-methylethyl)isothiazol-3-yl]-2-methylpiperidin-1-yl}carbonyl)phenyl]cyclopropanecarbonitrile | Calc'd 410.2, found 410.2 |
| 63 | (2-pyrimidin-2-ylphenyl)carbonyl group | 2-(3-{(3R,6R)-6-Methyl-1-[(2-pyrimidin-2-ylphenyl)carbonyl]piperidin-3-yl}isothiazol-5-yl)propan-2-ol | Calc'd 423.2, found 423.1 |

EXAMPLE 64

(2-(3-{(3R,6R)-6-Methyl-1-[(2-pyrimidin-2-ylthiophen-3-yl)carbonyl]piperidin-3-yl}isothiazol-5-yl)propan-2-ol)

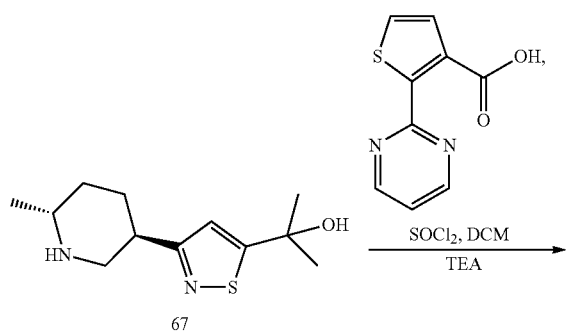

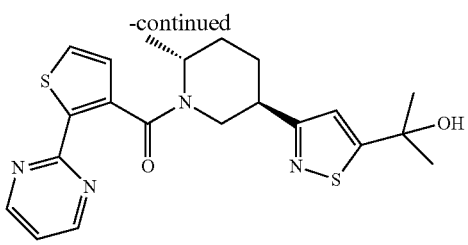

Example 64

2-(3-{(3R,6R)-6-Methyl-1-[(2-pyrimidin-2-ylthiophen-3-yl)carbonyl]piperidin-3-yl}isothiazol-5-yl)propan-2-ol (Example 64)

A mixture of 2-pyrimidin-2-yl-thiophene-3-carboxylic acid (30 mg, 0.145 mmol) in SOCl₂ (2 mL) was stirred at 80° C. for 1 h, cooled to RT and concentrated in vacuo. To a solution of compound 67 (Example 59, Step 7) (30 mg, 0.125 mmol) and TEA (31 mg, 0.3 mmol) in DCM (4 mL) at 0° C. was added dropwise a solution of above residue in DCM (2 mL). The mixture was stirred at RT for 12 h, concentrated in vacuo and the residue purified by preparative HPLC to give the title compound as an oil. LRMS m/z (M+H) 429.1 found, 429.1 required.

EXAMPLES 65 to 70

Examples 65-70 in the following table were prepared according to the general procedure provided in Example 64. The starting materials are either commercially available or may be prepared as described in the intermediates preparation section, or may be prepared from commercially available reagents using conventional reactions well known in the art.

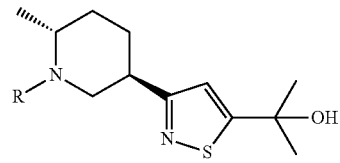

| Example # | R | Chemical Name | LRMS or HRMS (M + H⁺) |
|---|---|---|---|
| 65 | | 2-(3-{(3R,6R)-6-Methyl-1-[(4-pyrimidin-2-ylthiophen-3-yl)carbonyl]piperidin-3-yl}isothiazol-5-yl)propan-2-ol | Calc'd 429.1, found 429.1 |
| 66 | | 2-{3-[(3R,6R)-6-Methyl-1-{[4-(2H-1,2,3-triazol-2-yl)thiophen-3-yl]carbonyl}piperidin-3-yl]isothiazol-5-yl}propan-2-ol | Calc'd 418.1, found 418.1, |
| 67 | | Methyl 2-({(2R,5R)-5-[5-(1-hydroxy-1-methylethyl)isothiazol-3-yl]-2-methylpiperidin-1-yl}carbonyl)benzoate | Calc'd 403.2, found 403.1 |
| 68 | | 2-{3-[(3R,6R)-6-Methyl-1-{[2-(trifluoromethoxy)phenyl]carbonyl}piperidin-3-yl]isothiazol-5-yl}propan-2-ol | Calc'd 429.1, found 429.1 |
| 69 | | 2-{3-[(3R,6R)-1-{[2-(2,2-Difluoroethoxy)pyridin-3-yl]carbonyl}-6-methylpiperidin-3-yl]isothiazol-5-yl}propan-2-ol | Calc'd 426.2, found 426.1 |

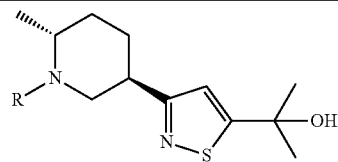

| Example # | R | Chemical Name | LRMS or HRMS (M + H⁺) |
|---|---|---|---|
| 70 | (2-(2-methoxyethyl)phenyl)carbonyl group | 2-{3-[(3R,6R)-1-{[2-(2-methoxyethyl)phenyl]carbonyl}-6-methylpiperidin-3-yl]isothiazol-5-yl}propan-2-ol | Calc'd 403.2, found 403.2, |

ACTIVITIES OF COMPOUNDS

The following table shows representative data for the compounds of the Examples as Orexin receptor antagonists or determined by the assays described herein.

| Example | hOX2 FLIPR IC$_{50}$ (nM) | hOX1 FLIPR IC$_{50}$ (nM) |
|---|---|---|
| 1 | 46.9 | >10000 |
| 2 | 103.6 | >10000 |
| 3 | 1427.0 | >10000 |
| 4 | 277.8 | >10000 |
| 5 | 1193.0 | >10000 |
| 6 | 1840.08 | >10000 |
| 7 | 226.8 | >10000 |
| 8 | 551.6 | >10000 |
| 9 | 25.8 | ~7965 |
| 10 | 15.6 | 2860 |
| 11 | 41.4 | >10000 |
| 12 | 15.0 | >10000 |
| 13 | 635.4 | >10000 |
| 14 | 34.9 | 3644 |
| 15 | 33.9 | ~6826 |
| 16 | 24.3 | >10000 |
| 17 | 24.5 | >10000 |
| 18 | 92.0 | >10000 |
| 19 | 27.3 | >10000 |
| 20 | 30.3 | >10000 |
| 21 | 1121.0 | >10000 |
| 22 | 51.4 | >10000 |
| 23 | 267.9 | >10000 |
| 24 | 215.3 | >10000 |
| 25 | 799.2 | >10000 |
| 26 | 22.9 | 1808 |
| 27 | 603.5 | >10000 |
| 28 | 1421.0 | >10000 |
| 29 | 8.8 | 1900 |
| 30 | 250.9 | >10000 |
| 31 | 178.0 | >10000 |
| 32 | 123.8 | >10000 |
| 33 | 134.3 | >10000 |
| 34 | 263.8 | >10000 |
| 35 | 140.2 | >10000 |
| 36 | 212.0 | >10000 |
| 37 | 1034.0 | >10000 |
| 38 | 52.4 | ~7784 |
| 39 | 42.4 | 2440 |
| 40 | 11.0 | 2154 |
| 41 | 17.5 | >10000 |
| 42 | 154.2 | >10000 |
| 43 | 162.4 | >10000 |
| 44 | 26.8 | 2183 |
| 45 | 41.2 | 3418 |
| 46 | 356.1 | >10000 |
| 47 | 327.9 | >10000 |
| 48 | 112.9 | >10000 |
| 49 | 111.8 | >10000 |
| 50 | 110.0 | >10000 |
| 51 | 145.6 | >10000 |
| 52 | 47.3 | 2364 |
| 53 | 34.3 | 3084 |
| 54 | 76.1 | >10000 |
| 55 | 39.8 | >10000 |
| 56 | 310.7 | >10000 |
| 57 | 14.4 | 1030 |
| 58 | 13.9 | ~8306 |
| 59 | 24.9 | 3963 |
| 60 | 63.8 | >10000 |
| 61 | 18.6 | >10000 |
| 62 | 19.1 | >10000 |
| 63 | 42.3 | >10000 |
| 64 | 36.8 | >10000 |
| 65 | 46.8 | >10000 |
| 66 | 21.1 | >10000 |
| 67 | 43.6 | >10000 |
| 68 | 22.8 | >10000 |
| 69 | 42.8 | >10000 |
| 70 | 934.7 | >10000 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

The invention claimed is:
1. A compound of the formula I:

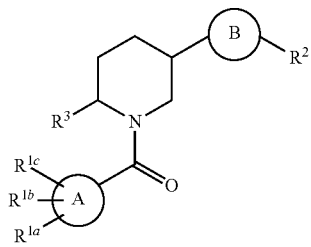

wherein:
A ring is selected from the group consisting of phenyl, pyridyl, thiophenyl, thiazolyl, pyrazinyl and pyrazolyl;
B ring is

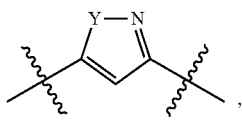

wherein Y is O or S; and wherein symbol

indicates a bond of attachment;
each of $R^{1a}$, $R^{1b}$ and $R^{1c}$ is independently selected from the group consisting of:
(1) hydrogen,
(2) halogen,
(3) hydroxyl,
(4) $C_{1-6}$alkyl, which is unsubstituted or substituted with one to four substituents independently selected from the group consisting of halogen, hydroxyl, $C_{3-6}$cycloalkyl and phenyl.
(5) —O—$C_{1-6}$alkyl, which is unsubstituted or substituted with one to four substituents independently selected from the group consisting of halogen, hydroxyl, $C_{3-6}$cycloalkyl and phenyl.
(6) $C_{3-6}$cycloalkyl, wherein the cycloalkyl is unsubstituted or substituted with one to four substituents independently selected from $R^4$, and
(7) —CN;
$R^2$ is selected from the group consisting of:
(1)

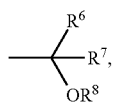

wherein each of $R^6$ and $R^7$ is independently selected from the group consisting of hydrogen, —$C_{1-2}$alkyl, —$C_{1-2}$alkyl substituted with 1-3 halogens and —$C_{3-6}$cycloalkyl; and $R^8$ is hydrogen or —$C_{1-6}$alkyl, and (2) $C_{3-6}$cycloalkyl, which is unsubstituted or substituted with one to three substituents independently selected from the group consisting of $C_{1-6}$alkyl, halogen, hydroxyl, —O—$C_{1-6}$alkyl, —$NH_2$, —NH—$C_{1-6}$alkyl, —(C=O)O—$C_{1-6}$alkyl, and phenyl, wherein the phenyl is unsubstituted or substituted with $C_{1-6}$alkyl, halogen, or $C_{1-6}$alkyl-OH;
$R^3$ is selected from $C_{1-6}$alkyl and $C_{3-6}$cycloalkyl, wherein each of the alkyl and cycloalkyl is unsubstituted or substituted with one to two substituents independently selected from $R^4$;
$R^4$ is selected from the group consisting of:
(1) hydroxyl,
(2) halogen,
(3) $C_{1-6}$alkyl,
(4) —$C_{3-6}$cycloalkyl,
(5) —O—$C_{1-6}$alkyl,
(6) —O—(C=O)—$C_{1-6}$alkyl,
(7) —$NH_2$,
(8) —NH—$C_{1-6}$alkyl,
(9) —$NO_2$,
(10) phenyl,
(11) —$CO_2H$,
(12) —CN, and
(13) —$S(O)_2$—$C_{1-6}$alkyl,
each of $R^{10}$ and $R^{11}$ is independently selected from the group consisting of:
(a) hydrogen,
(b) $C_{1-6}$alkyl, which is unsubstituted or substituted with one to four substituents independently selected from $R^4$,
(c) $C_{3-6}$alkenyl, which is unsubstituted or substituted with one to four substituents independently selected from $R^4$,
(d) $C_{3-6}$alkynyl, which is unsubstituted or substituted with one to four substituents independently selected from $R^4$,
(e) $C_{3-6}$cycloalkyl which is unsubstituted or substituted with one to four substituents independently selected from $R^4$,
(f) phenyl, which is unsubstituted or substituted with one to four substituents independently selected from $R^4$, and
(g) heterocycle, which is unsubstituted or substituted with one to four substituents independently selected from $R^4$; and
m is 0 or 1, n is 0 or 1 (wherein if m is 0 or n is 0, a bond is present);
or a pharmaceutically acceptable salt thereof.

2. The compound of claim 1 of the formula Ia:

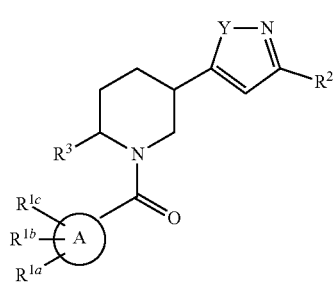

wherein Y is O or S; or a pharmaceutically acceptable salt thereof.

3. The compound of claim 1 of the formula Id:

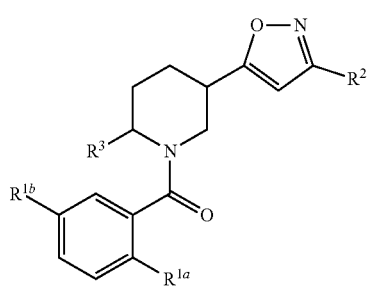

or a pharmaceutically acceptable salt thereof.

4. The compound of claim 1 of the formula Ie:

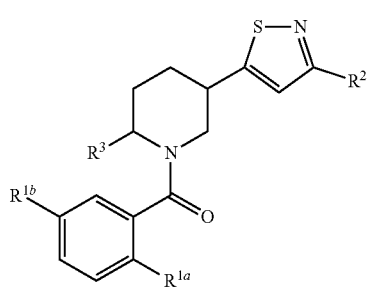

or a pharmaceutically acceptable salt thereof.

5. The compound of claim 1 of the formula If:

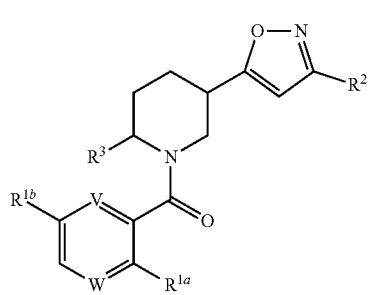

wherein each of V and W is independently CH or N; or a pharmaceutically acceptable salt thereof.

6. The compound of claim 1 of the formula Ig;

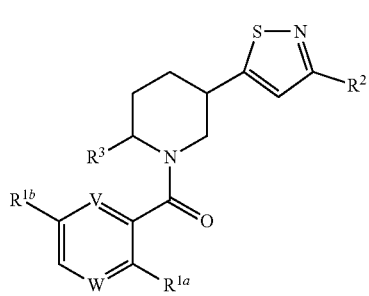

wherein each of V and W is independently CH or N; or a pharmaceutically acceptable salt thereof.

7. The compound of claim 1 of the formula IIa:

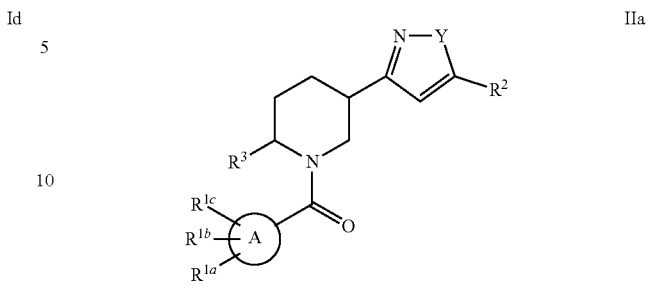

wherein Y is O or S; or a pharmaceutically acceptable salt thereof.

8. The compound of claim 7 of the formula IId:

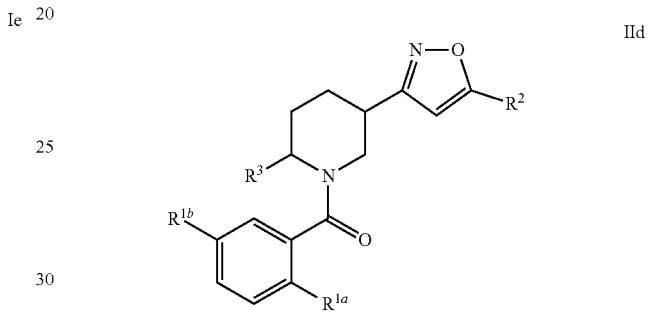

or a pharmaceutically acceptable salt thereof.

9. The compound of claim 7 of the formula IIe:

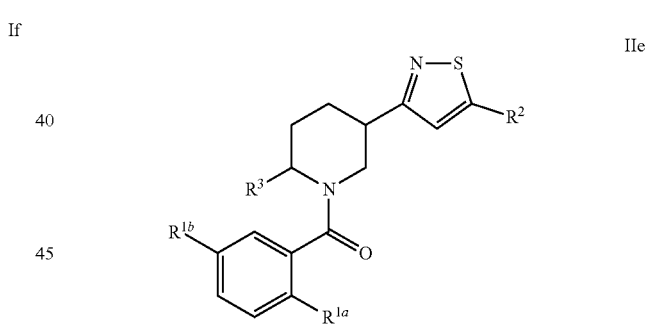

or a pharmaceutically acceptable salt thereof.

10. The compound of claim 1, or a pharmaceutically acceptable salt thereof, wherein $R^{1c}$, if present, is hydrogen, and $R^{1a}$ and $R^{1b}$ are independently selected from the group consisting of:
  (1) hydrogen,
  (2) fluoro;
  (3) chloro,
  (4) bromo,
  (5) methyl,
  (6) ethyl,
  (7) trifluoromethyl,
  (8) cyclopropyl, which is unsubstituted or substituted with —CN, and
  (9) —O—$C_{1-4}$alkyl which is unsubstituted or substituted with 1-3 halogens.

11. The compound of claim 1, or a pharmaceutically acceptable salt thereof, wherein $R^2$ is selected from the group consisting of:

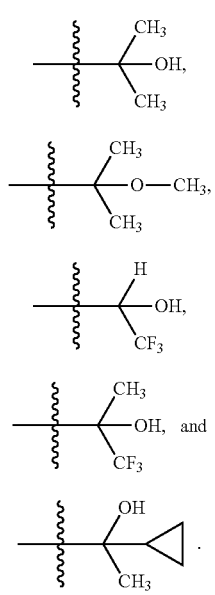

12. The compound of claim 1, or a pharmaceutically acceptable salt thereof, wherein $R^3$ is methyl or ethyl.

13. The compound of claim 1, or a pharmaceutically acceptable salt thereof, wherein $R^4$ is selected from the group consisting of:
(1) hydroxyl,
(2) halogen,
(3) $C_{1-6}$alkyl,
(4) —$C_{3-6}$cyclalkyl,
(5) —$NH_2$,
(6) phenyl, and
(7) —CN.

14. A compound which is selected from the group consisting of:
(1 2-{3-[(3R,6R)-6-Methyl-1-{[2-(2H-1,2,3-triazol-2-yl)phenyl]carbonyl}piperidin-3-yl]isoxazol-5-yl}propan-2-ol),
(1-(2-((2R,5R)-5-(5-(2-Hydroxypropan-2-yl)isoxazol-3-yl)-2-methylpiperidine-1-carbonyl)phenyl)cyclopropanecarbonitrile),
(5-Chloro-2-(2H-1,2,3-triazol-2-yl)phenyl)((2R,5R)-5-(5-(2-hydroxypropan-2-yl)isoxazol-3-yl)-2-methylpiperidin-1-yl)methanone,
(5-Fluoro-2-(2H-1,2,3-triazol-2-yl)phenyl)((2R,5R)-5-(5-(2-hydroxypropan-2-yl)isoxazol-3-yl)-2-methylpiperidin-1-yl)methanone,
((2-Ethoxyphenyl)((2R,5R)-5-(5-(2-hydroxypropan-2-yl)isoxazol-3-yl)-2-methylpiperidin-1-yl)methanone),
(((2R,5R)-5-(5-(2-Hydroxypropan-2-yl)isoxazol-3-yl)-2-methylpiperidin-1-yl)(2-isopropoxypyridin-3-yl)methanone),
((2R,5R)-5-(5-(2-Hydroxypropan-2-yl)isoxazol-3-yl)-2-methylpiperidin-1-yl)(2-(2,2,2-trifluoroethoxy)pyridin-3-yl)methanone,
(2-(2H-1,2,3-Triazol-2-yl)phenyl)((2R,5R)-5-(5-(3-hydroxypentan-3-yl)isoxazol-3-yl)-2-methylpiperidin-1-yl)methanone,
(1-Cyclopropyl-1-{3-[(3R,6R)-6-methyl-1-{[2-(2H-1,2,3-triazol-2-yl)phenyl]carbonyl}piperidin-3-yl]isoxazol-5-yl}ethanol),
((2R)-2-{3-[(3R,6R)-6-Methyl-1-{[2-(2H-1,2,3-triazol-2-yl)phenyl]carbonyl}piperidin-3-yl]isoxazol-5-yl}butan-2-ol),
((2S)-2-{3-[(3R,6R)-6-Methyl-1-{[2-(2H-1,2,3-triazol-2-yl)phenyl]carbonyl}pipieridin-3-yl]isoxazol-5-yl}butan-2-ol),
(1-{3-[(3R,6R)-6-Methyl-1-{[2-(2H-1,2,3-triazol-2-yl)phenyl]carbonyl}piperidin-3-yl)isoxazol-5-yl}cyclobutanol),
(1,1,1-Trifluoro-2-{3-[(3R,6R)-6-methyl-1-{[2-(2H-1,2,3-triazol-2-yl)phenyl]carbonyl}piperidin-3-yl]isoxazol-5-yl}propan-2-ol),
(3-Methyl-2-{3-[(3R,6R)-6-methyl-1-{[2-(2H-1,2,3-triazol-2-yl)phenyl]carbonyl}piperiden-3-yl]isoxazol-5-yl}butan-2-ol),
((2S)-1,1-Diflouro-2-{3-[(3R,6R)-6-methyl-1-{[2-(2H-1,2,3-triazol-2-yl)phenyl]carbonyl}piperidin-3-yl]isoxazol-5-yl}propan-2-ol),
((2R,5R)-5-[5-(1-Methoxy-1-methylethyl)isoxazol-3-yl]-2-methyl-1-{[2-(2H-1,2,3-triazol-2-yl)phenyl]carbonyl}piperidine),
(2-{5-[(3R,6R)-6-Methyl-1-{[2-(2H-1,2,3-triazol-2-yl)phenyl]carbonyl}piperidin-3-yl]isoxazol-3-yl}propan-2-ol),
(2-}5-[(3R,6R)-1-{[2-(Methoxymethyl)phenyl]carbonyl}-6-methylpiperidin-3-yl]isoxazol-3-yl}propan-2-ol),
2-(5-{(3R,6R)-6-Methyl-1-[(2-pyrimidin-2-ylphenyl)carbonyl]piperidin-3-yl}isoxazol-3-yl)propan-2-ol,
2-(5-{(3R,6R)-1-[(2-Ethoxypyridin-3-yl)carbonyl]-6-methylpiperidin-3-yl}isoxazol-3-yl)propan-2-ol,
2-{5-[(3R,6R)-1-{[5-Fluoro-2-(2H-1,2,3-triazol-2-yl)phenyl]carbonyl}methylpiperidin-3-yl]isoxazol-3-yl}propan-2-ol,
2-{5-[(3R,6R)-6-methyl-1-{[3-(1H-pyrazol-1-yl)pyrazin-2-yl]carbonyl}piperidin-3-yl]isoxazol-3-yl}propan-2-ol,
2-{5-[(3R,6R)-1-(Biphenyl-2-ylcarbonyl)-6-methpiperidin-3-yl]isoxazol-3-yl}propan-2-ol,
2-{5-[(3R,6R)-1-{[5-Chloro-2-(2H-1,2,3-triazol-2-yl)phenyl]carbonyl}-6-methylpiperidin-3-yl]isoxazol-3-yl}propan-2-ol,
2-(5-{(3R,6R)-6-Methyl-1-[(3-pyridin-2-ylpyrazin-2-yl)carbonyl]piperidin-3-yl}isoxazol-3-yl)propan-2-ol,
1-[2-({(2R,5R)-5-[3-(1-Hydroxy-1-methylethyl)isoxazol-5-yl]-2-methylpiperidin-1-yl}carbonyl)phenyl]cyclopropanecarbonitrile,
Methyl 2-({(2R,5R)-5-[3-(1-hydroxy-1-methylethyl)isoxazol-5-yl]-2-methylpiperidin-1-yl}carbonyl)benzoate,
2-(5-{(3R,6R)-1-[(2-Ethoxyphenyl)carbonyl]-6-methylpiperidin-3-yl}isoxazol-3-yl)propan-2-ol
2-{5-[(3R,6R)-6-Methyl-1-{[2-(2H-tetrazol-2-yl)phenyl]carbonyl}piperidin-3-yl]isoxazol-3-yl}propan-2-ol,
2-(5-{(3R,6R)-6-Methyl-1-[(2phenylpyridin-3-yl)carbonyl]piperidin-3-yl}isoxazol-3-yl)propan-2-ol,
2-(5-{(3R,6R)-6-Methyl-1-[(3-phenylpyridin-2-yl)carbonyl]piperidin-3-yl}isoxazol-3-yl)propan-2-ol,
2-{5-[(3R,6R)-1-{[2-(2,2-Difluoroethoxy)phenyl]carbonyl}-6-methylpiperidin-3-yl]isoxazol-3-yl}propan-2-ol,
2-{5-[(3R,6R)-6-Methyl-1-{[2-(2,2,2-trifluoroethoxy)phenyl]carbonyl}piperidin-3-yl]isoxazol-3-yl}propan-2-ol,
2-(5-{(3R,6R)-6-Methyl-1-[(2-pyrazin-2-ylphenyl)carbonyl]piperidin-3-yl}isoxazol-3-yl)propan-2-ol, 2-{5-[(3R,6R)-1-{[2-(2,2-Difluorocyclopropyl)phenyl]carbonyl}-6-methylpiperidin-3-yl]isoxazol-3-yl}propan-2-ol,
(2-{5-[(3R,6R)-6-Ethyl-1-{[2-(2H-1,2,3-triazol-2-yl)phenyl]carbonyl}piperidin-3-yl]isoxazol-3-yl}propan-2-ol),
((1R)-2,2,2-Trifluoro-1-{5-[(3R,6R)-6-methyl-1-{[2-(2H-1,2,3-triazol-2-yl)phenyl]carbonyl}piperidin-3-yl]isoxazol-3-yl}ethanol),
((1S)-2,2,2-Trifluoro-1-{5-[(3R,6R)-6-methyl-1-{[2-(2H-1,2,3-triazol-2-yl)phenyl]carbonyl}piperidin-3-yl]isoxazol-3-yl}ethanol),
((1R)-2,2,2-Trifluoro-1-{5-[(3R,6R)-6-methyl-1-{[2-(2H-1,2,3-triazol-2-yl)thiophen-3-yl]carbonyl}piperidin-3-yl]isoxazol-3-yl}ethanol),
((1S)-2,2,2-Trifluoro-1-{5-[(3R,6R)-6-methyl-1-{[2-(2H-1,2,3-triazol-2-yl)thiophen-3-yl]carbonyl}piperidin-3-yl]isoxazol-3-yl}ethanol),
1-(2-{[(2R,5R)-2-Methyl-5-{3-[(1R)-2,2,2-Trifluoro-1-hydroxyethyl]isoxazol-5-yl}piperidin-1-yl]carbonyl}phenyl)cyclopropanecarbonitrile,
1-(2-{[(2R,5R)-2-Methyl-5-{3-[(1S)-2,2,2-trifluoro-1-hydroxyethyl]isoxazol-5-yl}piperidin-1-yl]carbonyl}phenyl)cyclopropanecarbonitrile,
(1R)-2,2,2-Trifluoro-1-{5-[(3R,6R)-6-methyl-1-{[2-(2H-tetrazol-2-yl)phenyl]carbonyl}piperidin-3-yl]isoxazol-3-yl}ethanol,
(1S)-2,2,2-Trifluoro-1-{5-[(3R,6R)-6-methyl-1-{[2-(2H-tetrazol-2-yl)phenyl]carbonyl}piperidin-3-yl]isoxazol-3-yl}ethanol,
((1S)-2,2,2-Trifluoro-1-(5-{(3R,6R)-6-methyl-1-[(2-pyrimidin-2-ylthiophen-3-yl)carbonyl]piperidin-3-yl}isoxazol-3-yl)ethanol),
((1R)-2,2,2-Trifluoro-1-(5-{(3R,6R)-6-methyl-1-[(2-pyrimidin-2-ylthiophen-3-yl)carbonyl]piperidin-3-yl}isoxazol-3-yl)ethanol),
((1R)-2,2,2-Trifluoro-1-(5-{(3R,6R)-6-methyl-1-[(2-pyrimidin-2-ylphenyl)carbonyl]piperidin-3-yl}isoxazol-3-yl)ethanol),
((1S)-2,2,2-Trifluoro-1-(5-{(3R,6R)-6-methyl-1-[(2-pyrimidin-2-ylphenyl)carbonyl]piperidin-3-yl}isoxazol-3-yl)ethanol),
(1-Cyclopropyl-1-{5-[(3R,6R)-6-methyl-1-{[2-(2H-1,2,3-triazol-2-yl)phenyl]carbonyl}piperidin-3-yl]isoxazol-3-yl}ethanol),
2-{5-[(3R,6R)-6-Methyl-1-{[2-(2H-1,2,3-triazol-2-yl)phenyl]carbonyl}piperidin-3-yl]isoxazol-3-yl}butan-2-ol,
((2R,5R)-2-Methyl-5-[3-(tetrahydrofuran-2-yl)isoxazol-5-yl]-1-{[2-(2H-1,2,3-triazol-2-yl)phenyl]carbonyl}piperidine),
((2R,5R)-5-[3-(1-Methoxy-1-methylethyl)isoxazol-5-yl]-2-methyl-1-{[2-(2H-1,2,3-triazol-2-yl)phenyl]carbonyl}piperidine),
(2-{3-[(3R,6R)-6-Methyl-1-{[2-(2H-1,2,3-triazol-2-yl)thiophen-3-yl]carbonyl}piperidin-3-yl]isothiazol-5-yl}propan-2-ol),
2-{3-[(3R,6R)-6-Methyl-1-{[2-(2H-tetrazol-2-yl)phenyl]carbonyl}piperidin-3-yl]isothiazol-5-yl}propan-2-ol,
2-{3-[(3R,6R)-1-{[4-Fluoro-2-(2H-1,2,3-triazol-2-yl)phenyl]carbonyl}-6-methylpiperidin-3-yl]isothiazol-5-yl}propan-2-ol,
1-[2-({(2R,5R)-5-[5-(1-Hydroxy-1-methylethyl)isothiazol-3-yl]-2-methylpiperidin-1-yl}carbonyl)phenyl]cyclopropanecarbonitrile,
2-(3-{(3R,6R)-6-Methyl-1-[(2-pyrimidin-2-ylphenyl)carbonyl]piperidin-3-isothiazol-5-yl)propan-2-ol,
(2-(3-{(3R,6R)-6-Methyl-1-[(2-pyrimidin-2-ylthiophen-3-yl)carbonyl]piperidin-3-yl}isothiazol-5-yl)propan-2-ol),
2-(3-{(3R,6R)-6-Methyl-1-[(4-pyrimidin-2-ylthiophen-3-yl)carbonyl]piperidin-3-yl}isothiazol-5-yl)propan-2-ol,
2-{3-[(3R,6R)-6-Methyl-1-{[4-(2H-1,2,3-triazol-2-yl)thiophen-3-yl]carbonyl}piperidin-3-yl]isothiazol-5-yl}propan-2-ol,
Methyl 2-({(2R,5R)-5-[5-(1-hydroxy-1-methylethyl)isothiazol-3-yl]-2-methylpiperidin-1-yl}carbonyl)benzoate,
2-{3-[(3R,6R)-6-Methyl-1-{[2-(trifluoromethoxy)phenyl]carbonyl}piperidin-3-yl]isothiazol-5-yl}propan-2-ol,
2-{3-[(3R,6R)-1-{[2-(2,2-Difluoroethoxy)pyridin-3-yl]carbonyl}-6-methylpiperidin-3-yl]isothiazol-5-yl}propan-2-ol, and
2-{3-[(3R,6R)-1-{[2-(2-methoxyethyl)phenyl]carbonyl}-6-methylpiperidin-3-yl]isothiazol-5-yl}propan-2-ol;
or a pharmaceutically acceptable salt thereof.

15. A composition which comprises an inert carrier and a compound of claim 1, or a pharmaceutically acceptable salt thereof.

* * * * *